United States Patent [19]

Baker et al.

[11] Patent Number: 5,317,103
[45] Date of Patent: May 31, 1994

[54] INDOLE-SUBSTITUTED FIVE-MEMBERED HETEROAROMATIC COMPOUNDS AS 5-$HT_1$ AGONISTS

[75] Inventors: Raymond Baker, Much Hadham; Austin J. Reeve, Great Dunmow; Leslie J. Street, Harlow, all of England

[73] Assignee: Merck Sharp & Dohme Limited, Hoddesdon, England

[21] Appl. No.: 914,683

[22] Filed: Jul. 16, 1992

Related U.S. Application Data

[63] Continuation of Ser. No. 641,422, Jan. 15, 1991, abandoned.

[51] Int. Cl.$^5$ .................. C07D 417/04; C07D 413/04; C07D 451/00; C07D 453/02
[52] U.S. Cl. ..................................... 544/367; 546/277; 548/128; 548/133; 548/134; 548/466; 548/468
[58] Field of Search ............... 548/468, 133, 466, 134, 548/128; 544/367; 546/277

[56] References Cited

U.S. PATENT DOCUMENTS

| | | | |
|---|---|---|---|
| 3,475,437 | 10/1969 | Landgraf et al. | 548/468 |
| 3,801,594 | 4/1974 | Poletto et al. | 548/468 |
| 4,453,001 | 6/1984 | Brand et al. | 548/466 |
| 4,618,617 | 10/1986 | Yamamoto | 548/133 |
| 4,839,377 | 6/1989 | Bays et al. | 548/468 |
| 4,851,406 | 7/1989 | Mertens et al. | 548/133 |
| 4,870,085 | 9/1989 | Glaser et al. | 548/468 |
| 5,041,456 | 8/1991 | Baker et al. | 514/361 |
| 5,112,841 | 5/1992 | Matsubara et al. | 514/361 |
| 5,194,440 | 3/1993 | Pinbiro | 514/320 |
| 5,208,248 | 5/1993 | Baker et al. | 514/364 |

FOREIGN PATENT DOCUMENTS

| | | | |
|---|---|---|---|
| 313397 | 10/1987 | European Pat. Off. | 548/468 |
| 0301729 | 2/1989 | European Pat. Off. | 548/133 |
| 328200 | 2/1989 | European Pat. Off. | 548/468 |

OTHER PUBLICATIONS

A. L. Doenicke, et al, The Lancet, 1988, vol. 1, pp. 1309–1311.

*Primary Examiner*—Floyd D. Higel
*Attorney, Agent, or Firm*—Robert J. North; Melvin Winokur

[57] ABSTRACT

A class of indole-substituted five-membered heteroaromatic compounds are specific agonists of 5-$HT_1$-like receptors and are therefore useful in the treatment of clinical conditions, in particular migraine and associated disorders, for which a selective agonist of these receptors is indicated.

7 Claims, No Drawings

INDOLE-SUBSTITUTED FIVE-MEMBERED HETEROAROMATIC COMPOUNDS AS 5-HT₁ AGONISTS

CROSS-REFERENCE TO RELATED APPLICATIONS

The present case is a continuation of U.S. Ser. No. 07/641,422, filed Jan. 15, 1991, now abandoned.

The present invention relates to a class of indole-substituted five-membered heteroaromatic compounds which act on 5-hydroxytryptamine (5-HT) receptors, being specific agonists of so-called "5-HT₁-like" receptors. They are therefore useful in the treatment of clinical conditions for which a selective agonist of these receptors is indicated.

5-HT₁-like receptor agonists which exhibit selective vasoconstrictor activity have recently been described as being of use in the treatment of migraine (see, for example, A. Doenicke et al., The Lancet, 1988, Vol. 1, 1309-11). The compounds of the present invention, being specific 5-HT₁-like receptor agonists, are accordingly of particular use in the treatment of migraine and associated conditions, e.g. cluster headache, chronic paroxysmal hemicrania and headache associated with vascular disorders.

EP-A-0313397 describes a class of tryptamine derivatives substituted by a five-membered heteroaliphatic ring, which are stated to act as specific agonists of a particular type of "5-HT₁-like" receptor and thus to be effective therapeutic agents for the treatment of clinical conditions, particularly migraine, requiring this activity. However, EP-A-0313397 neither discloses nor suggests the heteroaromatic compounds provided by the present invention.

EP-A-0328200 describes a class of 5-membered heterocyclic compounds having at least one heteroatom, substituted on the heterocyclic ring by an azacyclic or azabicyclic ring system or an amino substituent. These compounds are stated to be useful in the treatment of psychotic disorders (e.g. schizophrenia and mania); anxiety; alcohol or drug withdrawal; pain, gastric stasis; gastric dysfunction; migraine, nausea and vomiting; and presenile and senile dementia. However, they have no action on the 5-HT₁-like receptors of which the heteroaromatic compounds of the present invention are specific agonists, and therefore elicit their effect by a different mechanism.

The present invention provides a compound of formula I, or a salt or prodrug thereof:

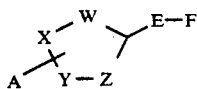
(I)

wherein the broken circle represents two non-adjacent double bonds in any position in the five-membered ring;

W, X, Y and Z independently represent oxygen, sulphur, nitrogen or carbon, provided that one of W, X, Y and Z represents oxygen or sulphur and at least one of W, X, Y and Z represents carbon;

A represents hydrogen, hydrocarbon, halogen, cyano, trifluoromethyl, nitro, $-OR^x$, $-OCOR^x$, $-ONR^xR^y$, $-SR^x$, $-NR^xR^y$, $-NR^xOR^y$, $-NR^zNR^xR^y$, $-NR^xCOR^y$, $-NR^xCO_2R^y$, $-NR^xSO_2R^y$, $-NR^zCVNR^xR^y$, $-COR^x$, $-CO_2R^x$ or $-CONR^xR^y$;

E represents a bond or a straight or branched alkylene chain containing from 1 to 4 carbon atoms;

F represents a group of formula

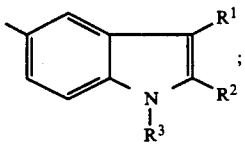

$R^1$ represents $-CH_2.CHR^4.NR^xR^y$ or a group of formula

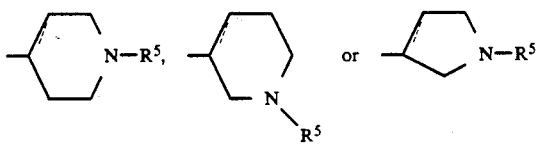

in which the broken line represents an optional chemical bond;

$R^2$, $R^3$, $R^4$ and $R^5$ independently represent hydrogen, $C_{1-6}$ alkyl, $C_{2-6}$ alkenyl or $C_{2-6}$ alkynyl;

$R^x$ and $R^y$ independently represent hydrogen or hydrocarbon, or $R^x$ and $R^y$ together represent a $C_{2-6}$ alkylene group;

$R^z$ represents hydrogen or hydrocarbon;

V represents oxygen, sulphur or a group of formula $=N.G$; and

G represents hydrocarbon or an electron-withdrawing group.

The present invention also provides compounds of formula I above wherein $R^x$, $R^y$ and $R^z$ independently represent hydrogen or hydrocarbon, and salts and prodrugs thereof.

For use in medicine, the salts of the compounds of formula I will be non-toxic pharmaceutically acceptable salts. Other salts may, however, be useful in the preparation of the compounds according to the invention or of their non-toxic pharmaceutically acceptable salts. Suitable pharmaceutically acceptable salts of the compounds of this invention include acid addition salts which may, for example, be formed by mixing a solution of the compound according to the invention with a solution of a pharmaceutically acceptable non-toxic acid such as hydrochloric acid, fumaric acid, maleic acid, succinic acid, acetic acid, citric acid, tartaric acid, carbonic acid or phosphoric acid. Furthermore, where the compounds of the invention carry an acidic moiety, suitable pharmaceutically acceptable salts thereof may include alkali metal salts, e.g. sodium or potassium salts; alkaline earth metal salts, e.g. calcium or magnesium salts; and salts formed with suitable organic ligands, e.g. quaternary ammonium salts.

The term "hydrocarbon" as used herein includes straight-chained, branched and cyclic groups, including heterocyclic groups, containing up to 18 carbon atoms, suitably up to 15 carbon atoms, and conveniently up to 12 carbon atoms. Suitable hydrocarbon groups include $C_{1-6}$ alkyl, $C_{2-6}$ alkenyl, $C_{2-6}$ alkynyl, $C_{3-7}$ cycloalkyl, $C_{3-7}$ cycloalkyl($C_{1-6}$)alkyl, aryl, aryl($C_{1-6}$)alkyl, $C_{3-7}$ heterocycloalkyl, $C_{3-7}$ heterocycloalkyl($C_{1-6}$)alkyl, heteroaryl and heteroaryl($C_{1-6}$)alkyl, Suitable alkyl groups include straight-chained and branched alkyl groups containing from 1 to 6 carbon atoms. Typical examples include methyl and ethyl groups, and straight-chained or branched propyl and butyl groups. Particular alkyl groups are methyl, ethyl and t-butyl.

Suitable alkenyl groups include straight-chained and branched alkenyl groups containing from 2 to 6 carbon atoms. Typical examples include vinyl and allyl groups.

Suitable alkynyl groups include straight-chained and branched alkynyl groups containing from 2 to 6 carbon atoms. Typical examples include ethynyl and propargyl groups.

Suitable cycloalkyl groups include groups containing from 3 to 7 carbon atoms. Particular cycloalkyl groups are cyclopropyl and cyclohexyl.

Suitable aryl groups include phenyl and naphthyl groups.

Particular aryl($C_{1-6}$)alkyl groups include benzyl, phenethyl and phenylpropyl.

Suitable heterocycloalkyl groups include azetidinyl, pyrrolidyl, piperidyl, piperazinyl and morpholinyl groups.

Suitable heteroaryl groups include pyridyl, quinolyl, isoquinolyl, pyridazinyl, pyrimidinyl, pyrazinyl, pyranyl, furyl, benzofuryl, dibenzofuryl, thienyl, benzthienyl, imidazolyl, oxadiazolyl and thiadiazolyl groups.

A particular heteroaryl($C_{1-6}$)alkyl group is pyridylmethyl.

The hydrocarbon group may in turn be optionally substituted by one or more groups selected from $C_{1-6}$ alkyl, adamantyl, phenyl, halogen, $C_{1-6}$ haloalkyl, $C_{1-6}$ aminoalkyl, trifluoromethyl, hydroxy, $C_{1-6}$ alkoxy, aryloxy, keto, $C_{1-3}$ alkylenedioxy, nitro, cyano, carboxy, $C_{2-6}$ alkoxycarbonyl, $C_{2-6}$ alkoxycarbonyl($C_{1-6}$)alkyl, $C_{2-6}$ alkylcarbonyloxy, arylcarbonyloxy, $C_{2-6}$ alkylcarbonyl, arylcarbonyl, $C_{1-6}$ alkylthio, $C_{1-6}$ alkylsulphinyl, $C_{1-6}$ alkylsulphonyl, arylsulphonyl, —NR$^v$R$^w$, —NR$^v$COR$^w$, —NR$^v$CO$_2$R$^w$, —NR$^v$SO$_2$R$^w$, —CH$_2$NR$^v$SO$_2$R$^w$, —NHCONR$^v$R$^w$, —CONR$^v$R$^w$, —SO$_2$NR$^v$R$^w$ and —CH$_2$SO$_2$NR$^v$R$^w$, in which R$^v$ and R$^w$ independently represent hydrogen, $C_{1-6}$ alkyl, aryl or aryl($C_{1-6}$)alkyl, or R$^v$ and R$^w$ together represent a $C_{2-6}$ alkylene group.

When R$^x$ and R$^y$, or R$^v$ and R$^w$, together represent a $C_{2-6}$ alkylene group, this group may be an ethylene, propylene, butylene, pentamethylene or hexamethylene group, preferably butylene or pentamethylene.

When the group G represents an electron-withdrawing group, this group is suitably cyano, nitro, —COR$^x$, —CO$_2$R$^x$ or —SO$_2$R$^x$, in which R$^x$ is as defined above.

The term "halogen" as used herein includes fluorine, chlorine, bromine and iodine, especially fluorine.

The present invention includes within its scope prodrugs of the compounds of formula I above. In general, such prodrugs will be functional derivatives of the compounds of formula I which are readily convertible in vivo into the required compound of formula I. Conventional procedures for the selection and preparation of suitable prodrug derivatives are described, for example, in "Design of Prodrugs", ed. H. Bundgaard, Elsevier, 1985.

Where the compounds according to the invention have at least one asymmetric centre, they may accordingly exist as enantiomers. Where the compounds according to the invention possess two or more asymmetric centres, they may additionally exist as diastereoisomers. It is to be understood that all such isomers and mixtures thereof are encompassed within the scope of the present invention.

The five-membered heteroaromatic ring in formula I containing the substituents W to Z may be, for example, a furan, thiophene, oxazole, thiazole, isoxazole, isothiazole, oxadiazole or thiadiazole ring, in particular a 1,2,4-oxadiazole, 1,3,4-oxadiazole, 1,2,4-thiadiazole, 1,3,4-thiadiazole, 1,3-oxazole or 1,3-thiazole ring. Preferably the ring is a 1,2,4-oxadiazole, 1,2,4-thiadiazole, 1,3-oxazole or 1,3-thiazole ring.

The alkylene chain E may be, for example, methylene, ethylene, 1-methylethylene, propylene or 2-methylpropylene. Alternatively, the group E may represent a single bond such that the indole moiety F in formula I is attached directly to the five-membered heteroaromatic ring.

Suitable values for the group A include $C_{1-6}$ alkyl, $C_{3-7}$ cycloalkyl, aryl, aryl($C_{1-6}$)alkyl, $C_{3-7}$ heterocycloalkyl or heteroaryl($C_{1-6}$)alkyl, any of which groups may be optionally substituted; and hydrogen, halogen, cyano, trifluoromethyl, nitro, $C_{1-6}$ alkoxy, $C_{1-6}$ alkylthio, —NR$^x$R$^y$ or —CONR$^x$R$^y$, in which R$^x$ and R$^y$ are as defined above. Examples of optional substituents on the group A suitably include phenyl, trifluoromethyl, $C_{1-6}$ alkoxy, $C_{2-6}$ alkoxycarbonyl, $C_{2-6}$ alkylcarbonyl, $C_{1-6}$ alkylsulphonyl, arylsulphonyl, amino, mono- or di($C_{1-6}$)alkylamino, $C_{2-6}$ alkylcarbonylamino, arylcarbonylamino, $C_{2-6}$ alkoxycarbonylamino, $C_{1-6}$ alkylsulphonylamino, arylsulphonylamino, $C_{1-6}$ alkylsulphonylaminomethyl, aminocarbonylamino, mono- or di($C_{1-6}$)alkylaminocarbonylamino, mono- or diarylaminocarbonylamino, pyrrolidylcarbonylamino, aminocarbonyl, mono- or di($C_{1-6}$)alkylaminocarbonyl, $C_{1-6}$ alkylaminosulphonyl, aminosulphonylmethyl, and mono- or di($C_{1-6}$)alkylaminosulphonylmethyl.

Particular values of A include methyl, methoxymethyl, aminomethyl, dimethylaminomethyl, acetylaminomethyl, benzoylaminomethyl, t-butoxycarbonylaminomethyl, methylsulphonylaminomethyl, phenylsulphonylaminomethyl, aminocarbonylmethyl, ethyl, aminoethyl, acetylaminoethyl, benzoylaminoethyl, methoxycarbonylaminoethyl, ethoxycarbonylaminoethyl, t-butoxycarbonylaminoethyl, methylsulphonylaminoethyl, aminocarbonylaminoethyl, methylaminocarbonylaminoethyl, t-butylaminocarbonylaminoethyl, phenylaminocarbonylaminoethyl, pyrrolidylcarbonylaminoethyl, cyclopropyl, phenyl, methylsulphonylaminophenyl, aminocarbonylphenyl, methylaminocarbonylphenyl, methylsulphonylaminomethylphenyl, aminosulphonylmethylphenyl, methylaminosulphonylmethylphenyl, dimethylaminosulphonylmethylphenyl, naphthyl, benzyl, diphenylmethyl, trifluoromethylbenzyl, methoxybenzyl, acetylaminobenzyl, methylsulphonylaminobenzyl, aminocarbonylaminobenzyl, aminocarbonylbenzyl, methylaminocarbonylbenzyl, methylsulphonylbenzyl, methylaminosulphonylbenzyl, phenethyl, phenylpropyl, acetylpiperazinyl, methoxycarbonylpiperazinyl, t-butoxycarbonylpiperazinyl, methylaminocarbonylpiperazinyl, methylsulphonylpiperazinyl, phenylsulphonylpiperazinyl, pyridylmethyl, methoxypyridylmethyl, amino, methylamino, benzylamino, dimethylamino, t-butoxycarbonylaminoethylamino, methylsulphonylaminoethylamino, aminocarbonyl, methylaminocarbonyl, azetidinylcarbonyl and pyrrolidylcarbonyl.

Representative values of $R^1$ include aminoethyl, N-methylaminoethyl, N,N-dimethylaminoethyl and 1- methyl-4-piperidyl. Preferably, R¹ represents aminoethyl or N,N-dimethylaminoethyl.

Suitably, the groups R² to R⁵ independently represent hydrogen or C₁₋₆ alkyl, in particular hydrogen or methyl.

A particular sub-class of compounds according to the invention is represented by the compounds of formula IIA, and salts and prodrugs thereof:

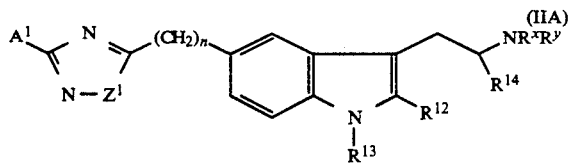

(IIA)

wherein
Z¹ represents oxygen or sulphur;
n is zero, 1, 2 or 3;
A¹ represents C₁₋₆ alkyl, C₂₋₆ alkenyl, C₂₋₆ alkynyl, C₃₋₇ cycloalkyl, aryl, aryl(C₁₋₆)alkyl, C₃₋₇ heterocycloalkyl, heteroaryl or heteroaryl(C₁₋₆)alkyl, any of which groups may be optionally substituted; or hydrogen, halogen, cyano, trifluoromethyl, nitro, C₁₋₆ alkoxy, C₁₋₆ alkylthio, —NRˣRʸ or —CONRˣRʸ;
R¹², R¹³ and R¹⁴ independently represent hydrogen, C₁₋₆ alkyl, C₂₋₆ alkenyl or C₂₋₆ alkynyl; and
Rˣ and Rʸ independently represent hydrogen or hydrocarbon, or Rˣ and Rʸ together represent a C₂₋₆ alkylene group.

Examples of optional substituents on the group A¹ suitably include phenyl, trifluoromethyl, C₁₋₆ alkoxy, C₂₋₆ alkoxycarbonyl, C₂₋₆ alkylcarbonyl, C₁₋₆ alkylsulphonyl, arylsulphonyl, amino, mono- or di(C₁₋₆)alkylamino, C₂₋₆ alkylcarbonylamino, arylcarbonylamino, C₂₋₆ alkoxycarbonylamino, C₁₋₆ alkylsulphonylamino, arylsulphonylamino, C₁₋₆ alkylsulphonylaminomethyl, aminocarbonylamino, mono- or di(C₁₋₆)alkylaminocarbonylamino, mono- or diarylaminocarbonylamino, pyrrolidylcarbonylamino, aminocarbonyl, mono- or di(C₁₋₆)alkylaminocarbonyl, C₁₋₆ alkylaminosulphonyl, aminosulphonylmethyl, and mono- or di(C₁₋₆)alkylaminosulphonylmethyl.

Particular values of A¹ with respect to formula IIA include methyl, methoxymethyl, aminomethyl, dimethylaminomethyl, acetylaminomethyl, benzoylaminomethyl, t-butoxycarbonylaminomethyl, methylsulphonylaminomethyl, phenylsulphonylaminomethyl, aminocarbonylmethyl, ethyl, aminoethyl, acetylaminoethyl, benzoylaminoethyl, methoxycarbonylaminoethyl, ethoxycarbonylaminoethyl, t-butoxycarbonylaminoethyl, methylsulphonylaminoethyl, aminocarbonylaminoethyl, methylaminocarbonylaminoethyl, t-butylaminocarbonylaminoethyl, phenylaminocarbonylaminoethyl, pyrrolidylcarbonylaminoethyl, cyclopropyl, phenyl, methylsulphonylaminophenyl, aminocarbonylphenyl, methylaminocarbonylphenyl, methylsulphonylaminomethylphenyl, aminosulphonylmethylphenyl, methylaminosulphonylmethylphenyl, dimethylaminosulphonylmethylphenyl, naphthyl, benzyl, diphenylmethyl, trifluoromethylbenzyl, methoxybenzyl, acetylaminobenzyl, methylsulphonylaminobenzyl, aminocarbonylaminobenzyl, aminocarbonylbenzyl, methylaminocarbonylbenzyl, methylsulphonylbenzyl, methylaminosulphonylbenzyl, phenethyl, phenylpropyl, acetylpiperazinyl, methoxycarbonylpiperazinyl, t-butoxycarbonylpiperazinyl, methylaminocarbonylpiperazinyl, methylsulphonylpiperazinyl, phenylsulphonylpiperazinyl, pyridylmethyl, methoxypyridylmethyl, amino, methylamino, benzylamino, dimethylamino, t-butoxycarbonylaminoethylamino, methylsulphonylaminoethylamino, aminocarbonyl, methylaminocarbonyl, azetidinylcarbonyl and pyrrolidylcarbonyl. In a preferred embodiment, A¹ represents amino.

Preferably, R¹², R¹³ and R¹⁴ each represents hydrogen. Preferred values of Rˣ and Rʸ with respect to formula IIA include hydrogen and methyl.

Another sub-class of compounds according to the invention is represented by the compounds of formula IIB, and salts and prodrugs thereof:

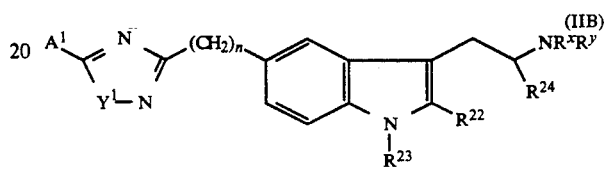

(IIB)

wherein
Y¹ represents oxygen or sulphur;
n is zero, 1, 2 or 3;
A¹ is as defined with reference to formula IIA above;
R²², R²³ and R²⁴ independently represent hydrogen, C₁₋₆ alkyl, C₂₋₆ alkenyl or C₂₋₆ alkynyl; and
Rˣ and Rʸ independently represent hydrogen or hydrocarbon, or Rˣ and Rʸ together represent a C₂₋₆ alkylene group.

Particular values of A¹ with respect to formula IIB include methyl and benzyl. Preferably, R²², R²³ and R²⁴ each represents hydrogen. Preferred values of Rˣ and Rʸ with respect to formula IIB include hydrogen and methyl.

A further sub-class of compounds according to the invention is represented by the compounds of formula IIC, and salts and prodrugs thereof:

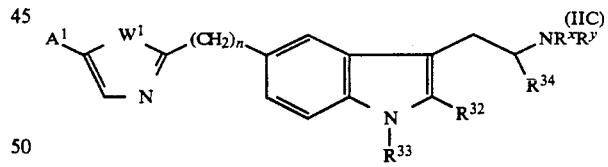

(IIC)

wherein
W¹ represents oxygen or sulphur;
n is zero, 1, 2 or 3;
A¹ is as defined with reference to formula IIA above;
R³², R³³ and R³⁴ independently represent hydrogen, C₁₋₆ alkyl, C₂₋₆ alkenyl or C₂₋₆ alkynyl; and
Rˣ and Rʸ independently represent hydrogen or hydrocarbon, or Rˣ and Rʸ together represent a C₂₋₆ alkylene group.

A particular value of A¹ with respect to formula IIC is methyl. Preferably, R³², R³³ and R³⁴ each represents hydrogen. Preferred values of Rˣ and Rʸ with respect to formula IIC include hydrogen and methyl.

A still further sub-class of compounds according to the invention is represented by the compounds of formula IID, and salts and prodrugs thereof:

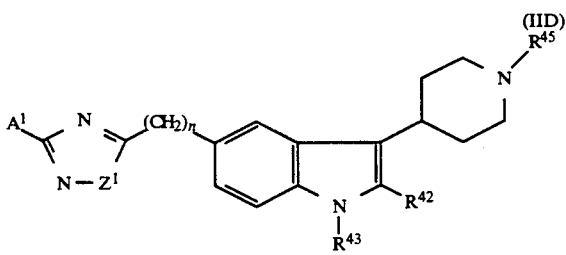

wherein $Z^1$ represents oxygen or sulphur;

n is zero, 1, 2 or 3;

$A^1$ is as defined with reference to formula IIA above;

$R^{42}$, $R^{43}$ and $R^{45}$ independently represent hydrogen, $C_{1-6}$ alkyl, $C_{2-6}$ alkenyl or $C_{2-6}$ alkynyl; and $R^x$ and $R^y$ independently represent hydrogen or hydrocarbon, or $R^x$ and $R^y$ together represent a $C_{2-6}$ alkylene group.

Particular values of $A^1$ with respect to formula IID include amino, and optionally substituted benzyl or pyridylmethyl, especially methylsulphonylaminobenzyl.

Preferably, $R^{42}$ and $R^{43}$ each represents hydrogen. Preferably, $R^{45}$ represents hydrogen or $C_{1-6}$ alkyl, especially methyl.

Specific compounds within the scope of the present invention include:

2-[5-(3-benzyl-1,2,4-oxadiazol-5-yl)-1H-indol-3-yl]ethylamine;

2-[5-(3-methyl-1,2,4-oxadiazol-5-yl)-1-H-indol-3-yl]ethylamine;

N,N-dimethyl-2-[5-(3-benzyl-1,2,4-oxadiazol-5-yl)-1H-indol-3-yl]ethylamine;

2-[5-(3-benzyl-1,2,4-oxadiazol-5-ylmethyl)-1H-indol-3-yl]ethylamine;

2-[5-(3-methyl-1,2,4-oxadiazol-5-ylmethyl)-1H-indol-3-yl]ethylamine;

2-[5-(3-amino-1,2,4-oxadiazol-5-ylmethyl)-1H-indol-3-yl]ethylamine;

2-[5-(3-phenyl-1,2,4-oxadiazol-5-ylmethyl)-1H-indol-3-yl]ethylamine;

2-[5-[3-(2-methoxybenzyl)-1,2,4-oxadiazol-5-ylmethyl]-1H-indol-3-yl]ethylamine;

N,N-dimethyl-2-[5-(3-benzyl-1,2,4-oxadiazol-5-ylmethyl)-1H-indol-3-yl]ethylamine;

2-[5-[2-(3-benzyl-1,2,4-oxadiazol-5-yl)ethyl]-1H-indol-3-yl]ethylamine;

N,N-dimethyl-2-[5-(3-methyl-1,2,4-oxadiazol-5-ylmethyl)-1H-indol-3-yl]ethylamine;

2-[5-(3-diphenylmethyl-1,2,4-oxadiazol-5-yl)-1H-indol-3-yl]ethylamine;

2-[5-(3-phenyl-1,2,4-oxadiazol-5-yl)-1H-indol-3-yl]ethylamine;

2-[5-[3-(2-methoxybenzyl)-1,2,4-oxadiazol-5-yl]-1H-indol-3-yl]ethylamine;

2-[5-[3-(3-benzyl-1,2,4-oxadiazol-5-yl)propyl]-1H-indol-3-yl]ethylamine;

2-[5-(3-phenethyl-1,2,4-oxadiazol-5-yl)-1H-indol-3-yl]ethylamine;

2-[5-(5-benzyl-1,2,4-oxadiazol-3-yl)-1H-indol-3-yl]ethylamine;

2-[5-(5-benzyl-1,2,4-oxadiazol-3-ylmethyl)-1H-indol-3-yl]ethylamine;

N,N-dimethyl-2-[5-[3-(2-methoxybenzyl)-1,2,4-oxadiazol-5-yl]-1H-indol-3-yl]ethylamine;

N,N-dimethyl-2-[5-[2-(3-benzyl-1,2,4-oxadiazol-5-yl)ethyl]-1H-indol-3-yl]ethylamine;

2-[5-[3-(1-naphthyl)-1,2,4-oxadiazol-5-ylmethyl]-1H-indol-3-yl]ethylamine;

2-[5-[3-(3-methyl-1,2,4-oxadiazol-5-yl)propyl]-1H-indol-3-yl]ethylamine;

2-[5-[3-(3-cyclopropyl-1,2,4-oxadiazol-5-yl)propyl]-1H-indol-3-yl]ethylamine;

2-[5-[3-(3-methoxybenzyl)-1,2,4-oxadiazol-5-yl]-1H-indol-3-yl]ethylamine;

2-[5-[3-(4-methoxybenzyl)-1,2,4-oxadiazol-5-yl]-1H-indol-3-yl]ethylamine;

2-[5-[3-(4-acetylaminobenzyl)-1,2,4-oxadiazol-5-yl]-1H-indol-3-yl]ethylamine;

2-[5-[3-(4-methylsulphonylaminobenzyl)-1,2,4-oxadiazol-5-yl]-1H-indol-3-yl]ethylamine;

2-[5-[3-(3-phenylpropyl)-1,2,4-oxadiazol-5-yl]-1H-indol-3-yl]ethylamine;

2-[5-(3-cyclopropyl-1,2,4-oxadiazol-5-yl)-1H-indol-3-yl]ethylamine;

2-[5-(3-ethyl-1,2,4-oxadiazol-5-yl)-1H-indol-3-yl]ethylamine;

2-[5-[3-(4-trifluoromethylbenzyl)-1,2,4-oxadiazol-5-yl]-1H-indol-3-yl]ethylamine;

N,N-dimethyl-2-[5-[3-(4-acetylaminobenzyl)-1,2,4-oxadiazol-5-yl]-1H-indol-3-yl]ethylamine;

N,N-dimethyl-2-[5-[3-(4-methylsulphonylaminobenzyl)-1,2,4-oxadiazol-5-yl]-1H-indol-3-yl]ethylamine;

N,N-dimethyl-2-[5-(3-amino-1,2,4-oxadiazol-5-ylmethyl)-1H-indol-3-yl]ethylamine;

2-[5-[2-(3-amino-1,2,4-oxadiazol-5-yl)ethyl]-1H-indol-3-yl]ethylamine;

2-[5-[2-(3-dimethylamino-1,2,4-oxadiazol-5-yl)ethyl]-1H-indol-3-yl]ethylamine;

2-[5-(5-methyl-1,2,4-oxadiazol-3-yl)-1H-indol-3-yl]ethylamine;

2-[5-(5-methyl-1,2,4-oxadiazol-3-ylmethyl)-1H-indol-3-yl]ethylamine;

N,N-dimethyl-2-[5-(5-benzyl-1,2,4-oxadiazol-3-ylmethyl)-1H-indol-3-yl]ethylamine;

2-[5-(3-methoxymethyl-1,2,4-oxadiazol-5-yl)-1H-indol-3-yl]ethylamine;

2-[5-[3-(4-methylaminocarbonylbenzyl)-1,2,4-oxadiazol-5-yl]-1H-indol-3-yl]ethylamine;

2-[5-[3-(4-methylaminocarbonylphenyl)-1,2,4-oxadiazol-5-yl]-1H-indol-3-yl]ethylamine;

2-[5-[3-(4-methylaminosulphonylbenzyl)-1,2,4-oxadiazol-5-yl]-1H-indol-3-yl]ethylamine;

2-[5-[3-(4-methylsulphonylbenzyl)-1,2,4-oxadiazol-5-yl]-1H-indol-3-yl]ethylamine;

2-[5-[3-(3-methylsulphonylaminobenzyl)-1,2,4-oxadiazol-5-yl]-1H-indol-3-yl]ethylamine;

2-[5-[3-(4-aminocarbonylaminobenzyl)-1,2,4-oxadiazol-5-yl]-1H-indol-3-yl]ethylamine;

2-[5-(3-amino-1,2,4-oxadiazol-5-yl)-1H-indol-3-yl]ethylamine;

2-[5-(3-acetylaminomethyl-1,2,4-oxadiazol-5-yl)-1H-indol-3-yl]ethylamine;

2-[5-[3-(2-acetylaminoethyl)-1,2,4-oxadiazol-5-yl]-1H-indol-3-yl]ethylamine;

2-[5-(3-aminomethyl-1,2,4-oxadiazol-5-yl)-1H-indol-3-yl]ethylamine;

N,N-dimethyl-2-[5-(3-amino-1,2,4-oxadiazol-5-yl)-1H-indol-3-yl]ethylamine;

N,N-dimethyl-2-[5-(3-acetylaminomethyl-1,2,4-oxadiazol-5-yl)-1H-indol-3-yl]ethylamine;

N,N-dimethyl-2-[5-[3-(2-acetylaminoethyl)-1,2,4-oxadiazol-5-yl]-1H-indol-3-yl]ethylamine;

N,N-dimethyl-2-[5-[3-(4-aminocarbonylaminobenzyl)-1,2,4-oxadiazol-5-yl]-1H-indol-3-yl]ethylamine;

N,N-dimethyl-2-[5-[3-(2-(t-butoxycarbonylamino)ethyl)-1,2,4-oxadiazol-5-yl]-1H-indol-3-yl]ethylamine;

N,N-dimethyl-2-[5-[3-(4-methylaminocarbonylbenzyl)-1,2,4-oxadiazol-5-yl]-1H-indol-3-yl]ethylamine;

N,N-dimethyl-2-[5-[3-(2-aminoethyl)-1,2,4-oxadiazol-5-yl]-1H-indol-3-yl]ethylamine;

N,N-dimethyl-2-[5-[3-(2-methylsulphonylaminoethyl)-1,2,4-oxadiazol-5-yl]-1H-indol-3-yl]ethylamine;

N,N-dimethyl-2-[5-[3-(2-aminocarbonylaminoethyl)-1,2,4-oxadiazol-5-yl]-1H-indol-3-yl]ethylamine;

N,N-dimethyl-2-[5-[3-(2-methylaminocarbonylaminoethyl)-1,2,4-oxadiazol-5-yl]-1H-indol-3-yl]ethylamine;

N,N-dimethyl-2-[5-[3-(2-methylaminocarbonylaminoethyl)-1,2,4-oxadiazol-5-yl]-1H-indol-3-yl]ethylamine;

N,N-dimethyl-2-[5-[3-(2-methoxycarbonylaminoethyl)-1,2,4-oxadiazol-5-yl]-1H-indol-3-yl]ethylamine;

N,N-dimethyl-2-[5-[3-(2-ethoxycarbonylaminoethyl)1,2,4-oxadiazol-5-yl]-1H-indol-3-yl]ethylamine;

N,N-dimethyl-2-[5-[2-(3-amino-1,2,4-oxadiazol-5-yl)ethyl]-1H-indol-3-yl]ethylamine;

N,N-dimethyl-2-[5-(3-methylamino-1,2,4-oxadiazol-5-ylmethyl)-1H-indol-3-yl]ethylamine;

N,N-dimethyl-2-[5-[3-(4-aminocarbonylbenzyl)-1,2,4-oxadiazol-5-ylmethyl]-1H-indol-3-yl]ethylamine;

N,N-dimethyl-2-[5-[3-(4-acetylaminobenzyl)-1,2,4-oxadiazol-5-ylmethyl]-1H-indol-3-yl]ethylamine;

N,N-dimethyl-2-[5-[3-(4-methylaminosulphonylbenzyl)-1,2,4-oxadiazol-5-ylmethyl]-1H-indol-3-yl]ethylamine;

N,N-dimethyl-2-[5-[3-(4-aminocarbonylaminobenzyl)-1,2,4-oxadiazol-5-ylmethyl]-1H-indol-3-yl]ethylamine;

N,N-dimethyl-2-[5-[3-(4-methylsulphonylaminobenzyl)-1,2,4-oxadiazol-5-ylmethyl]-1H-indol-3-yl]ethylamine;

N,N-dimethyl-2-[5-[3-(4-methylaminocarbonylphenyl)-1,2,4-oxadiazol-5-ylmethyl]-1H-indol-3-yl]ethylamine;

N,N-dimethyl-2-[5-[3-(3-acetylaminomethyl-1,2,4-oxadiazol-5-ylmethyl)-1H-indol-3-yl]ethylamine;

N,N-dimethyl-2-[5-(3-methylsulphonylaminomethyl-1,2,4-oxadiazol-5-ylmethyl)-1H-indol-3-yl]ethylamine;

N,N-dimethyl-2-[5-(3-aminocarbonylmethyl-1,2,4-oxadiazol-5-ylmethyl)-1H-indol-3-yl]ethylamine;

N,N-dimethyl-2-[5-[3-(3-methylsulphonylaminobenzyl)-1,2,4-oxadiazol-5-ylmethyl]-1H-indol-3-yl]ethylamine;

N,N-dimethyl-2-[5-[3-(3-acetylaminobenzyl)-1,2,4-oxadiazol-5-ylmethyl]-1H-indol-3-yl]ethylamine;

N,N-dimethyl-2-[5-[3-(4-aminocarbonylphenyl)-1,2,4-oxadiazol-5-ylmethyl]-1H-indol-3-yl]ethylamine;

N,N-dimethyl-2-[5-[3-(3-aminocarbonylphenyl)-1,2,4-oxadiazol-5-ylmethyl]-1H-indol-3-yl]ethylamine;

N,N-dimethyl-2-[5-[3-(4-methylsulphonylaminophenyl)-1,2,4-oxadiazol-5-ylmethyl]-1H-indol-3-yl]ethylamine;

N,N-dimethyl-2-[5-[3-(4-methylaminosulphonylmethylphenyl)-1,2,4-oxadiazol-5-ylmethyl]-1H-indol-3-yl]ethylamine;

N,N-dimethyl-2-[5-[3-(3-methylaminosulphonylmethylphenyl)-1,2,4-oxadiazol-5-ylmethyl]-1H-indol-3-yl]ethylamine;

N,N-dimethyl-2-[5-[3-(4-aminosulphonylmethylphenyl)-1,2,4-oxadiazol-5-ylmethyl]-1H-indol-3-yl]ethylamine;

N,N-dimethyl-2-[5-[3-(4-dimethylaminosulphonylmethylphenyl)-1,2,4-oxadiazol-5-ylmethyl]-1H-indol-3-yl]ethylamine;

N,N-dimethyl-2-[5-[3-(t-butoxycarbonylamino)methyl-1,2,4-oxadiazol-5-ylmethyl]-1H-indol-3-yl]ethylamine;

N,N-dimethyl-2-[5-[3-(2-(t-butoxycarbonylamino)ethyl)-1,2,4-oxadiazol-5-ylmethyl]-1H-indol-3-yl]ethylamine;

N,N-dimethyl-2-[5-(3-aminomethyl-1,2,4-oxadiazol-5-ylmethyl)-1H-indol-3-yl]ethylamine;

N,N-dimethyl-2-[5-(3-methoxycarbonylaminomethyl-1,2,4-oxadiazol-5-ylmethyl)-1H-indol-3-yl]ethylamine;

N,N-dimethyl-2-[5-(3-dimethylaminomethyl-1,2,4-oxadiazol-5-ylmethyl)-1H-indol-3-yl]ethylamine;

N,N-dimethyl-2-[5-[3-(2-methylsulphonylaminoethyl)-1,2,4-oxadiazol-5-ylmethyl]-1H-indol-3-yl]ethylamine;

N,N-dimethyl-2-[5-[3-(2-ethoxycarbonylaminoethyl)-1,2,4-oxadiazol-5-ylmethyl]-1H-indol-3-yl]ethylamine;

N,N-dimethyl-2-[5-(3-benzoylaminomethyl-1,2,4-oxadiazol-5-ylmethyl)-1H-indol-3-yl]ethylamine;

N,N-dimethyl-2-[5-[3-(2-benzoylaminoethyl)-1,2,4-oxadiazol-5-ylmethyl]-1H-indol-3-yl]ethylamine;

N,N-dimethyl-2-[5-[3-(2-phenylaminocarbonylaminoethyl)-1,2,4-oxadiazol-5-ylmethyl]-1H-indol-3-yl]ethylamine;

N,N-dimethyl-2-[5-[3-(2-(t-butylaminocarbonylamino)ethyl)-1,2,4-oxadiazol-5-ylmethyl]-1H-indol-3-yl]ethylamine;

N-methyl-2-[5-(3-amino-1,2,4-oxadiazol-5-ylmethyl)-1H-indol-3-yl]ethylamine;

N,N-dimethyl-2-[5-[3-(4-(t-butoxycarbonyl)piperazin-1-yl)-1,2,4-oxadiazol-5-ylmethyl]-1H-indol-3-yl]ethylamine;

N,N-dimethyl-2-[5-[3-(4-methylsulphonylpiperazin-1-yl)-1,2,4-oxadiazol-5-ylmethyl]-1H-indol-3-yl]ethylamine;

N,N-dimethyl-2-[5-[3-(4-methoxycarbonylpiperazin-1-yl)-1,2,4-oxadiazol-5-ylmethyl]-1H-indol-3-yl]ethylamine;

N,N-dimethyl-2-[5-[3-(4-methylaminocarbonylpiperazin-1-yl)-1,2,4-oxadiazol-5-ylmethyl]-1H-indol-3-yl]ethylamine;

N,N-dimethyl-2-[5-[3-(4-acetylpiperazin-1-yl)-1,2,4-oxadiazol-5-ylmethyl]-1H-indol-3-yl]ethylamine;

N,N-dimethyl-2-[5-[3-(4-methylsulphonylaminomethylphenyl)-1,2,4-oxadiazol-5-yl-methyl]-1H-indol-3-yl]ethylamine;

N,N-dimethyl-2-[5-(3-phenylsulphonylaminomethyl-1,2,4-oxadiazol-5-ylmethyl)-1H-indol-3-yl]ethylamine;

N,N-dimethyl-2-[5-(3-benzylamino-1,2,4-oxadiazol-5-ylmethyl)-1H-indol-3-yl]ethylamine;

N,N-dimethyl-2-[5-[3-(3-pyridyl)methyl-1,2,4-oxadiazol-5-ylmethyl]-1H-indol-3-yl]ethylamine;

N,N-dimethyl-2-[5-[3-(2-methoxypyrid-5-yl)methyl-1,2,4-oxadiazol-5-ylmethyl]-1H-indol-3-yl]ethylamine;

2-[5-[3-(4-acetylaminobenzyl)-1,2,4-oxadiazol-5-ylmethyl]-1H-indol-3-yl]ethylamine;

2-[5-[3-(4-methylsulphonylaminobenzyl)-1,2,4-oxadiazol-5-ylmethyl]-1H-indol-3-yl]ethylamine;

2-[5-[2-[3-(4-acetylaminobenzyl)-1,2,4-oxadiazol-5-yl]ethyl]-1H-indol-3-yl]ethylamine;

2-[5-[2-[3-(4-methoxybenzyl)-1,2,4-oxadiazol-5-yl]e-thyl]-1H-indol-3-yl]ethylamine;
N,N-dimethyl-2-[5-(5-methyl-1,3-oxazol-2-yl)-1H-indol-3-yl]ethylamine;
N,N-dimethyl-2-[5-[2-(5-methyl-1,3-oxazol-2-yl)ethyl]-1H-indol-3-yl]ethylamine;
1-methyl-4-[5-(3-amino-1,2,4-oxadiazol-5-yl)-1H-indol-3-yl]piperidine;
1-methyl-4-[5-(3-amino-1,2,4-oxadiazol-5-ylmethyl)-1H-indol-3-yl]piperidine;
1-methyl-4-[5-[3-(4-methylsulphonylaminobenzyl)-1,2,4-oxadiazol-5-ylmethyl]-1H-indol-3-yl]piperidine;
1-methyl-4-[5-[3-(3-pyridyl)methyl-1,2,4-oxadiazol-5-ylmethyl]-1H-indol-3-yl]piperidine;
N,N-dimethyl-2-[5-[3-(4-pyridyl)methyl-1,2,4-oxadiazol-5-ylmethyl]-1H-indol-3-yl]ethylamine;
N,N-dimethyl-2-[5-[3-(2-(t-butoxycarbonylamino)ethyl)amino-1,2,4-oxadiazol-5-ylmethyl]-1H-indol-3-yl]ethylamine;
2-[5-(3-aminocarbonyl-1,2,4-oxadiazol-5-ylmethyl)-1H-indol-3-yl]ethylamine;
2-[5-(3-methylaminocarbonyl-1,2,4-oxadiazol-5-ylmethyl)1H-indol-3-yl]ethylamine;
2-[5-[3-(pyrrolid-1-yl)carbonyl-1,2,4-oxadiazol-5-ylmethyl]-1H-indol-3-yl]ethylamine;
2-[5-[3-(azetidin-1-yl)carbonyl-1,2,4-oxadiazol-5-ylmethyl]1H-indol-3-yl]ethylamine;
N,N-dimethyl-2-[5-[3-(4-phenylsulphonylpiperazin-1-yl)1,2,4-oxadiazol-5-ylmethyl]-1H-indol-3-yl]ethylamine;
N,N-dimethyl-2-[5-[3-(2-(pyrrolid-1-ylcarbonylamino)ethyl)-1,2,4-oxadiazol-5-ylmethyl]-1H-indol-3-yl]ethylamine;
N,N-dimethyl-2-[5-[3-(2-methylsulphonylaminoethyl)amino-1,2,4-oxadiazol-5-ylmethyl]-1H-indol-3-yl]ethylamine;
N,N-dimethyl-2-[5-(3-amino-1,4-thiadiazol-5-ylmethyl)-1H-indol-3-yl]ethylamine;
and salts and prodrugs thereof.

The invention also provides pharmaceutical compositions comprising one or more compounds of this invention in association with a pharmaceutically acceptable carrier. Preferably these compositions are in unit dosage forms such as tablets, pills, capsules, powders, granules, sterile parenteral solutions or suspensions, or suppositories, for oral, parenteral or rectal administration. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

In the treatment of migraine, a suitable dosage level is about 0.01 to 250 mg/kg per day, preferably about 0.05 to 100 mg/kg per day, and especially about 0.05 to 5 mg/kg per day. The compounds may be administered on a regimen of 1 to 4 times per day.

The oxadiazole compounds of this invention may be prepared by a process which comprises reacting a reactive derivative of a carboxylic acid of formula $R^c$—$CO_2H$ with a compound either of formula III or of formula IV, or a salt thereof:

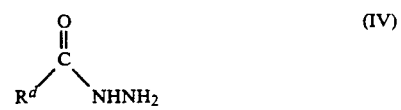

wherein one of $R^c$ and $R^d$ is a group of formula A, and the other is a group of formula —E—F, as defined with reference to formula I above.

Suitable reactive derivatives of the acid $R^c$—$CO_2H$ include esters, for example $C_{1-4}$ alkyl esters; thioesters, for example pyridylthioesters; acid anhydrides, for example $(R^cCO)_2O$; acid halides, for example acid chlorides; orthoesters; and primary, secondary and tertiary amides.

A preferred reactive derivative of the acid $R^c$—$CO_2H$ is the iminoether derivative of formula V:

where R is $C_{1-4}$ alkyl.

When the compound of formula III is employed the product of the reaction is a 1,2,4-oxadiazole. It will be appreciated that the compound III can also be considered as the alternative tautomeric form IIIA:

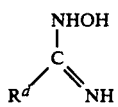

wherein $R^d$ is as defined above.

A 3-substituted-1,2,4-oxadiazol-5-yl compound is produced if $R^c$ represents a group —E—F and $R^d$ in formula III represents a group A; whereas a 5-substituted-1,2,4-oxadiazol-3-yl compound is produced by the process of this invention when $R^c$ represents a group A and $R^d$ represents a group —E—F. A preferred reactive derivative of the acid $R^c$—$CO_2H$ in this case is a $C_{1-4}$ alkyl ester. The reaction is conveniently carried out in the presence of a strong base, e.g. sodium hydride, using a suitable solvent, for example tetrahydrofuran, dimethylformamide or a lower alkanol such as ethanol, propanol or isopropanol, at about 20° C. to 100° C. for about 1 to 6 hours.

When the compound of formula IV is employed, the product of the process of this invention is a 1,3,4-oxadiazole. In this case, a preferred reactive derivative of the acid $R^c$—$CO_2H$ is an orthoester of formula $R^cC(OR^p)_3$ where $R^p$ represents $C_{1-3}$ alkyl. The process is conveniently effected by heating the hydrazide IV with the orthoester in a solvent such as methanol at reflux temperature for about 2 to 8 hours. An intermediate of formula $R^d.CO.NH.N{=}C(R^c)OR^p$ may be isolated by evaporation of the solvent. The intermediate is then treated with a strong base such as potassium t-butoxide or 1,8-diazabicyclo[5.4.0]undec-7-ene, in butanol for about 10 to 24 hours at about 90° C. to 150° C.

The reactive derivative of a carboxylic acid of formula $R^c$—$CO_2H$ or the compound of formula III or IV, wherein $R^c$ or $R^d$ represents a group of formula —E—F, may be prepared by reacting a compound of formula VI:

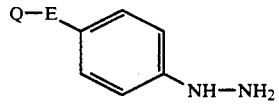
(VI)

wherein Q represents a reactive carboxylate moiety, or a group of formula —C(NOH)$NH_2$ or —CONH$NH_2$ or a protected derivative thereof or precursor thereto; and E is as defined above; with a compound of formula VII or a carbonyl-protected form thereof:

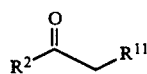
(VII)

wherein $R^2$ is as defined above and $R^{11}$ corresponds to the group $R^1$ as defined above or represents a group of formula —$CH_2$.$CHR^4$D, in which $R^4$ is as defined above and D represents a readily displaceable group; followed, where required, by N-alkylation by standard methods to introduce the moiety $R^3$.

When the moiety Q in the compounds of formula VI represents a precursor to a group of formula —C(-NOH)$NH_2$ or —CONH$NH_2$, this group is suitably a nitrile group.

Suitable carbonyl-protected forms of the compounds of formula VII include the dimethyl acetal or ketal derivatives.

The readily displaceable group D in the compounds of formula VII suitably represents a halogen group, preferably chlorine. When the moiety $R^{11}$ in the compounds of formula VII is a group of formula —$CH_2$.$CHR^4$D, the substituent D is displaced in situ under the prevailing reaction conditions to afford a final product of formula I wherein $R^1$ represents a group of formula —$CH_2$.$CHR^4$.$NH_2$. The terminal amino group can subsequently, if desired, be further elaborated using techniques known from the art to give a compound of formula I wherein $R^1$ represents the required group of formula —$CH_2$.$CHR^4$.$NR^xR^y$.

The reaction of compounds VI and VII may be carried out in a single step (Fischer indole synthesis) or by an initial non-cyclising step at a lower temperature to give a compound of formula VIII:

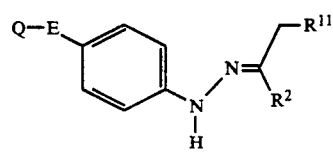
(VIII)

wherein Q, E, $R^2$ and $R^{11}$ are as defined above; followed by cyclisation using a suitable reagent, such as a polyphosphate ester, to give a compound of formula Q—E—F.

The hydrazines of formula VI may be prepared from the corresponding anilines of formula IX:

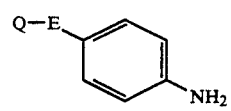
(IX)

wherein Q and E are as defined above; by diazotisation followed by reduction. Diazotisation is typically carried out using sodium nitrite/conc. HCl and the resulting diazo product reduced in situ using, for example, tin(II) chloride/conc. HCl.

The anilines of formula IX may be prepared by reduction of the corresponding nitro compounds of formula X:

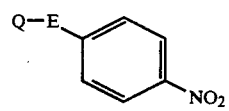
(X)

wherein Q and E are as defined above; typically by catalytic hydrogenation or using tin(II) chloride.

Where they are not commercially available, the nitro compounds of formula X may be synthesized by standard methods well known to those skilled in the art.

The 1,2,4-thiadiazoles of formula I may be prepared by a process which comprises the cyclisation of a compound of formula XI:

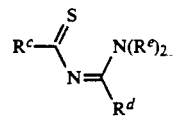
(XI)

wherein $R^c$ and $R^d$ are as defined above, and $R^e$ is hydrogen or an alkyl group.

Cyclisation of compound XI can be achieved using an aminating agent such as hydroxylamine-O-sulphonic acid in a lower alkanol such as methanol, ethanol or propanol, in the presence of pyridine, at between −20° C. and 50° C. for about 1-6 hours.

Cyclisation of compounds of formula XI in which $R^e$ is hydrogen may also be achieved by use of an oxidising agent such as bromine, iodine, hydrogen peroxide or nitric acid.

The compounds of formula XI above may be prepared by the processes described in *Comprehensive Heterocyclic Chemistry*, ed. A. R. Katritzky and C. W. Rees, Pergamon Press, 1984, Vol. 6, p. 496, or by methods analogous thereto.

The 1,2,4-thiadiazoles may also be prepared by cycloaddition of a nitrile sulphide $R^c$—C≡N$^+$—S$^-$ with a nitrile of formula $R^d$—CN where $R^c$ and $R^d$ are as defined above.

1,3,4-Thiadiazoles of this invention may be prepared by dehydration of a thiosemicarbazide of formula $R^c$CSNHNHCONR$^s$R$^t$, where $R^c$ is as defined above and $R^s$ and $R^t$ are hydrogen or an alkyl group, with a dehydrating agent such as sulphuric acid, polyphosphoric acid or methanesulphonic acid; followed by attachment of the $R^d$ group by conventional means.

1,2,5-Thiadiazoles of this invention may be prepared by reacting a diamine of the type

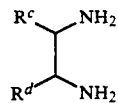

where $R^c$ and $R^d$ are as defined above, with a sulphur chloride such as thionyl chloride or sulphur dichloride.

The oxazoles and thiazoles of this invention may be prepared by reaction of an amide or thioamide of formula XII with a α-haloketone of formula XIII:

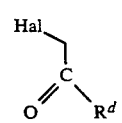

(XII)

(XIII)

wherein U is oxygen or sulphur, Hal represents halogen, and $R^c$ and $R^d$ are as defined above. The conditions for this reaction are as described in Synthesis, 1975, 389.

Furans possessing a 2,5-substitution pattern may, for example, be prepared by treating a compound of formula XIV:

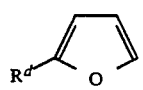

(XIV)

wherein $R^d$ is as previously defined; with a reagent capable of generating an anion thereof by abstraction of the proton adjacent to the oxygen atom; and subsequently reacting the anionic species thereby obtained with an electrophilic species capable of providing the moiety $R^c$, wherein $R^c$ is as previously defined.

The reagent capable of generating an anion of the compound of formula XIV by abstraction of the proton adjacent to the oxygen atom is suitably an alkyl lithium, e.g. n-butyllithium.

The electrophilic species capable of providing the moiety $R^c$ is suitably a carbonyl-containing compound or a compound of formula $R^c$—L, in which L represents a suitable leaving group such as halogen atom, e.g. chlorine or bromine. In the former case, the compound obtained from reaction of the carbonyl compound with the anion derived from compound XIV will contain a hydroxy moiety as part of the resulting $R^c$ group. This hydroxy moiety may, if desired, be retained intact, or may be removed by standard procedures, for example elimination with POCl$_3$ followed by hydrogenation.

Illustrative experimental details for performing the above process are, for example, described in *J. Med. Chem.*, 1990, 33, 1128.

The intermediate of formula XIV may be prepared by conventional methods, for example:

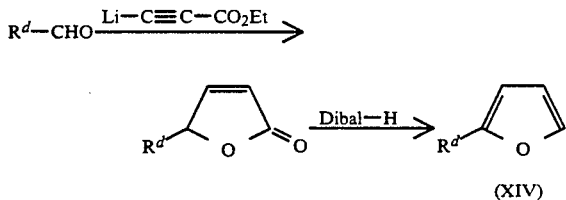

(XIV)

wherein $R^d$ is as defined above.

In an alternative process, the compounds according to the invention may be prepared by a method which comprises reacting a compound of formula XV:

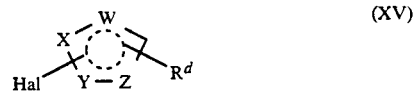

(XV)

with a reagent which provides an anion $^-R^c$, where W, X, Y, Z, $R^c$ and $R^d$ are as previously defined and Hal represents halogen.

Compound XV may be prepared by conventional procedures known from the art. For example, if compound XV is a 1,2,4-thiadiazole, this compound may be prepared by the general method described in *Chem. Ber.*, 1957, 90, 182.

Reagents which may provide the anion $^-R^c$ include Grignard reagents $R^c$MgHal (where Hal=halogen); organocuprate reagents such as LiR$^c_2$Cu; organolithium reagents $R^c$Li; or compounds which stabilise the anion by means of an adjacent activating group such as an ester or enolisable ketone function. In this case, the adjacent ester or ketone function may be retained after the process is complete, or may be removed. For example, an ester moiety may be hydrolysed and decarboxylated.

In a further process, the compounds according to the invention may be prepared by a method which comprises reacting a compound of formula XVI:

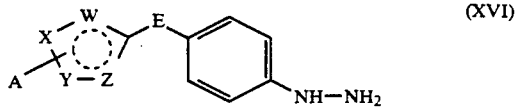

(XVI)

wherein W, X, Y, Z, A and E are as defined above; with a compound of formula VII as defined above, or a carbonyl-protected form thereof, e.g. the dimethyl acetal or ketal; followed, where required, by N-alkylation by standard methods to introduce the moiety $R^3$.

As with that between compounds VI and VII, the reaction between compounds XVI and VII may be carried out in a single step (Fischer indole synthesis) or by an initial non-cyclising step at a lower temperature to give a compound of formula XVII:

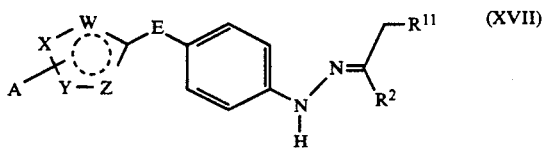

(XVII)

wherein W, X, Y, Z, A, E, $R^2$ and $R^{11}$ are as defined above; followed by cyclisation using a suitable reagent, e.g. a polyphosphate ester.

The hydrazines of formula XVI may be prepared from the corresponding anilines of formula XVIII:

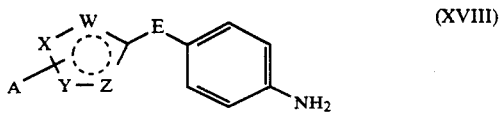

(XVIII)

wherein W, X, Y, Z, A and E are as defined above; by methods analogous to those described above with reference to the compounds of formula IX.

The anilines of formula XVIII may be prepared from those of formula IX above by appropriate modification of the moiety Q using, for example, methods analogous to those described above with reference to the compounds of formulae III and IV. Thus, for example, when Q in the compounds of formula IX represents a group of formula —C(NOH)NH$_2$ or —CONHNH$_2$, the compounds of formula XVIII may be prepared therefrom by reaction with a reactive derivative of a carboxylic acid of formula A—CO$_2$H, where A is as defined previously. Alternatively, when Q in the compounds of formula IX represents a reactive carboxylate moiety, the compounds of formula XVIII may be prepared therefrom by reaction with a compound of formula A—C(NOH)NH$_2$ or A—CONHNH$_2$.

It will be appreciated that any compound of formula I initially obtained from any of the above processes may, where appropriate, subsequently be elaborated into a further compound of formula I by techniques known from the art. In particular, a compound of formula I wherein $R^3$ is hydrogen initially obtained may be converted into a compound of formula I wherein $R^3$ represents $C_{1-6}$ alkyl, $C_{2-6}$ alkenyl or $C_{2-6}$ alkynyl by standard techniques such as alkylation, for example by treatment with an alkyl iodide, e.g. methyl iodide, typically under basic conditions, e.g. sodium hydride in dimethylformamide. Similarly, a compound of formula I wherein $R^1$ represents a group of formula —CH$_2$.CHR$^4$.NH$_2$ initially obtained may be converted into a compound of formula I wherein $R^1$ represents a group of formula —CH$_2$.CHR$^4$.NR$^x$R$^y$ in which R$^x$ and R$^y$ are as defined above with the exception of hydrogen, for example by conventional N-alkylation or N-arylation techniques, e.g. by treatment with the appropriate aldehyde in the presence of a reducing agent such as sodium cyanoborohydride.

Where the above-described processes for the preparation of the compounds according to the invention give rise to mixtures of stereoisomers, these isomers may be separated by conventional techniques such as preparative chromatography.

The novel compounds may be prepared in racemic form, or individual enantiomers may be prepared either by enantiospecific synthesis or by resolution. The novel compounds may, for example, be resolved into their component enantiomers by standard techniques, such as the formation of diastereomeric pairs by salt formation with an optically active acid, such as (—)-di-p-toluoyl-d-tartaric acid and/or (+)-di-p-toluoyl-l-tartaric acid followed by fractional crystallization and regeneration of the free base. The novel compounds may also be resolved by formation of diastereomeric esters or amides, followed by chromatographic separation and removal of the chiral auxiliary.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene, *Protective Groups in Organic Synthesis*, John Wiley & Sons, 1981. The protecting groups may be removed at a convenient subsequent stage using methods known from the art.

The following Examples illustrate the preparation of compounds according to the invention.

The ability of test compounds to bind to 5-HT$_1$-like receptors was measured in membranes prepared from pig caudate using the procedure described in *J. Neurosci.*, 1987, 7, 894. Binding was determined using 2 nM 5-hydroxytryptamine creatinine sulphate, 5-[1,2-$^3$H(N)] as a radioligand. Cyanopindolol (100 nM) and mesulergine (100 nM) were included in the assay to block out 5-HT$_{1A}$ and 5-HT$_{1C}$ binding sites respectively. The concentration of the compounds of the accompanying Examples required to displace 50% of the specific binding (IC$_{50}$) is below 1 μM in each case.

The activity of test compounds as agonists of the 5-HT$_1$-like receptor was measured in terms of their ability to mediate contraction of the saphenous vein of New Zealand White rabbits, using the procedure described in *Arch. Pharm.*, 1990, 342, 111. Agonist potencies were calculated as -log$_{10}$EC$_{50}$ (pEC$_{50}$) values, from plots of percentage 5-HT (1 μm) response against the concentration of the agonist. The compounds of accompanying Examples 1, 4, 6, 19–21, 27, 28, 30, 39–42, 44, 45, 49, 52, 53, 56, 61, 65, 88, 93 and 110 were tested and were found to possess pEC$_{50}$ values in this assay of not less than 5.0 in each case.

EXAMPLE 1

2-[5-(5-(3-Benzyl-1,2,4-oxadiazol)-yl)-1H-indol-3-yl]ethylamine Hydrogen Oxalate Hydrate 1. Ethyl-p-hydrazinobenzoate, Hydrochloride A solution of sodium nitrite (17.0 g, 0.24 mol) in water (90 ml) was added to a cooled solution of ethyl-p-amino benzoate (40 g, 0.24 mol) in concentrated hydrochloric acid (225 ml) at such a rate that the temperature did not exceed 0° C. The mixture was stirred at 0° C. for 0.1 h before adding to a stirred solution of tin (II) chloride dihydrate (202 g, 0.89 mol) in concentrated hydrochloric acid (135 ml) at such a rate that the temperature did not exceed −5° C. The resulting suspension was allowed to warm to room temperature over a 1 h period, filtered and washed with ether, mp 215°–217° C., δ(360 MHz, D$_2$O) 1.38 (3H, t, J=7.1 Hz, Me), 4.37 (2H, q, J=7.1 Hz, CH$_2$), 7.06 (1H, d, J=9 Hz, aromatic-H), 8.03 (1H, d, J=9 Hz, aromatic-H).

2. 2-(5-Carboethoxy-1H-indol-3-yl)ethylamine, Hydrogen Maleate

A solution of ethyl-p-hydrazinobenzoate hydrochloride (10 g, 46 mmol) and 4-chlorobutanal dimethyl acetal (7.8 g, 46 mmol) in ethanol/water (5:1, 500 ml) was heated at reflux for 2 h. The solvent was removed under vacuum and the residue chromatographed through silica-gel eluting with dichloromethane/ethanol/ammonia (40:8:1) to give the title-indole as an oil (3.69 g). The hydrogen maleate salt was prepared, mp 127° C.; (Found: C, 59.46; H, 5.96; N, 8.47. C$_{13}$H$_{16}$N$_2$O$_2$.C$_4$H$_4$O$_4$ requires C, 59.68; H, 5.93; N, 8.54%), m/e 232 (M+), δ(360 MHz, D$_2$O) 1.43 (3H, t, J=7.1 Hz, Me); 3.21 (2H, t, J=7.0 Hz, CH$_2$); 3.37 (2H, t, J=7.0 Hz, CH$_2$); 4.42 (2H, q, J=7.1 Hz, CH$_2$); 6.23 (2H, s, maleate-H); 7.40 (1H, s, indole-H); 7.56 (1H, d, J=8.8 Hz, aromatic-H); 7.88 (1H, dd, J=1.6 and 8.8 Hz, aromatic-H); 8.38 (1H, d, J=1.6 Hz, aromatic-H).

3. 2-[5-(5-(3-Benzyl-1,2,4-oxadiazol)yl)-1H-indol-3-yl]ethylamine, Hydrogen Oxalate Hydrate Sodium hydride (0.33 g of an 80% dispersion in oil, 11.0 mmol) was added to a stirred solution of phenyl acetamide oxime (1.74 g, 11.6 mmol) in anhydrous THF (50 ml) and the reaction mixture heated at reflux for 0.5 h. 2-(5-Carboethoxy-1H-indol-3-yl)ethylamine (1.19 g, 5.0 mmol) in THF (10 ml) was added and the reaction heated under reflux for 2 h. The mixture was allowed to cool to room temperature before adding water (20 ml) and extracting with dichloromethane (3×100 ml). The crude product remaining after removal of solvent under vacuum was chromatographed through silica-gel eluting with dichloromethane/ethanol/ammonia (40:8:1) to give the title-product (0.68 g). The hydrogen oxalate salt was prepared, mp 229° C.; (Found: C, 59.42; H, 4.92: N, 13.02. C$_{19}$H$_{18}$N$_4$O. C$_2$H$_2$O$_4$.0.85H$_2$O requires C, 59.53; H, 5.16; N, 13.22%); δ(360 MHz, D$_2$O) 3.18 (2H, t, J=7.4 Hz, CH$_2$); 3.31 (2H, t, J= 7.4 Hz, CH$_2$); 4.17 (2H, s, CH$_2$-Ph); 7.35–7.43 (6H, m, indole-H and aromatics); 7.63 (1H, d, J=8.6 Hz, aromatic-H); 7.87 (1H, d, J=8.6 Hz, aromatic-H); 8.40 (1H, s, aromatic-H).

EXAMPLE 2

2-[5-(5-(3-Methyl-1,2,4-oxadiazol)yl)-1H-indol-3-yl]ethylamine

Hydrogen Oxalate

This was prepared from methyl acetamide oxime and 2-(5-carboethoxy-1H-indol-3-yl)ethylamine as described for Example 1. The hydrogen oxalate salt was prepared mp 230° C. (Found: C, 52.91; H, 4.85; N, 16.01. C$_{13}$H$_{14}$N$_4$O.1.2(C$_2$H$_2$O$_4$) requires C, 52.78; H, 5.02; N, 16.41%); m/e 243 (M+H)+; δ(360 MHz, D$_2$O) 2.26 (3H, s, Me); 3.09 (2H, t, J=7.3 Hz, CH$_2$); 3.32 (2H, t, J=7.3 Hz, CH$_2$); 7.28 (1H, s, indole-H); 7.41 (1H, d, J=8.6 Hz, aromatic-H); 7.53 (1H, dd, J=1.6 and 8.6 Hz, aromatic-H); 7.86 (1H, d, J=1.6 Hz, aromatic-H).

EXAMPLE 3

N,N-Dimethyl-2-[5-(5-(3-benzyl-1,2,4-oxadiazol)yl)-1H-indol-3-yl]ethylamine

Sesquioxalate

1. N,N-Dimethyl-2-(5-carboethoxy-1H-indol-3-yl)ethylamine, Oxalate

Solutions of sodium borohydride (1.1 g, 2.2 mmol) in water (15 ml) and formaldehyde (7.5 ml) in methanol (7.5 ml) were added dropwise, simultaneously, over a 0.25 h period, to a solution of 2-(5-carboethoxy-1H-indol-3-yl)ethylamine (0.75 g, 4.3 mmol) in methanol (15 ml), at room temperature. The mixture was stirred for 0.25 h before adding concentrated hydrochloric acid (10 ml) and concentrating in vacuo. A second portion of c.HCl was added (7.5 ml) and the solution then basified with potassium carbonate (6.1 g). Extraction into ethyl acetate and chromatography of the crude residue through silica-gel eluting with dichloromethane/ethanol/ammonia (60:8:1) gave the title-N,N-dimethyl amine (0.64 g). The oxalate salt was prepared, mp 150° C.; (Found C, 52.76; H, 5.67; N, 6.65. C$_{15}$H$_{20}$N$_2$O$_2$.1.8.C$_2$H$_2$O$_4$ requires C, 52.89; H, 5.63; N, 6.63%); δ(360 MHz, D$_2$O) 1.42 (3H, t, J=7.1 Hz, Me); 2.94 (6H, s, N(Me)$_2$); 3.27 (2H, t, J=7.0 Hz, CH$_2$); 3.52 (2H, t, J=7.0 Hz, CH$_2$); 4.42 (2H, q, J=7.1 Hz, CH$_2$); 7.40 (1H, s, indole-H); 7.56 (1H, d, J=8.6 Hz, aromatic-H); 7.88 (1H, dd, J=1.6 and 8.6 Hz, aromatic-H); 8.36 (1H, d, J=1.6 Hz, aromatic-H).

2. N,N-Dimethyl-2-[5-(5-(3-benzyl-1,2,4-oxadiazol)yl)-1H-indol-3-yl]ethylamine, Sesquioxalate The title-compound was prepared from phenyl acetamide oxime and N,N-dimethyl-2-(5-carboethoxy-1H-indol-3-yl)ethylamine as described for Example 1. The sesquioxalate salt was prepared, mp 157°–158° C.; (Found: C, 59.14; H, 5.29; N, 11.35.C$_{21}$H$_{22}$N$_4$O.1.6.C$_2$H$_2$O$_4$ requires C, 59.26; H, 5.19; N, 11.42%); m/e 347 (M+H)+; δ(360 MHz, D$_2$O) 2.88 (6H, s, N(Me)$_2$); 3.02 (2H, br t, J=7.3 Hz, CH$_2$); 3.32 (2H, br t, J=7.3 Hz, CH$_2$); 3.99 (2H, s, CH$_2$-phenyl); 7.13 (1H, s, indole-H); 7.34–7.49 (7H, m, aromatics); 7.82 (1H, s, aromatic-H).

EXAMPLE 4

2-[5-(5-(3-Benzyl-1,2,4-oxadiazol)yl)methyl)-1H-indol-3-yl]ethylamine

Hydrogen Oxalate

1. Ethyl-p-hydrazinophenylacetate, Hydrochloride

This was prepared from ethyl-p-amino-phenyl acetate as described for Example 1, mp 188°–190° C., δ(360 MHz, D$_6$-DMSO) 1.44 (3H, t, J=7.1 Hz, Me); 3.88 (2H, s, CH$_2$); 4.36 (2H, t, J=7.1 Hz, CH$_2$); 7.20 (2H, d, J=8.5 Hz, aromatics); 7.50 (2H, d, J=8.5 Hz, aromatics).

2. 2-(5-Carboethoxymethyl-1-H-indol-3-yl)ethylamine, Hydrogen Maleate

The title-compound was prepared from ethyl-p-hydrazinophenylacetate and 4-chlorobutanol dimethyl acetal as described for Example 1. The hydrogen maleate salt was prepared, mp 105°–108° C.; (Found: C, 59.31; H, 6.07; N, 7.43.C$_{14}$H$_{18}$N$_2$O$_2$.C$_4$H$_4$O$_4$.0.1H$_2$O requires C, 59.36; H, 6.14; N, 7.69%); m/e 246 (M+); δ(360 MHz, D$_2$O) 1.23 (3H, t, J=7.1 Hz, Me); 3.16 (2H, t, J=7.0 Hz, CH$_2$); 3.33 (2H, t, J=7.0 Hz, CH$_2$); 3.82 (2H, s, CH$_2$); 4.18 (2H, q, J=7.1 Hz, CH$_2$Me); 6.29 (2H, s, maleate-H); 7.17 (1H, dd, J=1.6 and 8.4 Hz, aromatic-H); 7.32 (1H, s, indole-H); 7.49 (1H, d, J=8.4 Hz, aromatic-H); 7.56 (1H, s, aromatic-H).

3. 2-[5-(5-(3-Benzyl-1,2,4-oxadiazol)-ylmethyl)-1H-indol-3-yl]ethylamine, Hydrogen Oxalate This was prepared from the preceding ester and phenylacetamide oxime as described for Example 1. The hydrogen oxalate salt was prepared, mp 176°–178° C. (isopropyl alcohol); (Found: C, 62.37; H, 5.34; N, 13.15.$C_{20}H_{20}N_4O.C_2H_2O_4$ requires C, 62.55; H, 5.25; N, 13.26%); m/e 333 (M+H)$^+$; $\delta$(360 MHz, D$_2$O) 3.10 (2H, t, J=6.9 Hz, CH$_2$); 3.28 (2H, t, J=6.9 Hz, CH$_2$); 4.01 (2H, s, CH$_2$); 4.29 (2H, s, CH$_2$); 7.11 (1H, dd, J=1.6 and 8.4 Hz, aromatic-H); 7.25–7.38 (6H, m, 5 x aromatic-H and 1 x indole-H); 7.44 (1H, d, J=8.4 Hz, aromatic-H); 7.53 (1H, d, J=1.6 Hz, aromatic-H).

EXAMPLE 5

2-[5-(5-(3-Methyl-1,2,4-oxadiazol)ylmethyl)-1H-indol-3-yl]ethylamine

Hydrogen Oxalate Hydrate

Prepared from methyl acetamide oxime and 2-(5-carboethoxymethyl-1H-indol-3-yl)ethylamine as described for Example 1. The hydrogen oxalate salt was prepared, mp 72°–74° C.; (Found: C, 53.45; H, 5.26; N, 15.15.$C_{14}H_{16}N_4O.C_2H_2O_4.0.75H_2O$ requires C, 53.40; H, 5.46; N, 15.56%); $\delta$(360 MHz, D$_2$O) 2.32 (3H, s, Me); 3.15 (2H, t, J=7.1 Hz, CH$_2$); 3.33 (2H, t, J=7.1 Hz, CH$_2$); 4.37 (2H, s, CH$_2$); 7.20 (1H, dd, J=1.6 and 8.4 Hz, aromatic-H); 7.32 (1H, s, indole-H); 7.51 (1H, d, J=8.4 Hz, aromatic-H); 7.62 (1H, s, aromatic-H).

EXAMPLE 6

2-[5-(5-(3-Amino-1,2,4oxadiazol)ylmethyl-1H-indol-3-yl]ethylamine

Hydrogen Oxalate

Hydroxyguanidine sulphate (2.76 g, 10.4 mmol) was added to a stirred solution of sodium (0.91 g, 39 mmol) in ethanol (40 ml). The mixture was stirred for 0.5 h before adding a solution of 2-(5-carboethoxymethyl-1H-indol-3-yl)ethylamine (0.85 g, 3.5 mmol) in ethanol (20 ml) and refluxing for 2 h. After cooling to room temperature the ethanol was removed under vacuum and the residue chromatographed through silica-gel eluting with dichloromethane/ethanol/ammonia (40:8:1) to give the title-product. The hydrogen oxalate salt was prepared, mp 85°–87° C.; (Found: C, 47.07; H, 5.28; N, 20.71.$C_{13}H_{15}N_5O.C_2H_2O_4.1.2H_2O.0.3$ ($C_1H_5N_3O$) requires C, 46.73; H, 5, 41; N, 21.01%); m/e 257 (M$^+$); $\delta$(360 MHz, D$_2$O) 3.14 (2H, t, J=7.0 Hz, CH$_2$); 3.32 (2H, t, J=7.0 Hz, CH$_2$); 4.23 (2H, s, CH$_2$); 7.17 (1H, dd, J=1.6 and 8.4 Hz, aromatic-H); 7.32 (1H, s, indole-H); 7.49 (1H, d, J=8.4 Hz, aromatic-H); 7.58 (1H, d, J=1.6 Hz, aromatic-H).

EXAMPLE 7

2-[5-(5-(3-Phenyl-1,2,4-oxadiazol)ylmethyl)-1H-indol-3-yl]ethylamine

Hydrogen Oxalate

The title-compound was prepared from phenyl amide oxime and 2-(5-carboethoxymethyl-1H-indol-3-yl)ethylamine as described for Example 1. The hydrogen oxalate salt was prepared, mp 82°–84° C.; (Found: C, 61.57; H, 5.12; N, 13.03.$C_{19}H_{18}N_4O.C_2H_2O_4.0.3C_2H_5OH$ requires C, 61.44; H, 5.20; N, 13.27%); m/e 318 (M$^+$); $\delta$(360 MHz, D$_2$O) 3.13 (2H, t, J=7.0 Hz, CH$_2$); 3.31 (2H, t, J=7.0 Hz); 4.44 (2H, s, CH$_2$); 7.23 (1H, d, J=7.6 Hz, aromatic-H); 7.30 (1H, s, indole-H); 7.49–7.60 (4H, m, aromatic-Hs); 7.65 (1H, s, aromatic-H); 7.90 (2H, d, J=7.6 Hz, aromatic Hs).

EXAMPLE 8

2-[5-(5-(3-[2-Methoxybenzyl]-1,2,4-oxadiazol)ylmethyl)1H-indol-3-yl]ethylamine

Hydrogen Oxalate

Prepared from 2-methoxybenzyl amide oxime and 2-(5-carboethoxymethyl-1H-indol-3-yl)ethylamine as described for Example 1. The hydrogen oxalate salt was prepared, mp 68°–70° C.; (Found: C, 59.73; H, 5.33; N, 11.97.$C_{21}H_{22}N_4O_2.1.2C_2H_2O_4$ requires C, 59.74; H, 5.23; N, 11.91%); m/e 363 (M+H)$^+$; $\delta$(360 MHz, D$_2$O) 3.10 (2H, t, J=7.0 Hz, CH$_2$); 3.29 (2H, t, J=7.0 Hz, CH$_2$); 3.68 (3H, s, OMe); 3.99 (2H, s, CH$_2$); 4.31 (2H, s, CH$_2$); 6.96–7.01 (2H, m, aromatic-Hs); 7.12 (1H, dd, J=1.6 and 8.4 Hz, aromatic-H); 7.23 (1H, d, J=8.4 Hz, aromatic-H); 7.29 (1H, s, indole-H); 7.29–7.35 (1H, m, aromatic-H); 7.45 (1H, d, J=8.4 Hz, aromatic-H); 7.56 (1H, s, aromatic-H).

EXAMPLE 9

N,N-Dimethyl-2-[5-(5-(3-benzyl-1,2,4-oxadiazol)ylmethyl)-1H-indol-3-yl]ethylamine

Hydrogen Oxalate

1. N,N-Dimethyl-2-(5-carboethoxymethyl-1H-indol-3-yl)ethylamine

Prepared as described for Example 3. $\delta$(360 MHz, CDCl$_3$) 1.26 (3H, t, J=7.0 Hz, Me); 2.36 (6H, s, N(Me)$_2$); 2.62 (2H, t, J=7.0 Hz, CH$_2$); 2.92 (2H, t, J=7.0 Hz, CH$_2$); 3.70 (2H, s, CH$_2$); 4.16 (2H, q, J=7.0 Hz, CH$_2$-Me); 6.98 (1H, br s, indole-H); 7.10 (1H, dd, J=1.6 and 8.6 Hz, aromatic-H); 7.28 (1H, d, J=8.6 Hz, aromatic-H); 7.48 (1H, s, aromatic-H).

2. N,N-Dimethyl-2-[5-(5-(3-benzyl-1,2,4-oxadiazol)ylmethyl)-1H-indol-3-yl]ethylamine

Hydrogen Oxalate

The title-compound was prepared from phenylacetamide oxime and the preceding ester as described for Example 1. The hydrogen oxalate salt was prepared, mp 174°–176° C. (isopropyl alcohol); (Found: C, 63.79; H, 5.91; N, 12.31.$C_{22}H_{24}N_4O.C_2H_2O_4$ requires C, 63.99; H, 5.82; N, 12.44%); m/e 361 (M+H)$^+$; $\delta$ (250 MHz, D$_2$O) 2.88 (6H, s, N(Me)$_2$); 3.16 (2H, t, J=7.3 Hz, CH$_2$); 3.41 (2H, t, J=7.3 Hz, CH$_2$); 4.06 (2H, s, CH$_2$); 4.35 (2H, s, CH$_2$); 7.15 (1H, dd, J=1.6 and 8.4 Hz, aromatic-H); 7.29–7.40 (6H, m, 1 x indole-H and 5 x aromatics); 7.46 (1H, d, J=8.5 Hz, aromatic-H); 7.58 (1H, br s, aromatic-H).

EXAMPLE 10

N,N-Dimethyl-2-[5-(5-(3-Methyl-1,2,4-oxadiazol)ylmethyl)-1H-indol-3-yl]ethylamine

Sesquioxalate

Prepared from methylacetamide oxime and N,N-dimethyl-2-(5-carboethoxymethyl-1H-indol-3-yl)ethylamine as described for Example 1. The sesquioxalate salt was prepared, mp 159°–160° C. (isopropyl alcohol); (Found: C, 54.03; H, 5.61; N, 13.31.$C_{16}H_{20}N_4.1.5$ ($C_2H_2O_4$).0.1H$_2$O requires C, 54.17; H, 5.55; N, 13.30%); $\delta$ (360 MHz, D$_2$O) 2.32 (3H, s, Me); 2.91 (6H, s, N(Me)$_2$); 3.09 (1H, t, J=7.4 Hz, CH$_2$); 3.21 (1H, t, J=7.4 Hz, CH$_2$); 4.36 (2H, s, CH$_2$); 7.19 (1H, dd, J=1.6 and 8.4 Hz, aromatic-H); 7.34 (1H, s, indole-H); 7.50

(1H, d, J=8.4 Hz, aromatic-H); 7.61 (1H, s, aromatic-H).

EXAMPLE 11

2-[5-(2-(5-[3-Benzyl-1,2,4-oxadiazol]yl)ethyl)-1H-indol-3-yl]ethylamine

Maleate 1. 2-[5-(2-(Carboethoxy)ethyl)-1H-indol-3-yl]ethylamine, Hydrogen Maleate Prepared from ethyl-p-hydrazinophenylpropionate and 4-chlorobutanal dimethylacetal as described for Example 1. The hydrogen maleate salt was prepared, mp 114°–116° C. (isopropyl alcohol); (Found: C, 60.67; H, 6.49; N, 7.43.$C_{15}H_{20}N_2O_2.C_4H_4O_4$ requires C, 60.63; H, 6.43; N, 7.44%); m/e 260 (M$^+$); $\delta$ (360 MHz, $D_2O$) 1.15 (3H, t, J=7.2 Hz, Me); 2.75 (2H, t, J=7.4 Hz, $CH_2$); 3.06 (2H, t, J=7.3 Hz, $CH_2$); 3.15 (2H, t, J=7.3 Hz, $CH_2$); 3.32 (2H, t, J=7.4 Hz, $CH_2$); 4.08 (2H, q, J=7.2 Hz, $CH_2$); 6.29 (2H, s, maleate-Hs); 7.14 (1H, dd, J=1 and 8.4 Hz, aromatic-H); 7.29 (1H, s, indole-H); 7.46 (1H, d, J=8.4 Hz, aromatic-H); 7.50 (1H, s, aromatic-H).

2. 2-[5-(2-(5-[3-Benzyl-1,2,4-oxadiazol]yl)ethyl)-1H-indol-3-yl]ethylamine, Maleate Prepared from the preceding tryptamine and phenylacetamide oxime as described for Example 1. The maleate salt was prepared, mp 113°–114° C. (isopropyl-alcohol/ether); (Found: C, 68.40; H, 6.06; N, 13.84.$C_{21}H_{22}N_4O.C_2H_2O_2$ requires C, 68.30; H, 5.98; N, 13.85%); m/e 346 (M$^+$); $\delta$ (360 MHz, $D_2O$) 3.05 (2H, t, J=7.0 Hz, $CH_2$); 3.21 (4H, t, J=6.8 Hz, 2 of $CH_2$); 4.00 (2H, s, $CH_2$); 6.01 (1H, s, maleate-H); 6.98 (1H, dd, J=1.6 and 8.3 Hz, aromatic-H); 7.06 (2H, d, J=6.7 Hz, indole-H and aromatic-H); 7.22–7.37 (6H, m, aromatic-Hs).

EXAMPLE 12

2-[5-(3-(5-[3-Benzyl-1,2,4-oxadiazol]yl)propyl)-1H-indol-3-yl]ethylamine

Oxalate 1. 2-[5-Carboethoxyprop-3-yl-1H-indol-3-yl]ethylamine

Prepared from ethyl-p-hydrazinophenylbutyrate and 4-chlorobutanal dimethyl acetal as described for Example 1; $\delta$ (250 MHz, $CDCl_3$) 1.24 (3H, t, J=7.2 Hz, Me); 1.94–2.06 (2H, m, $CH_2$); 2.34 (2H, t, J=7.4 Hz, $CH_2$); 2.76 (2H, t, J=7.4 Hz, $CH_2$); 2.90 (2H, t, J=7.3 Hz, $CH_2$); 3.03 (2H, t, J=7.3 Hz, $CH_2$); 4.12 (2H, q, J=7.2 Hz, $CH_2$); 7.01 (1H, s, indole-H); 7.02 (1H, dd, J=1.0 and 8.4 Hz, aromatic-H); 7.28 (1H, d, J=8.4 Hz, aromatic-H); 7.40 (1H, s, aromatic-H); 8.00 (1H, br s, NH).

2. 2-[5-(3-(5-[3-Benzyl-1,2,4-oxadiazol]yl)propyl)-1H-indol-3-yl]ethylamine, Oxalate The title compound was prepared from 2-[5-carboethoxyprop-3-yl-1H-indol-3-yl]ethylamine and phenyl acetamide oxime using the general procedure. The oxalate salt was prepared, mp 188°–189° C.; (Found: C, 68.32; H, 6.30; N, 13.76.$C_{22}H_{14}N_4O.0.5$ ($C_2H_2O_4$) requires C, 68.13; H, 6.22; N, 13.82%); $\delta$ (360 MHz, $D_6$-DMSO) 1.98–2.07 (2H, m, $CH_2$); 2.70 (2H, t, J=7.3 Hz, $CH_2$); 2.83–2.96 (6H, m, 3 of $CH_2$); 4.05 (2H, s, $CH_2$); 6.91 (1H, d, J=8.3 Hz, aromatic-H); 7.14 (1H, s, indole-H); 7.22–7.34 (7H, m, aromatic-H's).

EXAMPLE 13

2-[5-(3-(5-[3-Methyl-1,2,4-oxadiazol]yl)propyl)-1H-indol-3-yl]ethylamine

Hydrogen Maleate

Prepared from 2-[5-carboethoxyprop-3-yl-1H-indol-3-yl]ethylamine and acetamide oxime using the general procedure. The hydrogen maleate salt: mp 136°–137° C. (isopropylalcohol/ether); (Found: C, 60.33; H, 6.14; N, 14.35.$C_{16}H_{20}N_4O.0.9$ ($C_4H_4O_4$) requires C, 60.54; H, 6.12; N, 14.41%); m/e 284 (M$^+$); $\delta$ (360 MHz, $D_2O$) 2.14 (3H, s, Me); 2.80 (2H, t, J=7.05 Hz, $CH_2$); 2.87 (2H, t, J=7.05 Hz, $CH_2$); 3.13 (2H, t, J=7.1 Hz, $CH_2$); 3.34 (2H, t, J=7.1 Hz, $CH_2$); 7.05 (1H, dd, J=1.5 and 8.4 Hz, aromatic-H); 7.27 (1H, s, indole-H); 7.38 (1H, s, aromatic-H); 7.39 (1H, d, J=8.4 Hz, aromatic-H).

EXAMPLE 14

2-[5-(3-(5-[3-Cyclopropyl-1,2,4-oxadiazol]yl)propyl)-1H-indol-3-yl]ethylamine

Hydrogen Maleate

Prepared from 2-[5-carboethoxyprop-3-yl-1H-indol-3-yl]ethylamine and cyclopropyl amide oxime as described for Example 1. The hydrogen maleate salt was prepared, mp 130°–132° C.; (Found: C, 61.36; H, 6.15; N, 12.90.$C_{18}H_{22}N_4O.0.25H_2O$ requires C, 61.31; H, 6.19; N, 13.00%); m/e 310 (M$^+$); $\delta$ (360 MHz, $D_6$-DMSO) 0.83–0.88 (2H, m, $CH_2$); 1.00–1.06 (2H, m, $CH_2$); 1.98–2.11 (3H, m, CH and $CH_2$); 2.71 (2H, t, J=7.6 Hz, $CH_2$); 2.90 (2H, t, J=7.6 Hz, $CH_2$); 3.00 (2H, t, J=7.13 Hz, $CH_2$); 3.08 (2H, t, J=7.13 Hz, $CH_2$); 6.95 (1H, dd, J=1.4 and 8.2 Hz, aromatic-H); 7.19 (1H, d, J=1.4 Hz, aromatic-H); 7.29 (1H, d, J=8.2 Hz, aromatic-H); 7.33 (1H, s, indole-H); 7.70 (1H, br s, NH).

EXAMPLE 15

2-[5-(5-(3-Phenyl-1,2,4-oxadiazol)yl)-1H-indol-3-yl]ethylamine

Hydrogen Oxalate

Prepared from 2-(5-carboethoxy-1H-indol-3-yl)ethylamine and phenyl amide oxime using the general procedure. The hydrogen oxalate salt was prepared, mp 212°–213° C. (methanol); (Found: C, 61.90; H, 4.97; N, 14.64.$C_{18}H_{16}N_4O.0.85$ ($C_2H_2O_4$) requires C, 62.12; H, 4.68; N, 14.71%); $\delta$ (250 MHz, $CDCl_3$, free base) 3.00 (2H, t, J=7.4 Hz, $CH_2$); 3.10 (2H, t, J=7.4 Hz, $CH_2$); 7.16 (1H, s, indole-H); 7.46–7.54 (5H, m, aromatic-H); 8.05 (1H, dd, J=1.8 and 8.4 Hz, aromatic-H); 8.18–8.22 (2H, m, aromatic-H); 8.18 (1H, br s, NH); 8.54 (1H, s, aromatic-H).

Examples 16–26 were prepared from 2-(5-carboethoxy-1H-indol-3-yl)ethylamine and the appropriate amide oxime using the procedure described for Example 1, unless otherwise stated.

EXAMPLE 16

2-[5-(5-(3-Diphenylmethyl-1,2,4-oxadiazol)yl)-1H-indol-3-yl]ethylamine

Sesquioxalate

The crude product was chromatographed through silica gel eluting with dichloromethane/ethanol/ammonia (60:8:1). The sesquioxalate salt was prepared, mp 117°–118° C.; (Found: C, 63.22; H, 5.40; N, 9.90.$C_{25}H_{22}N_4O.1.4$ ($C_2H_4O_2$).0.7.$C_2H_5OH$ requires C, 63.44; H, 5.29; N, 10.14%); δ (360 MHz, D₆-DMSO) 3.06 (4H, br s, 2 of CH₂); 5.81 (1H, s, CH); 7.26–7.43 (11H, m, aromatic-H's); 7.57 (1H, d, J=8.5 Hz, aromatic-H); 7.83 (1H, dd, J=1.4 and 8.5 Hz, aromatic-H); 7.95 (1H, br s, NH); 8.37 (1H, s, aromatic-H).

EXAMPLE 17

2-[5-(5-(3-(2-Methoxybenzyl)-1,2,4-oxadiazol)yl)-1H-indol-3-yl]ethylamine

Oxalate

The oxalate salt was prepared, mp 244°–245° C. (isopropyl alcohol/ether); (Found: C, 63.45; H, 5.47; N, 13.97.C₂₀H₂₀N₄O₂.0.6 (C₂H₂O₄) requires C, 63.27; H, 5.31; N, 13.92%); m/e 349 (M++1); δ (360 MHz, CF₃CO₂D) 3.88 (2H, br s, CH₂); 4.31 (2H, br s, CH₂); 4.43 (3H, s, OMe); 4.93 (2H, s, CH₂); 7.35 (1H, br s, NH); 7.57 (2H, d, J=7.5 Hz, aromatic-H's); 7.85 (1H, d, J=7.5 Hz, aromatic-H); 7.92–7.96 (2H, m, aromatic-H's); 8.22 (1H, d, J=8.8 Hz, aromatic-H); 8.53 (1H, d, J=8.8 Hz, aromatic-H); 9.10 (1H, s, aromatic-H).

EXAMPLE 18

2-[5-[5-(3-(3-Methoxybenzyl)-1,2,4-oxadiazol)yl]-1H-indol-3-yl]ethylamine.

Hydrogen Maleate

Hydrogen maleate salt, mp 173°–175° C. (isopropyl alcohol/ether); (Found: C, 61.82; H, 5.33; N, 11.92.C₂₀H₂₀N₄O₂.C₄H₄O₄.0.1H₂O requires C, 61.82; H, 5.23; N, 12.01%); δ(360 MHz, D₆-DMSO) 3.07 (4H, br s, 2 of CH₂); 3.75 (3H, s, OMe); 4.12 (2H, s, CH₂); 6.85 (1H, dd, J=2.2 and 8.6 Hz, aromatic-H); 6.92 (1H, d, J=7.3 Hz, aromatic-H); 6.93 (1H, s, aromatic-H); 7.27 (1H, dd, J=7.7 and 7.7 Hz, aromatic-H); 7.42 (1H, d, J=2.2 Hz, aromatic-H); 7.56 (1H, d, J=8.6 Hz, aromatic-H); 7.71 (2H, br s, NH₂); 7.82 (1H, dd, J=1.5 and 8.6 Hz, aromatic-H); 8.37 (1H, s, aromatic-H); 11.48 (1H, s, NH).

EXAMPLE 19

2-[5-[5-(3-(4-Methoxybenzyl)-1,2,4-oxadiazol)yl]-1H-indol-3-yl]ethylamine

Hydrogen Maleate

Hydrogen maleate salt, mp 195°–196° C. (isopropyl alcohol/ether); (Found: C, 61.95; H, 5.30; N, 11.99.C₂₀H₂₀N₄O₂.C₄H₄O₄ requires C, 62.06; H, 5.21; N, 12.06%); δ(360 MHz, D₆-DMSO/D₂O) 3.15 (2H, t, J=7.3 Hz, CH₂); 3.32 (2H, t, J=7.3 Hz, CH₂); 3.80 (3H, s, Me); 4.04 (2H, s, CH₂); 6.98 (2H, d, J=8.7 Hz, aromatic-H's); 7.33 (2H, d, J=8.7 Hz, aromatic-H's); 7.35 (1H, s, aromatic-H); 7.55 (1H, d, J=8.6 Hz, aromatic-H); 7.76 (1H, dd, J=1.6 and 8.6 Hz, aromatic-H); 8.24 (1H, s, aromatic-H).

EXAMPLE 20

2-[5-[5-(3-(4-Acetylaminobenzyl)-1,2,4-oxadiazol)yl]-1H-indol-3-yl]ethylamine

Bisoxalate

Prepared as described for Example 6. The bis oxalate salt was prepared, mp 113°–115° C.; (Found: C, 53.67; H, 4.67; N, 13.46.C₂₁H₂₁N₅O₂.2(C₂H₂O₄).0.25 H₂O requires C, 53.62; H, 4.59; N, 13.51%); δ(360 MHz, D₆-DMSO) 2.03 and 2.08 (total 3H, s, Me); 3.07 (4H, br s, 2 of CH₂); 3.92 and 4.08 (total 2H, s, CH₂); 6.53 and 7.27 (total 2H, d, J=8.3 Hz, aromatic-H's); 6.99 and 7.56 (total 2H, d, J=8.4 Hz, aromatic-H's); 7.41 (1H, s, aromatic-H); 7.53 (1H, d, J=8.5 Hz, aromatic-H); 7.80 (1H, dd, J=1.5 and 8.5 Hz, aromatic-H); 7.97 (2H, br s, NH₂); 8.35 (1H, s, aromatic-H); 9.94 (1H, s, NH); 11.54 (1H, s, NH).

EXAMPLE 21

2-[5-[5-(3-(4-Methylsulphonylaminobenzyl)-1,2,4-oxadiazol)yl]-1H-indol-3-yl]ethylamine

Sesquioxalate

Prepared as described for Example 6. The sesquioxalate salt was prepared, mp 219°–220° C.; (Found: C, 50.91; H, 4.61; N, 12.59.C₂₀H₂₁N₅O₃.1.5 (C₂H₂O₄) requires C, 50.55; H, 4.43; N, 12.81%); δ(360 MHz, D₆-DMSO) 2.97 (3H, s, Me); 3.06 (4H, br s, 2 of CH₂); 4.10 (2H, s, CH₂); 7.18 (2H, d, J=8.4 Hz, aromatic-H's); 7.32 (2H, d, J=8.4 Hz, aromatic-H's); 7.42 (1H, s, aromatic-H); 7.55 (1H, d, J=8.6 Hz, aromatic-H); 8.36 (1H, s, aromatic-H); 9.70 (1H, br s, NH); 11.50 (1H, s, NH).

EXAMPLE 22

2-[5-[5-(3-Phenethyl-1,2,4-oxadiazol)yl]-1H-indol-3-yl]ethylamine

Sesquioxalate

The sesquioxalate salt, mp 144°–146° C.; (Found: C, 58.05; H, 5.00; N, 11.67.C₂₀H₂₀N₄O.1.6 (C₂H₂O₄).0.2 H₂O requires C, 57.90; H, 5.20; N, 11.53%); m/e 333 (M++1); δ(360 MHz, CD₃OD) 3.04–3.20 (4H, m, 2 of CH₂); 3.26–3.33 (4H, m, 2 of CH₂); 7.15–7.28 (5H, m, aromatic-H's); 7.33 (1H, s, aromatic-H); 7.55 (1H, d, J=8.49 Hz, aromatic-H); 7.90 (1H, dd, J=1.6 and 8.49 Hz, aromatic-H); 8.42 (1H, s, aromatic-H).

EXAMPLE 23

2-[5-[5-(3-Phenpropyl-1,2,4-oxadiazol)yl]-1H-indol-3-yl]ethylamine. Hydrogen Maleate The hydrogen maleate salt, mp 150°–151° C. (isopropyl alcohol/ether); (Found: C, 63.65; H, 5.64; N, 11.87.C₂₁H₂₂N₄O. 1.17 (C₄H₄O₄) requires C, 63.93; H, 5.57; N, 11.60%); δ(360 MHz, D₆-DMSO/D₂O) 2.02–2.18 (2H, m, CH₂); 2.65–2.84 (4H, m, 2 of CH₂); 3.14–3.24 (2H, m, CH₂); 3.28–3.40 (2H, m, CH₂); 7.16–7.44 (6H, m, aromatic-H); 7.56–7.68 (1H, m, aromatic-H); 7.74–7.86 (1H, m, aromatic-H); 8.24–8.35 (1H, m, aromatic-H).

EXAMPLE 24

2-[5-[5-(3-Cyclopropyl-1,2,4-oxadiazol)yl]-1H-indol-3-yl]ethylamine

Hemisuccinate

The hemisuccinate salt was prepared, mp 205°–207° C. (isopropylalcohol/ether); (Found: C, 61.89; H, 5.91; N, 16.88.C₁₅H₁₆N₃O.0.5 (C₄H₆O₄).0.15 H₂O requires C, 61.86; H, 5.89; N, 16.97%); δ(360 MHz, D₆-DMSO) 0.98–1.05 (2H, m, CH₂); 1.07–1.13 (2H, m, CH₂); 2.13–2.20 (1H, m, CH); 2.95 (4H, m, 2 of CH₂); 7.36 (1H, s, aromatic-H); 7.53 (1H, d, J=8.6 Hz, aromatic-H); 7.77 (1H, dd, J=1.5 and 8.6 Hz, aromatic-H); 8.30 (1H, s, aromatic-H); 11.39 (1H, br s, NH).

EXAMPLE 25

2-[5-[5-(3-Ethyl-1,2,4-oxadiazol)yl]-1H-indol-3-yl]ethylamine

Bisoxalate Hemihydrate

The bisoxalate hemihydrate salt, mp 195°–197° C.; (Found: C, 48.34; H, 4.71; N, 12.41.$C_{14}H_{16}N_4O$.2($C_2H_2O_4$).0.5 $H_2O$ requires C, 48.54; H, 4.75; N, 12.57%); m/e 257 (M$^+$+1); δ(360 MHz, D$_6$-DMSO) 1.30 (3H, t, J=7.6 Hz, Me); 2.78 (2H, q, J=7.6 Hz, CH$_2$); 3.08 (4H, br s, 2 of CH$_2$); 7.43 (1H, d, J=1.8 Hz, aromatic-H); 7.57 (1H, d, J=8.5 Hz, aromatic-H); 7.82 (1H, dd, J=1.8 and 8.5 Hz, aromatic-H); 7.96 (2H, br s, NH$_2$); 8.38 (1H, s, aromatic-H).

EXAMPLE 26

2-[5-[5-(3-(4-Trifluoromethylbenzyl)-1,2,4-oxadiazol)yl]-1H-indol-3-yl]ethylamine

Bisoxalate

The bisoxalate salt, mp 125°–127° C.; (Found: C, 50.26; H, 4.07; N, 9.73.$C_{20}H_{17}F_3N_4O$.2 ($C_2H_2O_4$).0.25 $H_2O$ requires C, 50.09; H, 3.86; N, 9.73%); m/e 387 (M$^+$+1); δ(360 MHz, D$_6$-DMSO) 3.06 (4H, br s, 2 of CH$_2$); 4.29 (2H, s, CH$_2$); 7.43 (1H, s, aromatic-H); 7.56 (1H, d, J=8.5 Hz, aromatic-H); 7.60 (2H, d, J=8.1 Hz, aromatic-H's); 7.73 (2H, d, J=8.1 Hz, aromatic-H's); 7.81 (1H, d, J=8.5 Hz, aromatic-H); 7.91 (1H, br s, NH); 8.36 (1H, s, aromatic-H).

EXAMPLE 27

N,N-Dimethyl-2-[5-[5-(3-(4-Acetylaminobenzyl)-1,2,4-oxadiazol)yl]-1H-indol-3-yl]ethylamine

Succinate Dihydrate

The title compound was prepared from N,N-dimethyl-2-(5-carboethoxy-1H-indol-3-yl)ethylamine and 4-acetylaminobenzyl amide oxime using the procedure described for Example 6. The succinate salt was prepared, mp 76°–79° C.; (Found: C, 58.05; H, 6.02; N, 12.52.$C_{23}H_{25}N_5O_2$.$C_4H_6O_4$.2$H_2O$ requires C, 58.12; H, 6.32; N, 12.56%); m/e 404 (M$^+$+1); δ(360 MHz, D$_6$-DMSO) 2.02 (3H, s, Me); 2.44 (6H, s, N(Me)$_2$) 2.81 (2H, t, J=7.2 Hz, CH$_2$); 2.97 (2H, t, J=7.2 Hz, CH$_2$); 4.08 (2H, s, CH$_2$); 7.27 (2H, d, J=8.5 Hz, aromatic-H's); 7.36 (1H, s, aromatic-H); 7.52 (1H, d, J=8.5 Hz, aromatic-H); 7.53 (2H, d, J=8.5 Hz, aromatic-H's); 7.78 (1H, dd, J=1.5 and 8.5 Hz, aromatic-H); 8.32 (1H, s, aromatic-H); 9.90 (1H, s, NH); 11.37 (1H, s, NH).

EXAMPLE 28

N,N-Dimethyl-2-[5-[5-(3-(4-Methylsulphonyl aminobenzyl)-1,2,4-oxadiazol)yl]-1H-indol-3-yl]ethyl amine

Succinate Dihydrate

Prepared from N,N-dimethyl-2-(5-carboethoxy-1H-indol-3-yl)ethylamine and 4-methylsulphonylaminobenzyl amide oxime as described for Example 6. The succinate salt was prepared, mp 65°–66° C.; (Found: C, 52.99; H, 5.74; N, 11.86.$C_{22}H_{15}N_5SO_3$.$C_4H_6O_4$.1.75$H_2O$ requires C, 53.00; H, 5.90; N, 11.88%); m/e 440 (M$^+$+1); δ(360 MHz, D$_6$-DMSO) 2.50 (6H, s, N(Me)$_2$); 2.96 (3H, s, Me); 2.86–3.04 (4H, m, 2 of CH$_2$); 4.10 (2H, s, CH$_2$); 7.18 (2H, d, J=8.3 Hz, aromatic-H); 7.32 (2H, d, J=8.3 Hz, aromatic-H); 7.37 (1H, s, aromatic-H); 7.53 (1H, d, J=8.4 Hz, aromatic-H); 7.79 (1H, d, J=8.4 Hz, aromatic-H); 8.33 (1H, s, aromatic-H); 11.40 (2H, s, 2 of NH).

EXAMPLE 29

2-[5-(5-(3-Naphth-2-yl-1,2,4-oxadiazol)ylmethyl)-1H-indol-3-yl]ethylamine

Sesquioxalate

Prepared from 2-(5-carboethoxymethyl-1H-indol-3-yl)ethylamine and 2-naphthyl amide oxime as described for Example 1. The sesquioxalate salt was prepared, mp 195°–197° C. (isopropylalcohol/ether); (Found: C, 61.07; H, 4.54; N, 11.15. $C_{23}H_{21}N_4O$. 1.6 ($C_2H_2O_4$) requires C, 61.28; H, 4.75; N, 10.91%); δ(360 MHz, D$_6$-DMSO) 2.99 (2H, t, J=7.3 Hz, CH$_2$); 3.07 (2H, t, J=7.3 Hz, CH$_2$); 4.51 (2H, s, CH$_2$); 7.15 (1H, dd, J=1.6 and 8.4 Hz, aromatic-H); 7.26 (1H, d, J=1.6 Hz, aromatic-H); 7.38 (1H, d, J=8.4 Hz, aromatic-H); 7.59–7.64 (3H, m, aromatic-H's); 7.99–8.13 (4H, m, aromatic-H's); 8.60 (1H, s, aromatic-H).

EXAMPLE 30

N,N-Dimethyl-2-[5-[5-(3-Amino-1,2,4-oxadiazol)ylmethyl]-1H-indol-3-yl]ethylamine

Hemisuccinate Hydrate

Prepared from N,N-dimethyl-2-(5-carboethoxymethyl-1H-indol-3-yl)ethylamine and hydroxy guanidine sulphate as described for Example 6. The hemisuccinate salt was prepared, mp 150°–153° C.; (Found: C, 56.63; H, 6.62; N, 18.80. $C_{15}H_{19}N_5O$. 0.6 ($C_4H_6O_4$). 0.75 $H_2O$ requires C, 56.63; H, 6.57; N, 18.94%); m/e 285 (M$^+$); δ(360 MHz, D$_2$O) 2.92 (6H, s, Me); 3.22 (2H, t, J=7.4 Hz, CH$_2$); 3.47 (2H, t, J=7.4 Hz, CH$_2$); 4.28 (2H, s, CH$_2$); 7.22 (1H, dd, J=1.5 and 8.4 Hz, aromatic-H); 7.35 (1H, s, aromatic-H); 7.52 (1H, d, J=8.4 Hz, aromatic-H); 7.62 (1H, s, aromatic-H).

EXAMPLE 31

2-[5-[2-(5-(3-Amino-1,2,4-oxadiazol)yl)ethyl]-1H-indol-3-yl]ethylamine

Hydrogen Maleate Hydrate

The title compound was prepared from 2-[5-(2-(carboethoxy)ethyl)-1H-indol-3-yl]ethylamine and hydroxy guanidine sulphate using the procedure described for Example 6. The hydrogen maleate salt was prepared, mp 147°–148° C. (isopropylalcohol/ether); (Found: C, 53.89; H, 5.47; N, 17.67. $C_{14}H_{17}N_5O$. $C_4H_4O_4$. 0.75 $H_2O$ requires C, 53.93; H, 5.65; N, 17.47%); δ(360 MHz, D$_2$O) 3.12 (2H, t, J=6.9 Hz, CH$_2$); 3.17 (4H, t, J=4.1 Hz, 2 of CH$_2$); 3.29 (2H, t, J=6.9 Hz, CH$_2$); 7.11 (1H, dd, J=1.5 and 8.4 Hz, aromatic-H); 7.27 (1H, s, aromatic-H); 7.40 (1H, s, aromatic-H); 7.44 (1H, d, J=8.4 Hz, aromatic-H).

EXAMPLE 32

2-[5-[2-(5-(3-Dimethylamino-1,2,4-oxadiazol)yl)ethyl]-1H-indol-3-yl]ethylamine

Hemisuccinate

Prepared from 2-[5-(2-(carboethoxy)ethyl)-1H-indol-3-yl]ethylamine and dimethylamino amide oxime as described for Example 6. The hemisuccinate, mp 184°–185° C.; (Found: C, 59.83; H, 6.79; N, 18.41. $C_{16}H_{21}N_5O$. 0.62 ($C_4H_6O_4$) requires C, 59.57; H, 6.69; N, 18.79%); δ(360 MHz, D$_2$O) 2.90 (6H, s, N(Me)$_2$); 3.12–3.20 (6H, m, 3 of CH$_2$); 3.30 (2H, t, J=6.7 Hz, CH$_2$); 7.09 (1H, dd, J=1.6 and 8.4 Hz, aromatic-H); 7.29 (1H, s, aromatic-H); 7.43 (1H, s, aromatic-H); 7.45 (1H, d, J=8.4 Hz, aromatic-H).

EXAMPLE 33

2-[5-[3-(5-Methyl-1,2,4-oxadiazol)yl]-1H-indol-3-yl]ethylamine

Bisoxalate 1. 2-(5-Amide oxime-1H-indol-3-yl )ethylamine

Hydroxylamine hydrochloride (1.2 g, 17.3 mmol) was added to a stirred solution of sodium metal (0.4 g, 17.5 mmol) in methanol (10 ml) followed by a solution of 2-(5-cyano-1H-indol-3-yl)ethylamine (1.25 g, 6.8 mmol), and the mixture refluxed for 16 h. The mixture was filtered through hyflo filter aid and the solvent removed under vacuum and the residue chromatographed through silica gel (dichloromethane/ethanol/ammonia 30:8:1) to give the title product, mp 79°–82° C.; δ(360 MHz, CD$_3$OD) 2.90–2.96 (4H, m, 2 of CH$_2$); 7.12 (1H, s, aromatic-H); 7.34 (1H, d, J=8.5 Hz, aromatic-H); 7.41 (1H, dd, J=1.6 and 8.5 Hz, aromatic-H); 7.87 (1H, s, aromatic-H).

2. 2-[5-[3-(5-Methyl-1,2,4-oxadiazol)yl]-1H-indol-3-yl]ethylamine, Bisoxalate

A solution of the preceding indolyl amide oxime (0.35 g, 1.6 mmol), sodium hydride (0.1 g of an 80% dispersion in oil, 3.2 mmol) and ethylacetate (0.5 g, 5.7 mmol), in ethanol (20 ml) was heated under reflux for 2 h. The solvent was removed under vacuum and the residue chromatographed through silica-gel eluting with dichloromethane/ethanol/ammonia (40:8:1) to give the title product (0.3 g). The bisoxalate salt was prepared, mp 178°–180° C.; (Found: C, 48.68; H, 4.58; N, 13.04. C$_{13}$H$_{14}$N$_4$O. 2 (C$_2$H$_2$O$_4$) requires C, 48.35; N, 4.30; N, 13.27%); m/e 242 (M+); δ(360 MHz, D$_2$O) 2.55 (3H, s, Me); 3.15 (2H, t, J=7.2 Hz, CH$_2$); 3.34 (2H, t, J=7.2 Hz, CH$_2$); 7.33 (1H, s, aromatic-H); 7.51 (1H, d, J=8.4 Hz, aromatic-H); 7.61 (1H, dd, J=1.6 and 8.4 Hz, aromatic-H); 7.97 (1H, d, J=1.6 Hz, aromatic-H).

EXAMPLE 34

2-[5-[3-(5-Benzyl-1,2,4-oxadiazol)yl]-1H-indol-3-yl]ethylamine

Hydrogen Maleate

Prepared from 2-(5-amide oxime-1H-indol-3-yl)ethylamine and ethyl phenyl acetate as described for Example 33. The hydrogen maleate salt was prepared, mp 184°–186° C.; (Found: C, 64.10; H, 5.23; N, 13.25. C$_{19}$H$_{18}$N$_4$O. 0.9 (C$_4$H$_4$O$_4$) requires C, 64.19; H, 5.15; N, 13.25%); δ(360 MHz, D$_2$O) 3.13 (2H, t, J=7.3 Hz, CH$_2$); 3.22 (2H, t, J=7.3 Hz, CH$_2$); 4.35 (2H, s, CH$_2$); 7.26 (1H, s, aromatic-H); 7.28–7.40 (5H, m, aromatic-H's); 7.47 (1H, d, J=8.6 Hz, aromatic-H); 7.82 (1H, dd, J=1.3 and 8.6 Hz, aromatic-H); 8.30 (1H, s, aromatic-H).

EXAMPLE 35

2-[5-[3-(5-Methyl-1,2,4-oxadiazol)ylmethyl]-1H-indol-3-yl]ethylamine

Hydrogen Maleate 1. 2-(5-Acetamide oxime-1H-indol-3-yl)ethyl amine

Prepared from 2-(5-cyanomethyl-1H-indol-3-yl)ethylamine and hydroxylamine as described in the preparation of Example 33; δ(360 MHz, CD$_3$OD) 3.28–3.35 (4H, m, 2 of CH$_2$); 3.47 (2H, s, CH$_2$); 7.04 (1H, d, J=8.4 Hz, aromatic-H); 7.06 (1H, s, aromatic-H); 7.28 (1H, d, J=8.4 Hz, aromatic-H); 7.48 (1H, s, aromatic-H).

2. 2-[5-[3-(5-Methyl-1,2,4-oxadiazol)ylmethyl]-1H-indol-3yl]ethylamine, Hydrogen Maleate Prepared from the preceding indolyl acetamide oxime and ethyl acetate using the general procedure. The hydrogen maleate salt was prepared, mp 145°–149° C.; (Found: C, 58.38; H, 5.70; N, 15.30. C$_{14}$H$_{16}$N$_4$O. C$_4$H$_4$O$_4$ requires C, 58.06; H, 5.41; N, 15.05%); m/e 256 (M+); δ(360 MHz, D$_2$O) 2.55 (3H, s, Me); 3.16 (2H, t, J=7.0 Hz, CH$_2$); 3.34 (2H, t, J=7.0 Hz, CH$_2$); 4.18 (2H, s, CH$_2$); 7.18 (1H, d, J=8.4 Hz, aromatic-H); 7.32 (1H, s, aromatic-H); 7.50 (1H, d, J=8.4 Hz, aromatic-H); 7.60 (1H, s, aromatic-H).

EXAMPLE 36

2-[5-[3-(5-Benzyl-1,2,4-oxadiazol)ylmethyl]-1H-indol-3-yl]ethylamine

Hydrogen Maleate

Prepared from 2-(5-acetamide oxime-1H-indol-3-yl)ethylamine and ethyl phenyl acetate using the general procedure. The hydrogen maleate salt, mp 143°–144° C.; (Found: C, 64.27; H, 5.56; N, 12.42. C$_{20}$H$_{20}$N$_4$O. C$_4$H$_4$O$_4$ requires C, 64.28; H, 5.39; N, 12.49%); δ(360 MHz, D$_2$O) 3.11 (2H, t, J=7.3 Hz, CH$_2$); 3.28 (2H, t, J=7.3 Hz, CH$_2$); 4.16 (2H, s, CH$_2$); 4.27 (2H, s, CH$_2$); 7.13 (1H, dd, J=1.5 and 8.4 Hz, aromatic-H); 7.29 (1H, s, aromatic-H); 7.32–7.41 (5H, m, aromatic-H); 7.44 (1H, d, J=8.4 Hz, aromatic-H); 7.56 (1H, s, aromatic-H).

EXAMPLE 37

N,N-Dimethyl-2-[5-[3-(5-benzyl-1,2,4-oxadiazol)ylmethyl]-1H-indol-3-yl]ethylamine Succinate A solution of formaldehyde (0.85 ml of a 35% solution in water) in methanol (10 ml) was added dropwise to a stirred solution of 2[5-[3-(5-benzyl-1,2,4-oxadiazol)ylmethyl]-1H-indol-3-yl]ethylamine (0.4 g, 1.2 mmol), sodium cyanoborohydride (0.13 g, 2.05 mmol) and glacial acetic acid (0.34 g), in methanol (15 ml). The solution was stirred for 2.5 h before basifying with a saturated solution of K$_2$CO$_3$ and extracting with ethyl acetate (3×50 ml). The combined extracts were dried (MgSO$_4$), evaporated, and the residue chromatographed through silica gel eluting with dichloromethane/ethanol/ammonia 60:8:1 to give the title product (0.33 g). The succinate salt was prepared, mp 195°–196° C.; (Found: C, 64.66; H, 6.37; N, 11.55. C$_{22}$H$_{24}$N$_4$O. 1.1 (C$_4$H$_6$O$_4$) requires C, 64.66; H, 6.29; N, 11.43%); m/e 360 (M+); δ(360 MHz, D$_2$O) 2.89 (6H, s, N(Me)$_2$); 3.18 (2H, t, J=7.4 Hz, CH$_2$); 3.43 (2H, t, J=7.4 Hz, CH$_2$); 4.16 (2H, s, CH$_2$); 4.27 (2H, s, CH$_2$); 7.14 (1H, d, J=8.4 Hz, aromatic-H); 7.31–7.40 (6H, m, aromatic-H's); 7.44 (1H, d, J=8.4 Hz, aromatic-H); 7.56 (1H, s, aromatic-H).

Examples 38–48 were prepared from 2-(5-carboethoxy-1H-indol-3-yl)ethylamine and the appropriate amide oxime using the procedure described for Example 6, unless otherwise stated.

EXAMPLE 38

2-[5-(5-(3-Methoxymethyl-1,2,4-oxadiazol)yl)-1H-indol-3-yl]ethylamine

Hemisuccinate

The hemisuccinate salt: mp 207°–210° C. (methanol/diethylether); (Found: C, 58.01; H, 5.85; N, 16.85. $C_{14}H_{16}N_4O_2.0.5(C_4H_6O_4)$ requires C, 58.00; H, 5.78; N, 16.91%); δ(360 MHz, $D_2O$) 3.21 (2H, t, J=7.2 Hz, $CH_2$); 3.35 (2H, t, J=7.2 Hz, $CH_2$); 3.51 (3H, s, Me); 4.68 (2H, s, $CH_2OMe$); 7.43 (1H, s, Ar-H); 7.65 (1H, d, J=8.6 Hz, Ar-H); 7.90 (1H, dd, J=8.6 and 1.6 Hz, Ar-H); 8.41 (1H, d, J=1.6 Hz, Ar-H).

EXAMPLE 39

2-[5-(5-(3-(4-N-Methylcarbamoyl benzyl)-1,2,4-oxadiazol)yl)-1H-indol-3-yl)]ethylamine

Succinate

Hydrate

The succinate salt mp 108°–110° C.; (Found: C, 59.12; H, 5.59; N, 14.05. $C_{21}H_{21}N_5O_2. (C_4H_6O_4). 0.75H_2O$ requires C, 59.22; H, 5.66; N, 13.82%). δ(360 MHz, $D_6$-DMSO) 2.77 (3H, d, J=4.5 Hz, $CH_3$); 3.01 (4H, br s, 2 of $CH_2$); 4.21 (2H, s, $CH_2$); 7.40 (1H, s, Ar-H); 7.43 (2H, d, J=8.2 Hz, Ar-H); 7.55 (1H, d, J=8.6 Hz, Ar-H); 7.79–7.81 (2H, d, J=8.2 Hz, Ar-H); 7.79–7.81 (1H, d, J=8.6 Hz, Ar-H); 8.35 (1H, s, Ar-H); 8.39 (1H, br q, J=4.5 Hz, NH).

EXAMPLE 40

2-[5-(5-(3-(4-N-Methylcarbamoylphenyl)-1,2,4-oxadiazol)yl)-1H-indol-3-yl]ethylamine. Succinate. Hydrate The succinate salt: mp 126°–128° C.; (Found: C, 58.31; H, 5.21; N, 14.22. $C_{20}H_{19}N_5O_2. (C_4H_6O_4). 0.75H_2O$ requires C, 58.47; H, 5.41; N, 14.21%); δ(360 MHz, $D_6$-DMSO) 2.83 (3H, d, J= 4.5 Hz, $CH_3$); 3.06 (4H, br s, 2 of $CH_2$); 3.37 (2H, br s, $NH_2$); 7.44 (1H, s, Ar-H); 7.62 (1H, d, J=8.5 Hz, Ar-H); 7.94 (1H, dd, J=1.6 and 8.5 Hz, Ar-H); 8.04 (2H, d, J=8.5 Hz, Ar-H); 8.19 (2H, d, J=8.5 Hz, Ar-H); 8.49 (1H, s, Ar-H); 8.62 (1H, br q, J=4.5 Hz, NH).

EXAMPLE 41

2-[5-(5-(3-(4-Methylaminosulphonylbenzyl)-1,2,4-oxadiazol)yl)-1H-indol-3-yl]ethylamine. Bissuccinate. Hydrate Bissuccinate salt: mp 49°–50° C. (hygroscopic salt); (Found: C, 50.91; H, 5.47; N, 10.79. $C_{20}H_{21}N_5SO_3. 2(C_4H_6O_4). 0.75H_2O$ requires C, 50.87; H, 5.26; N, 10.59%). δ(360 MHz, $D_2O$) 2.55 (3H, s, $CH_3$); 3.16 (2H, t, J=7.1 Hz, $CH_2$); 3.32 (2H, t, J=7.1 Hz, $CH_2$); 4.26 (2H, s, $CH_2$); 7.38 (1H, s, Ar-H); 7.58 (1H, d, J=8.9 Hz, Ar-H); 7.62 (2H, d, J=8.4 Hz, Ar-H); 7.79 (1H, dd, J=1.6 and 8.9 Hz, Ar-H); 7.84 (2H, d, J=8.4 Hz, Ar-H); 8.31 (1H, d, J=1.6 Hz, Ar-H).

EXAMPLE 42

2-[5-(5-(3-(4-Dimethylaminosulphonylbenzyl)-1,2,4-oxadiazol)yl)-1H-indol-3-yl]ethylamine

Hydrochloride

Hydrate

The hydrochloride monhydrate salt: mp 144°–145° C. (MeOH)/$Et_2O$); (Found: C, 52.71; H, 5.50; N, 14.44. $C_{21}H_{24}N_5SO_3Cl. 1H_2O$ requires C, 52.55; H, 5.46; N, 14.59%).

EXAMPLE 43

2-[5-(5-(3-(3-Methylsulphonylaminobenzyl)-1,2,4-oxadiazol)yl)-1H-indol-3-yl]ethylamine

Hydrochloride

Dihydrate

The hydrochloride dihydrate salt: mp 241°–242° C.; (Found: C, 48.54; H, 5.05; N, 13.59. $C_{20}H_{21}N_5SO_3. 1.2HCl. 2.4H_2O$ requires C, 48.19; H, 5.45; N, 14.05%).

EXAMPLE 44

2-[5-(5-(3-(4-Carbamoylaminobenzyl)-1,2,4-oxadiazol)yl)-1H-indol-3-yl]ethylamine

Sesquioxalate

Hemihydrate

The sesquioxalate hemihydrate salt: mp 194°–197° C.; (Found: C, 52.8; H, 4.75; N, 16.42. $C_{20}H_{21}N_6O_2. 1.5(C_2H_2O_4). 0.5H_2O$ requires C, 53.1; H, 4.65; N, 16.15%).

EXAMPLE 45

2-[5-(5-(3-Amino-1,2,4-oxadiazol)-yl)-1H-indol-3-yl]ethylamine

Bisoxalate

Hydrate

The bisoxalate salt: mp 160°–164° C.; (Found: C, 39.90; H, 4.29; N, 21.37. $C_{12}H_{13}N_5O. 2(C_2H_2O_4). 0.9(CH_5N_3O). 0.75H_2O$ requires C, 40.24; H, 4.60; N, 21.38%); δ(360 MHz, $D_2O$) 3.15 (2H, t, J=7.1 Hz, $CH_2$); 3.34 (2H, t, J=7.1 Hz, $CH_2$); 7.33 (1H, s, Ar-H); 7.51 (1H, d, J=8.5 Hz, Ar-H); 7.69 (1H, dd, J=1.5 and 8.5 Hz, Ar-H); 8.12 (1H, d, J=1.5 Hz, Ar-H).

EXAMPLE 46

2-[5-(5-(3-Acetylaminomethyl-1,2,4-oxadiazol)yl)-1H-indol-3-yl]ethylamine

Hemisuccinate

Monohydrate

The hemisuccinate monhydrate salt: mp 107°–110° C.; (Found: C, 54.47; H, 6.28; N, 17.81. $C_{15}H_{17}N_5O_2. 0.5(C_4H_6O_4). 1H_2O. 0.2(iPA)$ requires C, 54.43; H, 6.13; N, 18.03%); δ(360 MHz, $D_2O$) 2.14 (3H, s, $CH_3$); 3.14 (2H, t, J=7.1 Hz, $CH_2$); 3.34 (2H, t, J=7.1 Hz, $CH_2$); 4.51 (2H, s, $CH_2$); 7.33 (1H, s, Ar-H); 7.49 (1H, d, J=8.7 Hz, Ar-H); 7.68 (1H, dd, J=1.5 and 8.7 Hz, Ar-H); 8.09 (1H, d, J=1.5 Hz, Ar-H).

EXAMPLE 47

2-[5-(5-(3-(2-Acetylamino)ethyl-1,2,4-oxadiazol)yl)-1H-indol-3-yl]ethylamine

Oxalate

Hemihydrate

The oxalate hemihydrate salt: mp 188°–189° C.; (Found: C, 52.48; H, 5.56; N, 16.77. $C_{16}H_{19}N_5O_2. C_2H_2O_4. 0.6H_2O$ requires C, 52.20; H, 5.40; N, 16.90%).

EXAMPLE 48

2-[5-(5-(3-Aminomethyl-1,2,4-oxadiazol)yl)-1H-indol-3-yl]ethylamine

Succinate

Dihydrate

The succinate dihydrate salt: mp 125°–130° C.; (Found: C, 49.13; H, 6.06; N, 16.99. $C_{13}H_{15}N_5O.2(C_4H_6O_4).2.2H_2O$ requires C, 49.19; H, 6.16; N, 16.87%).

Examples 49–54 were prepared from N,N-dimethyl-2-(5-carboethoxy-1H-indol-3-yl)ethylamine and the appropriate amide oxime using the procedure described for Example 6.

EXAMPLE 49

N,N-Dimethyl-2-[5-(5-(3-amino-1,2,4-oxadiazol)yl)-1H-indol-3yl]ethylamine

Bisoxalate

Monohydrate

The bisoxalate monhydrate salt: mp 156°–158° C.; (Found: C, 46.49; H, 4.66; N, 15.83. $C_{14}H_{17}N_5O.1.8(C_2H_2O_4)$ $1H_2O$ requires C, 46.83; H, 5.04; N, 15.52%); $\delta$(360 MHz, $D_2O$) 2.93 (6H, s, 2 of $CH_3$); 3.18 (2H, t, J=7.6 Hz, $CH_2$); 3.46 (2H, t, J=7.6 Hz, $CH_2$); 7.33 (1H, s, Ar-H); 7.48 (1H, d, J=8.7 Hz, Ar-H); 7.65 (1H, dd, J=8.7 and 1.5 Hz, Ar-H); 8.04 (1H, d, J=1.5 Hz, Ar-H).

EXAMPLE 50

N,N-Dimethyl-2-[5-(5-(3-acetylaminomethyl-1,2,4-oxadiazol)yl)-1H-indol-3-yl]ethylamine Succinate Hemihydrate The succinate hemihydrate salt: mp 65°–70° C. (hygroscopic); (Found: C, 56.14; H, 6.03; N, 16.02. $C_{17}H_{21}N_5O_2.0.8(C_4H_6O_4).0.6H_2O$ requires C, 56.08; H, 6.29; N, 16.19%); $\delta$(360 MHz, $D_2O$) 2.16 (3H, s, $CH_3$); 2.96 (6H, s, 2 of $CH_3$); 3.15 (2H, t, J=7.8 Hz, $CH_2$); 3.45 (2H, t, J=7.8 Hz, $CH_2$); 4.50 (2H, s, $CH_2$); 7.31 (1H, s, Ar-H); 7.45 (1H, d, J=8.6 Hz, Ar-H); 7.61 (1H, dd, J=8.6 and 1.5 Hz, Ar-H); 7.96 (1H, d, J=1.5 Hz, Ar-H).

EXAMPLE 51

N,N-Dimethyl-2-[5-(5-(3-(2-acetylamino)ethyl-1,2,4-oxadiazol)yl)-1H-indol-3-yl]ethylamine Sesquioxalate Monohydrate The sesquioxalate monohydrate salt: mp 35° C. (hygroscopic); (Found: C, 51.76; H, 5.73; N, 14.17. $C_{18}H_{23}N_5O_2.1.4(C_2H_2O_4).0.9H_2O$ requires C, 51.65; H, 5.75; N, 14.47%).

EXAMPLE 52

N,N-Dimethyl-2[5-(5-(3-(4-carbamoylaminobenzyl)-1,2,4-oxadiazol)yl)-1H-indol-3-yl]ethylamine Hydrochloride The hydrochloride salt: mp 214°–215° C.; (Found: C, 57.70; H, 6.13; N, 17.34. $C_{22}H_{24}N_6O_2.1.25HCl.1.0C_2H_5OH$ requires C, 58.10; H, 6.35; N, 16.94%).

EXAMPLE 53

N,N-dimethyl-2-[5-(5-(3-(2-t-butyloxycarbonyl amino)ethyl-1,2,4-oxadiazol)yl)-1H-indol-3-yl]ethylamine Oxalate The oxalate salt: mp 184°–185° C.; (Found: C, 55.97; H, 6.38; N, 14.18. $C_{21}H_{30}N_5O_3.C_2H_2O_4.0.3H_2O$ requires C, 55.82; H, 6.44; N. 14.15%).

EXAMPLE 54

N,N-Dimethyl-2-[5-(5-(3-(4-N-methylcarbamoylbenzyl)-1,2,4-oxadiazol)yl)-1H-indol-3-yl]ethylamine Hemioxalate Dihydrate The hemioxalate dihydrate salt: mp 109°–111° C.; (Found: C, 59.88; H, 5.99; N, 14.24. $C_{23}H_{25}N_5O_2.0.5(C_2H_2O_4).1.9H_2O$ requires C, 59.71; H, 6.22; N, 14.51%).

EXAMPLE 55

N,N-Dimethyl-2-[5-(5-(3-(2-amino)ethyl-1,2,4-oxadiazol)yl)-1H-indol-3-yl]ethylamine Sesquioxalate Hemihydrate Trifluoroacetic acid (25 ml, 0.133 mol) was added to a solution of N,N-dimethyl-2-[5-(5-(3-(2-t-butyloxycarbonylamino)ethyl-1,2,4-oxadiazol)yl)-1H-indol-3-yl]ethylamine (0.5 g, 1.25 mmol) in anhydrous $CH_2Cl_2$ (10 ml) and the mixture stirred at 25° C. for 1 h. The solvent was removed under vacuum, aqueous $K_2CO_3$ (30 ml) added, and extracted with EtOAc (6×200 ml). The extracts were combined, dried, and evaporated to give the title-amine (0.36 g, 96%). The sesquioxalate salt was prepared: mp 220°–221° C.; (Found: C, 50.81; H, 5.78; N, 15.49. $C_{16}H_{21}N_5O.1.6(C_2H_2O_4)$ $0.5H_2O$ requires C, 50.97; H, 5.61; N, 15.48%); $\delta$(360 MHz, $D_2O$) 2.95 (6H, s, 2 of $CH_3$); 3.22–3.29 (4H, m, 2 of $CH_2$); 3.52 (4H, t, J=7.2 Hz, 2 of $CH_2$); 7.42 (1H, s, Ar-H); 7.61 (1H, d, J=8.6 Hz, Ar-H); 7.86 (1H, d, J=8.6 Hz, Ar-H); 8.32 (1H, s, Ar-H).

EXAMPLE 56

N,N-dimethyl-2-[5-(5-(3-(2-methylsulphonylamino)ethyl-1,2,4-oxadiazol)yl)-1H-indol-3-yl]ethylamine Oxalate.1.5

Hydrate

Methane sulphonyl chloride (0.14 ml, 1.81 mmol) in $CH_2Cl_2$) (10 ml) was added dropwise to a stirred solution of the preceding amine (Example 55; 0.36 g, 1.2 mmol) in $CH_2Cl_2$ (10 ml and pyridine (0.29 ml, 3.6 mmol), at $-30°$ C. The solution was stirred for 1 h, allowing to warm to room temperature. The solvent was removed under vacuum, and the residue purified by chromatography on silica-gel eluting with $CH_2Cl_2/EtOH/NH_3$ (90:8:1). The oxalate salt was prepared on the product obtained: mp<30° C. (hygroscopic); (Found: C, 46.15; H, 5.71; N, 14.16. $C_{17}H_{23}N_5SO_3.C_2H_2O_4.1.5H_2O$ requires C, 46.39; H, 5.49; N, 14.12%). $\delta$(360 MHz, $D_2O$) 2.94 (6H, s, 2 of $CH_3$); 2.99 (2H, t, J=6.5 Hz, $CH_2$); 3.09 (3H, s, $CH_3$); 3.16–3.24 (2H, m, $CH_2$); 3.48 (2H, t, J=7.4 Hz, $CH_2$); 3.55 (2H, t, J=6.5 Hz, $CH_2$); 7.35 (1H, s, Ar-H); 7.52

(1H, d, J=8.6 Hz, Ar-H); 7.72 (1H, dd, J=1.6 and 8.6 Hz, Ar-H); 8.13 (1H, d, J=1.6 Hz, Ar-H).

EXAMPLE 57

N,N-dimethyl-2-[5-(5-(3-(2-carbamoylamino)ethyl-1,2,4-oxadiazol)yl)-1H-indol-3-yl]ethylamine

Sesquioxalate

Carbonyl diimidazole (0.26 g, 1.6 mmol) was added to a solution of Example 55 (0.4 g, 1.53 mmol) in dry THF (20 ml), at 20° C. The solution was warmed to room temperature and stirred for 3 h. NH$_3$(g) was then bubbled through the solution for 8 h. The solvent was removed under vacuum and the residue chromatographed on silica-gel eluting with CH$_2$Cl$_2$/EtOH/NH$_3$ (60:8:1) to give the title-urea. The sesquioxalate salt was prepared: mp 81°-82° C.; (Found: C, 49.25; H, 5.44; N, 16.42. C$_{17}$H$_{22}$N$_6$O$_2$.1.7(C$_2$H$_2$O$_4$).0.5 (MeOH) requires C, 49.08; H, 5.40; N, 16.43%).

EXAMPLE 58

N,N-Dimethyl-2-[5-(5-(3-(2-N-methyl carbamoyl amino)ethyl-1,2,4-oxadiazol)yl)-1H-indol-3-yl]ethyl amine

Oxalate

To a solution of Example 55 (0.5 g, 1.67 mmol) in CH$_2$Cl$_2$ (30 ml) was added dropwise a solution of methyl isocyanate (0.105 g, 1.84 mmol) in CH$_2$Cl$_2$ (10 ml), at room temperature. The solution was stirred for 1 h before removing the solvent under vacuum and preparing the oxalate salt of the product obtained: mp 185°-188° C.; (Found: C, 53.27; H, 5.92; N, 18.66. C$_{18}$H$_{24}$N$_6$O$_2$.C$_2$H$_2$O$_4$.0.25H$_2$O requires C, 53.27; H, 5.92; N, 18.64%).

EXAMPLE 59

N,N-Dimethyl-2-[5-(5-(3-(2-methoxycarbonylamino)ethyl-1,2,4-oxadiazol)yl)-1H-indol-3-yl]ethylamine

Oxalate

To a solution of Example 55 (0.14 g, 0.45 mmol) in dry CH$_2$Cl$_2$ (7 ml), at 0° C., was added triethylamine (0.60 ml) and methylchloroformate (0.33 ml). The reaction mixture was allowed to warm to room temperature and stir for 16 h. Basic workup afforded a crude product which was purified by chromatography on silica-gel eluting with CH$_2$Cl$_2$MeOH/NH$_3$ (80:16:1). The oxalate salt was prepared from the product thus obtained: mp 175°-181° C.; (Found: C, 53.28; H, 5.46; N, 15.45. C$_{18}$H$_{23}$N$_5$O$_3$.C$_2$H$_2$O$_4$.0.1H$_2$O requires C, 53.47; H, 5.65; N, 15.59%).

EXAMPLE 60

N,N-Dimethyl-2-[5-(5-(3-(2-ethoxycarbonylamino)ethyl-1,2,4-oxadiazol)yl)-1H-indol-3-yl]ethylamine

Oxalate

Prepared from the amine, Example 55, using ethylchloroformate as described for Example 59. The oxalate salt was prepared: mp 169°-172° C.; (Found: C, 54.09; H, 5.91; N, 14.94. C$_{19}$H$_{25}$N$_5$O$_3$.C$_2$H$_2$O$_4$.0.2H$_2$O requires C, 54.23; H, 5.94; N, 15.06%).

EXAMPLE 61

N,N-Dimethyl-2-[5-(2-(5-(3-amino-1,2,4-oxadiazol)yl)ethyl)-1H-indol-3-yl]ethylamine

Oxalate

Prepared from N,N-dimethyl-2-(5-(2-(carboethoxy)ethyl)-1H-indol-3-yl)ethylamine and hydroxyguanidine sulphate as described for Example 6. The oxalate salt was prepared: mp 164°-167° C.; (Found: C, 55.07; H, 5.74; N, 17.81. C$_{16}$H$_{21}$N$_5$O.1.1 (C$_2$H$_2$O$_4$) requires C, 54.87; H, 5.87; N, 17.58%); δ(360 MHz, D$_2$O) 2.89 (6H, s, 2 of CH$_3$); 3.21-3.14 (6H, m, 3 of CH$_2$); 3.42 (2H, t, J=7.3 Hz, CH$_2$); 7.12 (1H, dd, J=1.6 and 8.4 Hz, Ar-H); 7.30 (1H, s, Ar-H); 7.38 (1H, d, J=1.6 Hz, Ar-H); 7.45 (1H, d, J=8.4 Hz, Ar-H).

Examples 62-82 were prepared from N,N-dimethyl-2-(5-carboethoxymethyl-1H-indol-3-yl)ethylamine and the appropriate amide oxime using the general NaOEt/EtOH procedure.

EXAMPLE 62

N,N-Dimethyl-2-[5-(5-(3-N-methylamino-1,2,4-oxadiazol)ylmethyl)-1H-indol-3-yl]ethylamine

Oxalate

The oxalate salt: mp 184° C. (EtOH/Et$_2$O); (Found: C, 55.37; H, 6.17; N, 17.62. C$_{16}$H$_{21}$N$_5$O.1.05(C$_2$H$_2$O$_4$) requires C, 55.19; H, 5.91; N, 17.78%); δ(360 MHz, D$_6$-DMSO) 2.66 (3H, d, J=5.0 Hz, NHMe); 2.78 (6H, s, 2 of CH$_3$); 3.03 (2H, m, CH$_2$); 3.23 (2H, m, CH$_2$); 4.15 (2H, s, CH$_2$); 6.54 (1H, q, J=5.0 Hz, NHMe); 7.02 (1H, d, J=8.3 Hz, Ar-H); 7.24 (1H, s, Ar-H); 7.32 (1H, d, J=8.3 Hz, Ar-H); 7.51 (1H, s, Ar-H); 10.98 (1H, s, indole NH).

EXAMPLE 63

N,N-Dimethyl-2-[5-(5-(3-(4-carbamoylbenzyl)-1,2,4-oxadiazol)ylmethyl)-1H-indol-3-yl]ethylamine

Oxalate

Monohydrate

The oxalate monohydrate salt: mp 98°-101° C.; (Found: C, 58.95; H, 5.66; N, 13.78. C$_{23}$H$_{25}$N$_5$O$_2$.C$_2$H$_2$O$_4$.0.9H$_2$O requires C, 58.90; H, 5.69; N, 13.74%); δ(360 MHz, D$_2$O) 2.82 (6H, s, 2 of CH$_3$); 3.04 (2H, t, J=7.5 Hz, CH$_2$); 3.31 (2H, t, J=7.5 Hz, CH$_2$); 4.01 (2H, s, CH$_2$); 4.28 (2H, s, CH$_2$); 7.08 (1H, dd, J=1.4 and 8.4 Hz, Ar-H); 7.22 (2H, d, J=8.2 Hz, Ar-H); 7.24 (1H, s, Ar-H); 7.39 (1H, d, J=8.4 Hz, Ar-H); 7.48 (1H, d, J=1.4 Hz, Ar-H); 7.58 (2H, d, J=8.2 Hz, Ar-H).

EXAMPLE 64

N,N-Dimethyl-2-[5-(5-(3-(4-acetylaminobenzyl)-1,2,4-oxadiazol)ylmethyl)-1H-indol-3-yl]ethylamine.

Oxalate

Hemihydrate

The oxalate hemihydrate salt: mp 98°-102° C.; (Found: C, 60.26; H, 5.72; N, 13.48. C$_{24}$H$_{27}$N$_5$O$_2$.C$_2$H$_2$O$_4$.0.6H$_2$O requires C, 60.24; H, 5.87; N, 13.51%); δ(360 MHz, D$_2$O) 2.11 (3H, s, CH$_3$); 2.77 (6H, s, 2 of CH$_3$); 2.99 (2H, t, J=7.6 Hz, CH$_2$); 3.25 (2H, t, J=7.6 Hz, CH$_2$); 3.89 (2H, s, CH$_2$); 4.23 (2H, s, CH$_2$); 7.06 (1H, dd, J=1.5 and 8.4 Hz, Ar-H); 7.10 (2H, d, J=8.5 Hz, Ar-H); 7.22 (2H, d, J=8.5 Hz, Ar-H); 7.23 (1H, s, Ar-H); 7.39 (1H, d, J=8.4 Hz, Ar-H); 7.41 (1H, s, Ar-H).

EXAMPLE 65

N,N-Dimethyl-2-[5-(5-(3-(4-methylaminosulphonylbenzyl)-1,2,4-oxadiazol)ylmethyl)-1H-indol-3-yl]ethylamine Oxalate The oxalate salt: mp 160°-164° C.; (Found: C, 54.89; H, 5.48; N, 12.76. $C_{23}H_{27}N_5SO_3.C_2H_2O_4$ requires C, 55.24; H, 5.38; N, 12.88%).

EXAMPLE 66

N,N-Dimethyl-2-[5-(5-(3-(4-carbamoylaminobenzyl)-1,2,4-oxadiazol)ylmethyl)-1H-indol-3-yl]ethylamine Oxalate Monohydrate The oxalate monhydrate salt: mp 176°-177° C.; (Found: C, 57.10; H, 6.04; N, 15.97. $C_{23}H_{26}N_6O_2.C_2H_2O_4.1.0H_2O$ requires C, 57.03; H, 5.74; N, 15.96%).

EXAMPLE 67

N,N-Dimethyl-2-[5-(5-(3-(4-methylsulphonylaminobenzyl-1,2,4-oxadiazol)ylmethyl)-1H-indol-3-yl]ethylamine Oxalate The oxalate salt: mp 156°-159° C.; (Found: C, 54.64; H, 5.35; N, 12.70; S, 6.13. $C_{23}H_{27}N_5SO_3.C_2H_2O_4.0.25H_2O$ requires C, 54.78; H, 5.43; N, 12.78; S, 5.85%).

EXAMPLE 68

N,N-Dimethyl-2-[5-(5-(3-(4-N-methylcarbamoylphenyl)-1,2,4-oxadiazol)ylmethyl)-1H-indol-3-yl]ethylamine Oxalate Hemihydrate The oxalate hemihydrate salt: mp 205°-207° C.; (Found: C, 59.65; H, 5.71; N, 14.22. $C_{23}H_{25}N_5O_2.C_2H_2O_4.0.5H_2O$ requires C, 59.75; H, 5.62; N, 13.94%); δ(360 MHz, $D_2O$) 2.83 (6H, s, 2 of $CH_3$); 2.89 (3H, s, $CH_3$); 3.01 (2H, t, J=7.6 Hz, $CH_2$); 3.29 (2H, t, J=7.6 Hz, $CH_2$); 4.14 (2H, s, $CH_2$); 6.98 (1H, d, J=8.4 Hz, Ar-H); 7.19 (1H, s, Ar-H); 7.34 (1H, d, J=8.4 Hz, Ar-H); 7.44 (1H, s, Ar-H); 7.60 (2H, d, J=8.4 Hz, Ar-H); 7.68 (2H, d, J=8.4 Hz, Ar-H).

EXAMPLE 69

N,N-Dimethyl-2-[5-(5-(3-acetylaminomethyl-1,2,4-oxadiazol)ylmethyl)-1H-indol-3-yl]ethylamine Succinate Hemihydrate The succinate hemihydrate salt: mp 165° C.; (Found: C, 56.94; H, 6.71; N, 14.57. $C_{15}H_{23}N_5O_2.C_4H_6O_4.0.4H_2O$ requires C, 56.62; H, 6.44; N, 15.01%); δ(360 MHz, $D_2O$) 2.04 (3H, s, $CH_3$); 2.92 (6H, s, 2 of $CH_3$); 3.23 (2H, t, J=7.3 Hz, $CH_2$); 3.48 (2H, t, J=7.3 Hz, $CH_2$); 4.41 (2H, s, $CH_2$); 4.46 (2H, s, $CH_2$); 7.21 (1H, dd, J=1.6 and 8.4 Hz, Ar-H); 7.35 (1H, s, Ar-H); 7.51 (1H, d, J=8.4 Hz, Ar-H); 7.63 (1H, s, Ar-H).

EXAMPLE 70

N,N-Dimethyl-2-[5-(5-(3-methylsulphonylaminomethyl-1,2,4-oxadiazol)ylmethyl)-1H-indol-3-yl]ethylamine Oxalate Hemihydrate The oxalate hemihydrate salt: mp 148°-150° C.; (Found: C, 47.90; H, 5.52; N, 14.37. $C_{17}H_{23}N_5SO_3.C_2H_2O_4.0.6H_2O$ requires C, 47.71; H, 5.52; N, 14.64%).

EXAMPLE 71

N,N-Dimethyl-2-[5-(5-(3-carbamoylmethyl-1,2,4-oxadiazol)ylmethyl)-1H-indol-3-yl]ethylamine Oxalate The oxalate salt: mp 210° C. (dec.); (Found: C, 53.55; H, 5.38; N, 15.83. $C_{13}H_{21}N_4O_2.1.2(C_2H_2O_4)$ requires C, 53.51; H, 5.42; N, 16.08%); δ(360 MHz, $D_2O$) 2.90 (6H, s, 2 of $CH_3$); 3.21 (2H, t, J=7.3 Hz, $CH_2$); 3.47 (2H, t, J=7.3 Hz, $CH_2$); 3.80 (2H, s, $CH_2$); 4.43 (2H, s, $CH_2$); 7.22 (1H, dd, J=1.6 and 8.4 Hz, Ar-H); 7.34 (1H, s, Ar-H); 7.51 (1H, d, J=8.4 Hz, Ar-H); 7.63 (1H, d, J=1.6 Hz, Ar-H).

EXAMPLE 72

N,N-Dimethyl-2-[5-(5-(3-methylsulphonylaminobenzyl)-1,2,4-oxadiazol)ylmethyl)-1H-indol-3-yl]ethylamine Oxalate The oxalate salt: mp 95°-97° C. (EtOH/$Et_2O$): (Found: C, 55.28; H, 5.58; N, 12.72%. $C_{23}H_{27}N_5SO_3.C_2H_2O_4$ requires C, 55.14; H, 5.55; N, 12.86%); δ(360 MHz, $D_2O$) 2.86 (6H, s, $NMe_2$); 2.87 (3H, s, $MeSO_2$); 3.13 (2H, t, J32 7.3 Hz, $CH_2$); 3.39 (2H, t, J=7.3 Hz, $CH_2$); 4.03 (2H, s, $CH_2$); 4.31 (2H, s, $CH_2$); 7.07-7.14 (4H, m, Ar-H); 7.29-7.34 (2H, m, Ar-H); 7.43 (1H, d, J=8.4 Hz, Ar-H); 7.52 (1H, s, Ar-H).

EXAMPLE 73

N,N-Dimethyl-2-[5-(5-(3-(3-acetylaminobenzyl)-1,2,4-oxadiazol)ylmethyl)-1H-indol-3-yl]ethylamine Oxalate The oxalate salt: mp 92°-96° C. (EtOH/$Et_2O$); (Found: C, 61.72; H, 6.02; N, 13.60. $C_{24}H_{27}N_5O_2.C_2H_2O_4$ requires C, 61.53; H, 5.76; N, 13.80%).

EXAMPLE 74

N,N-Dimethyl-2-[5-(5-(3-(4-carbamoylphenyl)-1,2,4-oxadiazol)ylmethyl)-1H-indol-3-yl]ethylamine Oxalate The oxalate salt: mp 217°-219° C.; (Found: C, 59.15; H, 5.38; N, 14.23. $C_{22}H_{23}N_5O_2.1.2(C_2H_2O_4)$ requires C, 58.91; H, 5.15; N, 14.08%).

EXAMPLE 75

N,N-Dimethyl-2-[5-(5-(3-(3-carbamoylphenyl)-1,2,4-oxadiazol)ylmethyl)-1H-indol-3-yl]ethylamine Oxalate The oxalate salt: mp 109°-111° C.; (Found: C, 59.46; H, 5.41; N, 14.40. $C_{22}H_{23}N_5O_2$ requires C, 59.50; H, 5.20; N, 14.33%).

EXAMPLE 76

N,N-Dimethyl-2-[5-(5-(3-(4-methylsulphonylaminophenyl)-1,2,4-oxadiazol)ylmethyl)-1H-indol-3-yl]ethylamine Oxalate The oxalate salt: mp 213°–215° C.; (Found: C, 55.03; H, 5.91; N, 12.44. $C_{22}H_{25}N_5SO_3 \cdot C_2H_2O_4 \cdot 0.4$ ($Et_2O$) requires C, 54.98; H, 5.59; N, 12.52%).

EXAMPLE 77

N,N-Dimethyl-2-[5-(5-(3-(4-methylaminosulphonylmethylphenyl)-1,2,4-oxadiazol)ylmethyl)-1H-indol-3-yl]ethylamine Oxalate The oxalate salt: mp 190°–192° C.; (Found: C, 55.03; H, 5.77; N, 12.36. $C_{23}H_{27}N_5SO_3 \cdot C_2H_2O_4 \cdot 0.5$ (EtOH) requires C, 55.11; H, 5.69; N, 12.36%).

EXAMPLE 78

N,N-Dimethyl-2-[5-(5-(3-(3-methylaminosulphonylmethylphenyl)-1,2,4-oxadiazol)ylmethyl)-1H-indol-3-yl]ethylamine Oxalate 0.3 Hydrate The oxalate salt: mp 199°–210° C.; (Found: C, 54.54; H, 5.41; N, 12.65; S, 5.80. $C_{23}H_{27}N_5SO_3 \cdot C_2H_2O_4 \cdot 0.3H_2O$ requires C, 54.69; H, 5.43; N, 12.76; S, 6.01%).; δ (360 MHz, $D_2O$) 2.69 (3H, s, $CH_3$); 2.87 (6H, s, 2 of $CH_3$); 3.17 (2H, t, J=7.5 Hz, $CH_2$); 3.43 (2H, t, J=7.5 Hz, $CH_2$); 4.42 (2H, s, $CH_2$); 4.48 (2H, s, $CH_2$); 7.23 (1H, d, J=8.5 Hz, Ar—H); 7.30 (1H, s, Ar—H); 7.49 (1H, d, J=8.4 Hz, Ar—H); 7.53–7.57 (2H, m, Ar—H); 7.63 (1H, s, Ar—H); 7.90–7.92 (2H, m, Ar—H).

EXAMPLE 79

N,N-Dimethyl-2-[5-(5-(3-(4-aminosulphonylmethylphenyl)-1,2,4-oxadiazol)ylmethyl)-1H-indol-3-yl]ethylamine Oxalate 1.5 Hydrate The oxalate hydrate salt: mp 210°–212° C.; (Found: C, 51.72; H, 5.43; N, 12.49. $C_{22}H_{25}N_5SO_3 \cdot C_2H_2O_4 \cdot 1.5H_2O$ requires C, 51.76; H, 5.34; N, 12.39%).

EXAMPLE 80

N,N-Dimethyl-2-[5-(5-(3-(4-dimethylaminosulphonylmethylphenyl)-1,2,4-oxadiazol)ylmethyl)-1H-indol-3-yl]ethylamine Oxalate 0.25 Hydrate The oxalate 0.25 hydrate salt: mp 208°–210° C.; (Found: C, 56.63; H, 5.74; N, 12.91. $C_{24}H_{29}N_5SO_3 \cdot 0.75(C_2H_2O_4) \cdot 0.25H_2O$ requires, C, 56.76; H, 5.79; N, 12.98%).

EXAMPLE 81

N,N-Dimethyl-2-[5-(5-(3-t-butyloxycarbonylaminomethyl-1,2,4-oxadiazol)ylmethyl)-1H-indol-3-yl]ethylamine Oxalate 0.25 Hydrate The oxalate 0.25 hydrate salt: mp 155°–156° C.; (Found: C, 54.64; H, 6.16; N, 13.34. $C_{21}H_{29}N_5O_3 \cdot 1.25(C_2H_2O_4) \cdot 0.25H_2O$ requires C, 54.64; H, 6.24; N, 13.56%); δ (360 MHz, $D_2O$) 1.38 (9H, br s, 3 of $CH_3$); 2.91 (6H, s, 2 of $CH_3$); 3.21 (2H, t, J=7.4 Hz, $CH_2$); 3.47 (2H, t, J=7.4 Hz, $CH_2$); 4.31 (2H, br s, $CH_2$); 4.40 (2H, s, $CH_2$); 7.20 (1H, d, J=8.4 Hz, Ar—H); 7.34 (1H, s, Ar—H); 7.49 (1H, d, J=8.4 Hz, Ar—H); 7.63 (1H, s, Ar—H).

EXAMPLE 82

N,N-Dimethyl-2-[5-(5-(3-(2-t-butyloxycarbonylamino)ethyl-1,2,4-oxadiazol)ylmethyl)-1H-indol-3-yl]ethylamine Oxalate 0.25 Hydrate The oxalate 0.25 hydrate salt: mp 137°–142° C.; (Found: C, 56.64; H, 6.84; N, 13.69. $C_{22}H_{31}N_5O_3 \cdot C_2H_2O_4 \cdot 0.2H_2O$ requires C, 56.84; H, 6.64; N, 13.81%).

EXAMPLE 83

N,N-Dimethyl-2-[5-(5-(3-aminomethyl-1,2,4-oxadiazol)ylmethyl)-1H-indol-3-yl]ethylamine Oxalate Prepared from Example 81 using the procedure described for Example 55. The oxalate salt mp: 109°–110° C.; m/e 300 (M$^+$+1); δ (360 MHz, $D_2O$) 2.92 (6H, s, 2 of $CH_3$); 3.24 (2H, t, J=7.3 Hz, $CH_2$); 3.50 (2H, t, J=7.3 Hz, $CH_2$); 4.37 (2H, s, $CH_2$); 4.48 (2H, s, $CH_2$); 7.23 (1H, d, J=8.4 Hz, Ar—H); 7.36 (1H, s, Ar—H); 7.53 (1H, d, J=8.4 Hz, Ar—H); 7.67 (1H, s, Ar—H).

EXAMPLE 84

N,N-Dimethyl-2[5-(5-(3-methoxycarbonylaminoethyl-1,2,4-oxadiazol)ylmethyl)-1H-indol-3-yl]ethylamine Oxalate Prepared from Example 83 using the procedure described for Example 59. The oxalate salt was prepared: mp 132°–133° C.; (Found: C, 53.50; H, 5.62; N, 15.46. $C_{18}H_{23}N_5O_3 \cdot C_2H_2O_4$ requires C, 53.67; H, 5.63; N, 15.65%); δ (360 MHz, $D_2O$) 2.90 (6H, s, 2 of $CH_3$); 3.21 (2H, t, J=7.4 Hz, $CH_2$); 3.46 (2H, t, J=7.4 Hz, $CH_2$); 3.66 (3H, s, $CH_3$); 4.29 (2H, s, $CH_2$); 4.40 (2H, s, $CH_2$); 7.19 (1H, dd, J=1.3 and 8.4 Hz, Ar—H); 7.34 (1H, s, Ar—H); 7.50 (1H, d, J=8.4 Hz, Ar—H); 7.62 (1H, s, Ar—H).

EXAMPLE 85

N,N-Dimethyl-2[5-(5-(3-N,N-dimethylaminomethyl-1,2,4-oxadiazol)ylmethyl)-1H-indol-3-yl]ethylamine Succinate Hemihydrate Prepared from Example 83 using the N-dimethylation procedure described for Example 2. The succinate hemihydrate salt was prepared: mp 135°–137° C.; (Found: C, 57.83; H, 7.19; N, 15.16. $C_{18}H_{25}N_5O \cdot 1.1(C_4H_6O_4) \cdot 0.5H_2O$ requires C, 57.69; H, 7.05; N, 15.02%); δ

(360 MHz, D$_2$O) 2.86 (6H, s, 2 of CH$_3$); 2.94 (6H, s, 2 of CH$_3$); 3.26 (2H, t, J=7.4 Hz, CH$_2$); 3.51 (2H, t, J=7.4 Hz, CH$_2$); 4.38 (2H, s, CH$_2$); 4.51 (2H, s, CH$_2$); 7.25 (1H, d, J=8.4 Hz, Ar—H); 7.38 (1H, s, Ar—H); 7.54 (1H, d, J=8.4 Hz, Ar—H); 7.70 (1H, s, Ar—H).

EXAMPLE 86

N,N-Dimethyl-2-[5-(5-(3-(2-methylsulphonylamino)ethyl-1,2,4-oxadiazol)ylmethyl)-1H-indol-3-yl]ethylamine Oxalate Prepared from Example 82 using the procedures described for the preparation of Examples 55 and 56. The oxalate salt was prepared: mp 163°–164° C. (isopropyl alcohol/ether); (Found: C, 49.72; H, 5.74; N, 14.37. C$_{18}$H$_{25}$N$_5$SO$_3$.C$_2$H$_2$O$_4$ requires C, 49.89; H, 5.65; N, 14.54%) δ(360 MHz, D$_2$O) 2.90 (6H, s, 2 of CH$_3$); 2.92 (3H, s, CH$_3$); 2.96 (2H, t, J=6.4 Hz, CH$_2$); 3.21 (2H, t, J=6.4 Hz, CH$_2$); 3.44–3.49 (4H, m, 2 of CH$_2$); 4.40 (2H, s, CH$_2$); 7.21 (1H, dd, J=1.4 and 8.5 Hz, Ar-H); 7.34 (1H, s, Ar-H); 7.50 (1H, d, J=8.5 Hz, Ar-H); 7.62 (1H, s, Ar-H).

EXAMPLE 87

N,N-Dimethyl-2-[5-(5-(3-(2-ethoxycarbonylamino)ethyl-1,2,4-oxadiazol)ylmethyl)-1H-indol-3-yl]ethylamine Oxalate Prepared from Example 82 using the procedures described for the preparation of Examples 55 and 60. The oxalate salt was prepared: mp 120°–124° C.; (Found: C, 54.90; H, 6.29; N, 14.62. C$_{20}$H$_{27}$N$_5$O$_3$.C$_2$H$_2$O$_4$.0.2H$_2$O requires C, 55.15; H, 6.19; N, 14.62%).

EXAMPLE 88

N,N-Dimethyl-2-[5-(5-(3-phenylcarboxamidomethyl-1,2,4-oxadiazol)ylmethyl)-1H-indol-3-yl]ethylamine Succinate Monohydrate Benzoyl chloride (0.14 ml) was added to a solution of Example 83 (0.35 g, 1.2 mmol) in THF (10 ml) and pyridine (0.1 ml), at −20° C. The mixture was allowed to warm to room temperature and stir for 16 h before removing the solvents and chromatographing on silica-gel using CH$_2$Cl$_2$/EtOH/NH$_3$ (60:8:1) as eluant. The succinate salt was prepared: mp 72°–74° C.; (Found: C, 60.70; H, 6.14; N, 13.76. C$_{23}$H$_{25}$N$_5$O$_2$.0.8 (C$_4$H$_6$O$_4$).1.05H$_2$O requires C, 60.77; H, 6.22; N, 13.52%).

EXAMPLE 89

N,N-Dimethyl-2-[5-(5-(3-(2-phenylcarboxamido)ethyl-1,2,4-oxadiazol)ylmethyl)-1H-indol-3yl]ethylamine Oxalate Prepared from example 82 using the procedures described for the preparation of examples 55 and 88. The oxalate salt was prepared: mp 157°–164° C.; (Found: C, 61.56; H, 6.06; N, 13.59. C$_{24}$H$_{27}$N$_5$O$_2$.C$_2$H$_2$O$_4$ requires C, 61.53; H, 5.76; N, 13.80%).

EXAMPLE 90

N,N-Dimethyl-2-[5-(5-(3-(2-n-phenylcarbamoylamino)ethyl-1,2,4-oxadiazol)ylmethyl)-1h-indol-3-yl]ethylamine Oxalate 0.3 Hydrate To a stirred solution of n,n-dimethyl-2-[5-(5-(3-(2-amino)ethyl-1,2,4-oxadiazol)ylmethyl)-1H-indol-3-yl]ethylamine (0.15 g, 0.47 mmol) in CH$_2$CL$_2$ (10 ML) at 0° C. was added phenyl isocyanate (56.0 μl, 0.5 mmol), dropwise. The solution was warmed to room temperature and stirred for 1H before removing the solvent under vacuum and purifying the residue by chromatography on silica-gel eluting with CH$_2$Cl$_2$/MeOH/NH$_3$ (40:8:1). The oxalate salt was prepared: mp 155°–162° C; (Found: C, 59.10; H, 5.77; N, 15.67.C$_{24}$H$_{28}$N$_6$O$_2$.C$_2$H$_2$O$_4$.0.3H$_2$O requires C, 59.15; H, 5.84; N, 15.92%).

EXAMPLE 91

N,N-Dimethyl-2-[5-(5-(3-(2-N-$^t$butylcarbamoylamino)ethyl-1,2,4-oxadiazol)ylmethyl)-1H-indol-3-yl]ethylamine Oxalate Hemihydrate Prepared from Example 82 using the procedures described for the preparation of Examples 55 and 90, using $^t$-butylisocyanate. The oxalate hemihydrate salt was prepared: mp 135°–140° C.; (Found: C, 56.21; H, 6.99; N, 16.27. C$_{22}$H$_{32}$N$_6$O$_2$.C$_2$H$_2$O$_4$.0.5H$_2$O requires C, 56.35; H, 6.90; N, 16.43%).

EXAMPLE 92

N-Methyl-2-[5-(5-(3-amino-1,2,4-oxadiazol)ylmethyl)-1H-indol-3-yl]ethylamine

Hemisuccinate

Hemihydrate

1. N-Benzyl-2-[5-carboethoxymethyl-1H-indol-3-yl]ethylamine

To a solution of 2-[5-carboethoxymethyl-1H-indol-3-yl]ethylamine (2.8 g, 11.37 mmol) in EtOH (45 ml) was added freshly distilled benzaldehyde (1.21 g, 11.37 mmol) and the resulting solution was stirred at room temperature for 22 h. NaBH$_4$ (0.434 g, 11.48 mmol) was added portionwise over 10 min at room temperature and the resulting mixture was stirred for a further 0.5 h before the solvent was removed under vacuum. The resulting residue was taken up into water (20 ml) and acidified with 1N HCl (30 ml). The mixture was then basified with 2N NaOH and extracted with EtOAc (4×70 ml). The combined organic phases were washed with brine (50 ml), dried and concentrated. Chromatography of the residue on silica-gel eluting with CH$_2$Cl$_2$/EtOH (90:10) gave the title-product (2.78 g, 73%); δ(360 MHz, CDCl$_3$) 1.25 (3H, t, J=7.1 Hz, CH$_3$); 2.98 (4H, s, 2 of CH$_2$); 3.68 (2H, s, CH$_2$); 3.81 (2H, s, CH$_2$); 4.14 (2H, q, J=7.1 Hz, CH$_2$); 6.98 (1H, d, J=2.2 Hz, Ar-H); 7.11 (1H, dd, J=1.6 and 8.3 Hz, Ar-H); 7.20–7.32 (6H, m, Ar-H); 7.49 (1H, d, J=0.7 Hz, Ar-H); 7.99 (1H, br s, indole N-H).

2. N-Methyl-N-benzyl-2-[5-carboethoxymethyl-1H-indol-3-yl]ethylamine

To a stirred solution of the preceding amine (2.7 g, 8.02 mmol) in anhydrous DMF (80 ml) was added K$_2$CO$_3$ (2.06 g, 14.92 mmol) followed by dimethylsulphate (0.82 ml, 8.67 mmol). The mixture was stirred at room temperature for 4 h before adding H$_2$O (150 ml) and extracting with EtOAc (2×125 ml). The combined organic solutions were washed with brine (50 ml), dried (Na$_2$SO$_4$) and concentrated. The residue was purified by flash chromatography on silica-gel eluting with CH$_2$Cl$_2$/EtOH (90:10). The product (1.7 g, 61%) was obtained as a colourless oil; δ(250 MHz, CDCl$_3$) 1.25 (3H, t, J=7.1 Hz, CH$_3$); 2.33 (3H, s, CH$_3$); 2.71–2.78 (2H, m, CH$_2$); 2.93–3.00 (2H, m, CH$_2$); 3.60 (2H, s, CH$_2$); 3.68 (2H, s, CH$_2$); 4.15 (2H, q, J=7.1 Hz, CH$_2$); 6.99 (1H, br s, Ar-H); 7.11 (1H, dd, J=1.7 and 8.4 Hz, Ar-H); 7.23–7.36 (6H, m, Ar-H); 7.41 (1H, s, Ar-H); 7.93 (1H, br, s, indole N-H).

3. N-Methyl-2-[5-carboethoxymethyl-1H-indol-3-yl]ethylamine

A solution of the preceding benzylamine (1.6 g) in ethanol (140 ml) was hydrogenated at 1 atm over 10% Pd/C (1 g) for 1 h. The catalyst was removed by filtration, washed with EtOH (2×50 ml) and the solvents were removed under vacuum to give the title-N-methylamine (1.12 g); δ(250 MHz, CDCl$_3$) 1.25 (3H, t, J=7.1 Hz, CH$_3$); 2.44 (3H, s, CH$_3$); 2.86–2.99 (4H, m, 2 of CH$_2$); 3.70 (2H, s, CH$_2$); 4.15 (2H, q, J=7.1 Hz, CH$_2$); 7.02 (1H, d, J=2.0 Hz, Ar-H); 7.12 (1H, dd, J=1.6 and 8.4 Hz, Ar-H); 7.30 (1H, d, J=8.4 Hz, Ar-H); 7.52 (1H, s, Ar-H); 8.08 (1H, br s, indole N-H).

4. N-Methyl-2-[5-(5-(3-amino-1,2,4-oxadiazol)yl methyl)-1H-indol-3-yl]ethylamine Hemisuccinate Hemihydrate The title -compound was prepared from N-methyl-2-[5-carboethoxymethyl-1H-indol-3-yl]ethylamine and hydroxyguanidine sulphate as described for Example 6. The hemisuccinate hemihydrate salt was prepared: mp 75°–79° C. (EtOH/Et$_2$O); (Found: C, 55.64; H, 6.62; N, 19.27%. C$_{14}$H$_{17}$N$_5$O.0.65(C$_4$H$_6$O$_4$).0.13(C$_2$H$_6$O).0.6-H$_2$O requires C, 55.50; H, 6.32; N, 19.19%); δ(360 MHz, D$_6$-DMSO) 2.47 (3H, s, CH$_3$); 2.87∝3.00 (4H, m, 2 of CH$_2$); 4.13 (2H, s, CH$_2$); 6.13 (2H, br s, NH$_2$); 7.01 (1H, dd, J=1.5 and 8.3 Hz, Ar-H); 7.19 (1H, d, J=1.8 Hz, Ar-H); 7.31 (1H, d, J=8.3 Hz, Ar-H); 7.48 (1H, s, Ar-H); 10.89 (1H, br s, indole N-H).

EXAMPLE 93

N,N-Dimethyl-2-[5-(5-(3-(4-$t$-butyloxycarbonyl)piperazine-1,4-yl-1,2,4-oxadiazol)ylmethyl)-1H-indol-3-yl]ethylamine Oxalate Prepared from 4-$t$-butyloxycarbonyl-piperazine amide oxime and N,N-dimethyl-2-(5-carboethoxymethyl-1H-indol-3-yl)ethylamine using the general procedure. The oxalate salt was prepared: mp 179°–180° C.; (Found: C, 56.48; H, 6.56; N, 14.87. C$_{24}$H$_{34}$N$_6$O$_3$. 1.2 (C$_2$H$_2$O$_4$) requires C, 56.36; H, 6.52; N, 14.94%); δ(360 MHz, D$_2$O) 1.44 (9H, s, 3 of CH$_3$); 2.89 (6H, s, 2 of CH$_3$); 3.20 (2H, t, J=7.3 Hz, CH$_2$); 3.30–3.33 (4H, m, 2 of CH$_2$); 3.43–3.48 (6H, m, 3 of CH$_2$); 4.25 (2H, s, CH$_2$); 7.18 (1H, d, J=8.3 Hz, Ar-H); 7.33 (1H, s, Ar-H); 7.49 (1H, d, J=8.3 Hz, Ar-H); 7.60 (1H, s, Ar-H).

EXAMPLE 94

N,N-Dimethyl-2-[5-(5-(3-(4-methylsulphonyl)piperazin-1,4-yl-1,2,4-oxadiazol)ylmethyl)-1H-indol-3-yl]ethylamine Oxalate Prepared from Example 93 using the procedures described for Examples 55 and 56. The oxalate salt was prepared: mp 191°–192° C.; (Found: C, 50.56; H, 5.70; N, 15.78. C$_{20}$H$_{28}$N$_6$SO$_3$. C$_2$H$_2$O$_4$ requires C, 50.56; H, 5.79; N, 16.08%); δ(360 MHz, D$_2$O) 2.89 (6H, s, 2 of CH$_3$); 2.96 (3H, s, CH$_3$); 3.17–3.25 (6H, m, 3 of CH$_2$); 3.40–3.49 (6H, m, 3 of CH$_2$); 4.24 (2H, s, CH$_2$); 7.16 (1H, d, J=8.4 Hz, Ar-H); 7.33 (1H, s, Ar-H); 7.48 (1H, d, J=8.4 Hz, Ar-H); 7.60 (1H, s, Ar-H).

EXAMPLE 95

N,N-Dimethyl-2-[5-(5-(3-(4-methoxycarbonyl)piperazin-1,4-yl-1,2,4-oxadiazol)ylmethyl)-1H-indol-3-yl]ethylamine Oxalate 0.2 Hydrate Prepared from Example 93 using the procedures described for Examples 55 and 59. The oxalate salt was prepared: mp 204°–205° C.; (Found: C, 54.41; H, 5.81; N, 16.51. C$_{21}$H$_{28}$N$_6$O$_3$. C$_2$H$_2$O$_4$.0.2H$_2$O requires C, 54.58; H, 6.05; N, 16.60%).

EXAMPLE 96

N,N-Dimethyl-2-[5-(5-(3-(4-N-methylcarbomoyl)piperazin-1,4-yl-1,2,4-oxadiazol)ylmethyl)-1H-indol-3-yl]ethylamine Oxalate 0.4 Hydrate Prepared from Example 93 using the procedures described for Examples 55 and 58. The oxalate salt was prepared: mp 193°–194° C.; (Found: C, 54.27; H, 6.24; N, 19.22. C$_{21}$H$_{29}$N$_7$O$_2$. 0.4H$_2$O requires C, 54.30; H, 6.30; N, 19.13%).

EXAMPLE 97

N,N-Dimethyl-2-[5-(5-(3-(4-acetyl)piperazin-1,4-yl-1,2,4-oxadiazol)ylmethyl)-1H-indol-3-yl]ethylamine Oxalate 0.3 Hydrate The title-compound was prepared by N-acetylation with Ac$_2$O of the intermediate derived from Example 93 prepared using the procedure described for Example 55. The oxalate salt was prepared: mp 196°–197° C.; (Found: C, 56.07; H, 6.05; N, 16.91. C$_{21}$H$_{28}$N$_6$O$_2$. C$_2$H$_2$O$_4$. 0.3H$_2$O requires C, 56.16; H, 6.27; N, 17.08%).

EXAMPLE 98

N,N-Dimethyl-2-[5-(5-(3-(4-methylsulphonylaminomethyl)phenyl-1,2,4-oxadiazol)ylmethyl)-1H-indol-3-yl]ethylamine Oxalate Hemihydrate The oxalate hemihydrate salt: mp 196°–198° C.; (Found: C, 54.16; H, 5.65; N, 12.51. C$_{23}$H$_{27}$N$_5$SO$_3$. C$_2$H$_2$O$_4$. 0.5H$_2$O requires C, 54.34; H, 5.47; N, 12.67%).

EXAMPLE 99

N,N-Dimethyl-2-[5-(5-(3-phenylsulphonylaminomethyl-1,2,4-oxadiazol)ylmethyl)-1H-indol-3-yl]ethylamine

Sesquioxalate

The sesquioxalate salt: mp 88°–90° C.; (Found: C, 52.16; H, 5.15; N, 12.26. $C_{22}H_{25}N_5SO_3$. 1.5 ($C_2H_2O_4$) requires C, 52.26; H, 4.91; N, 12.19%).

EXAMPLE 100

N,N-Dimethyl-2-[5-(5-(3-N-benzylamino-1,2,4-oxadiazol)ylmethyl)-1H-indol-3-yl]ethylamine

Oxalate

0.25 Hydrate

Prepared from N-benzylamino amide oxime and N,N-dimethyl-2-(5-carboethoxymethyl-1H-indol-3-yl)ethylamine using the general NaOEt/EtOH procedure. The oxalate salt was prepared: mp 168°–169° C.; (Found: C, 61.20; H, 5.89; N, 14.93. $C_{22}H_{25}N_5O$. $C_2H_2O_4$. $0.25H_2O$ requires C, 61.33; H, 5.89; N, 14.90%).

EXAMPLE 101

N,N-Dimethyl-2-[5-(5-(3-pyrid-3-ylmethyl-1,2,4-oxadiazol)ylmethyl)-1H-indol-3-yl]ethylamine

Dihydrochloride

Monohydrate

Prepared from pyrid-3-ylmethylamideoxime and N,N-dimethyl-2-(5-carboethoxymethyl-1H-indol-3-yl)ethylamine using the general procedure. The dihydrochloride monohydrate salt: mp 150°–152° C.; (Found: C, 56.02; H, 6.01; N, 15.01. $C_{23}H_{23}N_5O$. $2HCl$. $1H_2O$. 0.1 (iPA) requires C, 55.81; H, 6.11; N, 15.28%).

EXAMPLE 102

N,N-Dimethyl-2-[5-(5-(3-(6-methoxy)pyrid-3-ylmethyl-1,2,4-oxadiazol)ylmethyl)-1H-indol-3-yl]ethylamine

Oxalate

0.25 Hydrate

The oxalate 0.25 hydrate salt: mp 146°–148° C.; (Found: C, 59.24; H, 5.70; N, 14.19. $C_{22}H_{25}N_5O_2$. $C_2H_2O_4$. $0.25H_2O$ requires C, 59.31; H, 5.70; N, 14.41%).

EXAMPLE 103

2-[5-(5-(3-(4-Acetylaminobenzyl)-1,2,4-oxadiazol)ylmethyl)-1H-indol-3-yl]ethylamine

Oxalate

The oxalate salt: mp 140° C.; (Found: C, 59.68; H, 5.68; N, 13.81. $C_{22}H_{23}N_5O_2$. $C_2H_2O_4$. 0.6 ($C_2H_5OH$) requires C, 59.65; H, 5.75; N, 13.85%).

EXAMPLE 104

2-[5-(5-(3-(4-Methylsulphonylaminobenzyl)-1,2,4-oxadiazol)ylmethyl)-1H-indol-3-yl]ethylamine

Oxalate

The oxalate salt: mp 110°–112° C.; (Found: C, 52.48; H, 5.07; N, 12.77; S, 6.14. $C_{21}H_{23}N_5SO_3$. 1.25 ($C_2H_2O_4$). 0.3 ($C_2H_5OH$) requires C, 52.46; H, 5.01; N, 12.65; S, 5.79%).

Examples 105 and 106 were prepared by reaction of 2-[5-(2-(carboethoxy)ethyl)-1H-indol-3-yl]ethylamine with the appropriate amide oxime.

EXAMPLE 105

2-[5-(2-(5-(3-(4-Acetylaminobenzyl)-1,2,4-oxadiazol)yl)ethyl)-1H-indol-3-yl]ethylamine

Oxalate

The oxalate salt: mp 121°–127° C.; (Found: C, 59.09; H, 5.56; N, 13.54. $C_{23}H_{25}N_5O_2$. 1.3 ($C_2H_2O_4$) requires C, 59.07; H, 5.34; N, 13.45%).

EXAMPLE 106

2-[5-(2-(5-(3-(4-Methoxybenzyl)-1,2,4-oxadiazol)yl)ethyl)-1H-indol-3-yl]ethylamine

Sesquioxalate

The oxalate salt: mp 136°–138° C.; (Found: C, 58.70; H, 4.85; N, 11.00. $C_{22}H_{24}N_4O_2$. 1.5 ($C_2H_2O_4$) requires C, 58.94; H, 4.95; N, 11.00%).

EXAMPLE 107

N,N-Dimethyl-2-[5-(2-(5-Methyl-1,3-oxazol)yl)-1H-indol-3-yl]ethylamine

Sesquioxalate 1. 2-[5-Carboxy-1H-indol-3-yl]N,N-dimethylethylamine

A solution of 2-[5-Carboethoxy-1H-indol-3-yl]N,N-dimethylethylamine (1.4 g, 5.4 mmol) and lithium hydroxide (0.45 g, 10.8 mmol) in ethanol (40 ml) was heated at 60° C. for 8 hours, then stirred overnight at room temperature. The ethanol was removed in vacuo and the crude residue chromatographed (eluant 20:15:5:1 ether:ethanol:water:ammonia). The acid (0.94 g, 75%) was isolated as a white solid, after precipitation with ether. δ(360 MHz, $D_6$-DMSO) 2.86 (6H, s), 3.09 (2H, t, J=7 Hz), 3.33 (2H, t, J=7 Hz), 7.22 (1H, s), 7.46 (1H, d, J=9 Hz), 7.78 (1H, dd, J=9 and 2 Hz), 8.12 (1H, s).

2. 2-[5-Propynylcarboxamido-1H-indol-3-yl]N,N-dimethylethylamine

To a solution of 2-[5-carboxy-1H-indol-3-yl]N,N-dimethylethylamine (0.2 g, 0.86 mmol), 1-hydroxybenztriazole (0.14 g, 1.0 mmol), N-methyl morpholine (0.2 ml, 1.7 mmol) and propargylamine (71 μl, 1.0 mmol) in dichloromethane:dimethyl formamide (1:1) (25 ml) at 0° C., was added 1-(3-dimethylaminopropyl)-3-ethyl-carbodiimide hydrochloride portionwise. The solution was stirred for 18 hours, then washed with water (1×50 ml). The organic layer was separated, and the aqueous layer washed with more dichloromethane (4×20 ml). The organic layers were combined and evaporated in vacuo. The crude residue was chromatographed (eluant 40:8:1 dichloromethane:ethanol:ammonia) to give the title compound (88 mg, 38%). The aqueous phase was also evaporated and chromatographed, using 40:8:1 dichloromethane:ethanol:ammonia, to give the desired alkyne (100 mg, 48%), slightly contaminated with the carbodiimide urea. δ(360 MHz, $CDCl_3$) 2.33 (7H, m), 2.65 (2H, t, J=7 Hz), 2.92 (2H, t, J=7 Hz), 4.32 (2H, dd, J=7 and 1 Hz), 6.50 (1H, brt), 7.02 (1H, s), 7.24 (1H, d, J=9 Hz), 7.54 (1H, dd, J=9 and 1 Hz), 8.09 (1H, s), 8.79 (1H, brs).

3. N,N-Dimethyl-2-[5-(2-(5-methyl-1,3-oxazol)yl)-1H-indol-3-yl]ethylamine. Sesquioxalate A solution of 2-[5-propynylcarboxamido-1H-indol-3-yl]N,N-dimethylethylamine (88 mg, 0.33 mmol) and mercuric acetate (7 mg, 0.02 mmol) in acetic acid (4 ml) was refluxed for 3 hours. After this time the solution was cooled to ambient temperature and evaporated in vacuo. Saturated potassium carbonate solution (10 ml) was added to the residue, and the mixture extracted with dichloromethane (5×20 ml). The organic layers were combined, dried (MgSO$_4$) and evaporated. The residue was chromatographed (eluant 60:8:1 dichloromethane:ethanol:ammonia) to give the oxazole (50 mg, 57%) as a pale yellow oil. The sesquioxalate salt was prepared: mp 164°-166° C. (Found: C, 55.86; H, 5.52; N, 10.07; C$_{16}$H$_{19}$N$_3$O.1.6(C$_2$H$_2$O$_4$) requires C, 55.78, H, 5.41, N, 10.16%); δ(360 MHz, D$_2$O) 2.49 (3H, s), 2.93 (6H, s), 3.25 (2H, t, J=7 Hz), 3.51 (2H, t, J=7 Hz), 7.30 (1H, s), 7.43 (1H, s), 7.61 (1H, d, J=9 Hz), 7.72 (1H, dd, J=9 and 1 Hz), 8.20 (1H, d, J=1 Hz). m/z (EI), 269 (M+), 225, 211, 181, 168, 155, 129, 115, 81, 69.

EXAMPLE 108

N,N-Dimethyl-2-[5-(2-(2-(5-methyl-1,3-oxazol)yl)ethyl)-1H-indol-3-yl]ethylamine

Tartrate

This was prepared according to the three step procedure described in the previous example using 2-[5-(2-(carboethoxy)ethyl)-1H-indol-3-yl]N,N-dimethylethylamine. mp 55°-60° C. Formula: C$_{18}$H$_{23}$N$_3$O.(C$_4$H$_6$O$_6$).0.6H$_2$O. Analysis: Calc: C, 57.66; H, 6.64; N, 9.17. Found: C, 57.94; H, 7.22; N, 8.82 δ(360 MHz, D$_2$O) δ2.06 (3H, s), 2.92 (6H, s), 3.15 (6H, m), 3.44 (2H, t, J=7 Hz), 4.39 (2H, s), 6.62 (1H, s), 7.09 (1H, dd, J=8 and 2 Hz), 7.30 (1H, s), 7.38 (1H, s), 7.43 (1H, d, J=8 Hz).

EXAMPLE 109

4-[5-(3-Amino-1,2,4-oxadiazol-5-yl)-1H-indol-3-yl]N-methylpiperidine

Oxalate

A mixture of indole-5-carboxylic acid (1.0 g, 6.2 mmol), 1-methyl-4-piperidone (1.4 ml, 11.2 mmol) and potassium hydroxide (30 ml of a 2M solution) was heated at reflux for 5 hours. The solution was then stirred overnight at room temperature after which time the solvent was evaporated in vacuo. The residue was then chromatographed (eluant 20:15:5:1 ether:ethanol:water:ammonia), to give 4-[5-carboxy-1H-indol-3-yl]N-methylpiperid-3-ene (1.0 g, 63%).

To a stirred solution of methanol:ethanol (2:1, 200 ml) at 0° C., was added, dropwise, thionyl chloride (1.1 ml, 15 mmol) under an atmosphere of nitrogen. The acid (1.0 g, 3.9 mmol) was added portionwise at 0° C., then the solution was allowed to warm to room temperature and stirred overnight. The solution was then heated at reflux for 2 hours, then allowed to cool to ambient temperature. The mixture was evaporated in vacuo to give the hydrochloride salts of the corresponding methyl:ethyl esters (2:1) (0.97 g, 80%).

The methyl:ethyl (2:1) esters of 4-[5-carboxy-1H-indol-3-yl]N-methylpiperid-3-ene hydrochloride (0.5 g, 1.6 mmol) in ethanol (50 ml) were hydrogenated at 30 p.s.i. for four hours in the presence of palladium on carbon (600 mg). After this time the catalyst was filtered off and the ethanol evaporated in vacuo. The crude residue was chromatographed using 80:8:1 dichloromethane:ethanol:ammonia, to give the methyl:ethyl (2:1) esters of 4-[5-carboxy-indol-3-yl]N-methylpiperidine (255 mg, 58%), as a viscous oil.

Sodium metal (0.19 g, 8.5 mmol) was added to a stirred suspension of hydroxyguanidine sulphate (0.57 g, 2.1 mmol) in ethanol (10 ml). After 30 minutes a solution of the above esters (255 mg, 0.91 mmol) in ethanol (5 ml) was added, and the mixture heated at reflux for 72 hours. The mixture was then cooled to ambient temperature, the solvent removed in vacuo, and the residue chromatographed (eluant 40:8:1 dichloromethane:ethanol:ammonia). The desired product, 4-[5-(3-amino-1,2,4-oxadiazol-5-yl)-1H-indol-3-yl]N-methylpiperidine (12 mg, 4.5%) was isolated as a viscous oil. Column fractions containing product and starting material were combined, evaporated and subjected to preparative thin layer chromatography (eluant 40:8:1 dichloromethane:ethanol:ammonia) to give the desired amino oxadiazole (10 mg, 3.5%) as a viscous oil. mp 186°-188° C. Formula: C$_{16}$H$_{19}$N$_5$O.1.2(CO$_2$H)$_2$. 0.8H$_2$O. Analysis: Found: C, 52.39; H, 5.55; N, 17.09 Calc. C, 52.64; H, 5.52; N, 16.68; δ(360 MHz, D$_2$O) δ1.87 (2H, m), 2.22 (2H, m), 2.94 (4H, m), 3.13 (2H, m), 3.63 (2H, m), 7.18 (1H, s), 7.38 (1H, d, J=9 Hz), 7.53 (1H, dd, J=9 and 1 Hz), 7.94 (1H, d, J=1 Hz). m/z (FAB) 298 (M+1), 185, 93, 75.

EXAMPLE 110

4-[5-(3-Amino-1,2,4-oxadiazol-5-ylmethyl)-1H-indol-3-yl]N-methylpiperidine

Oxalate

Step 1: 4-[5-Carbomethoxymethyl-1H-indol-3-yl]N-methylpiperidine

A solution of 1-methyl-4 (formylmethyl)piperidine (2.3 g, 16 mmol) and 4-(ethoxycarbonylmethyl)phenyl hydrazine hydrochloride (3.7 g, 16 mmol) in methanol:water (20:1) (25 ml) was stirred at room temperature for 1 hour. Polyphosphoric acid (7 g) was then added and the mixture heated at reflux for 5 hours, under nitrogen. The mixture was then cooled to ambient temperature, basified with saturated sodium bicarbonate to pH9, and extracted with dichloromethane (2×20 ml). The organic phases were combined, dried (MgSO$_4$) and evaporated to give a brown residue. This was chromatographed (eluant 50:8:1 dichloromethane:ethanol:ammonia) to give 4-[5-carbomethoxymethyl-1H-indol-3-yl]N-methylpiperidine (1.8 g, 39%) as a yellow solid. mp 105°-107° C. δ(360 MHz, CDCl$_3$) δ1.85 (2H, m), 2.16 (4H, m), 2.36 (3H, s), 2.81 (1H, m), 3.00 (2H, m), 3.70 (3H, s), 3.73 (2H, s), 6.97 (1H, d, J=2 Hz), 7.10 (1H, dd, J=8 and Hz), 7.31 (1H, d, J=8 Hz), 7.53 (1H, s), 7.97 (1H, brs).

Step 2: 4-[5-(3-Amino-1,2,4-oxadiazol-5-ylmethyl)-1H-indol-3-yl]N-methyl piperidine

Oxalate

Sodium (0.4 g, 17 mmol) was dissolved in ethanol (30 ml), under an atmosphere of nitrogen and to the stirred solution was added hydroxyguanidine sulphate (1.53 g, 5.8 mmol). After stirring for 20 minutes at room temperature, the ester (0.5 g, 1.7 mmol) was added portionwise, and the mixture heated at reflux for 1.5 hours. The solution was cooled to room temperature, filtered, and the filtrate evaporated in vacuo. The residue was then columned, using 50:8:1 dichloromethane:ethanol:ammonia, to give the title amino oxadiazole (313 mg, 60%). The oxalate salt was prepared: mp 116°-120° C. Formula: C$_{17}$H$_{21}$N$_5$O.1.2(CO$_2$H)$_2$.0.2H$_2$O.0.34 (C$_4$H$_{10}$O).

Analysis: Calc: C, 55.76; H, 6.12; N, 15.63. Found: C, 55.63; H, 6.31; N, 15.86. δ(360 MHz, D$_6$-DMSO) δ1.95 (2H, m), 2.10 (2H, m), 2.76 (3H, s), 3.05 (3H, m), 3.42 (2H, m), 4.13 (2H, s), 6.13 (2H, s), 7.00 (1H, d, J=8 Hz), 7.15 (1H, s), 7.31 (1H, d, J=8 Hz), 7.54 (1H, s), 10.90 (1H, s). m/z (EI) 311 (M+), 271, 156, 97, 70.

EXAMPLE 111

4-[5-(3-(4-Methylsulphonylaminobenzyl)-1,2,4-oxadiazol-5-ylmethyl)-1H-indol-3-yl]N-methylpiperidine Oxalate mp 122°-124° C.; δ(360 MHz, D$_6$-DMSO) 1.91 (2H, m), 2.08 (2H, m), 2.76 (3H, s), 3.01 (6H, m), 3.42 (2H, m), 3.99 (2H, s), 4.32 (2H, s), 7.02 (1H, dd, J=8 and 2Hz), 7.14 (3H, m), 7.23 (2H, d, J=9 Hz), 7.31 (1H, d, J=8 Hz), 7.56 (1H, s), 10.92 (1H, s).

EXAMPLE 112

4-[5-(3-(3-Pyridyl)-1,2,4-oxadiazol-5-ylmethyl)-1H-indol-3-yl]N-methylpiperidine Oxalate mp 94°-96° C. δ(360 MHz, D$_6$-DMSO) δ1.92 (2H, m), 2.10 (2H, m), 2.80 (3H, s), 3.05 (3H, m), 3.45 (2H, m), 4.11 (2H, s), 4.32 (2H, s), 7.00 (1H, d, J=8 Hz), 7.16 (1H, s), 7.31 (1H, d, J=9 Hz), 7.35 (1H, m), 7.56 (1H, s), 7.70 (1H, d, J=8 Hz), 8.46 (1H, m), 8.52 (1H, s), 10.93 (1H, s).

EXAMPLE 113

N,N-Dimethyl-2-[5-(5-(3-pyridyl-4-ylmethyl-1,2,4-oxadiazol)ylmethyl)-1H-indol-3-yl]ethylamine Oxalate Monohydrate The oxalate monohydrate salt: mp<50° C. (hygroscopic); (Found: C, 58.52; H, 5.71; N, 14.60. C$_{21}$H$_{23}$N$_5$O.1.05 (C$_2$H$_2$O$_4$).1H$_2$O requires C, 58.53; H, 5.76; N, 14.78%).

EXAMPLE 114

N,N-Dimethyl-2-[5-(5-(3-(4-$t$-butyloxycarbonyl)ethylene-1,4-amino-1,2,4-oxadiazol)ylmethyl)-1H-indol-3-yl]ethylamine Oxalate The oxalate salt: mp 120°-122° C.; (Found: C, 55.42; H, 6.59; N, 15.91. C$_{22}$H$_{32}$N$_6$O$_3$.C$_2$H$_2$O$_4$ requires C, 55.59; H, 6.61; N, 16.21%).

EXAMPLE 115

2-[5-(5-(3-(Carboxamido)-1,2,4-oxadiazol)ylmethyl)-1H-indol-3-yl]ethylamine Hydrogen Oxalate Step 1: 2-[5-(5-(3-Ethoxycarbonyl)-1,2,4-oxadiazol)ylmethyl)-1H-indol-3-yl]-N-(tert-butyloxycarbonyl)ethylamine To a solution of 2-[5-Carboxymethyl-1H-indol-3-yl]-N-(tert-butyloxycarbonyl)ethylamine (3 g, 9.4 mmol) over 4A molecular sieves (3 g), in tetrahydrofuran (100 ml) was added triethylamine (2.62 ml, 18.8 mmol). The solution was stirred under nitrogen at room temperature for 1 hour and then cooled to −10° C. Isobutylchloroformate (2.45 ml, 18.8 mmol) was added and after stirring at −10° C. for 15 minutes, a solution of (ethoxycarbonyl) formamide oxime (1.87 g, 14.2 mmol) in tetrahydrofuran (10 ml) was added. The reaction mixture was allowed to warm to room temperature and stirred for 2.5 hours. The suspension was filtered through Hyflo and the filtrate evaporated in vacuo to give a yellow solid. This was dissolved in 1,4-dioxane (25 ml) and heated to reflux over 4A molecular sieves (3 g) under nitrogen for 2 days. After filtering through Hyflo, the filtrate was evaporated in vacuo and chromatographed on silica (gradient elution 3:1 petroleum ether:ethyl acetate then 1:1 petroleum ether:ethyl acetate) to give the desired ester oxadiazole as a yellow gum (1.56 g, 40%). δ(360 MHz, CDCl$_3$) 1.42 (3H, t, J=7.1 Hz), 1.43 (9H, s), 2.92 (2H, t, J=6.8 Hz), 3.44 (2H, m), 4.40 (2H, s), 4.48 (2H, q, J=7.1 Hz), 7.04 (1H,s), 7.15 (1H, dd, J=1.6, 8.3 Hz), 7.32 (1H, d, J=8.3 Hz), 7.54 (1H, s), 8.13 (1H, s). m/z (EI), 414 (M+), 358, 297, 212, 143, 115, 91.

Step 2: 2-[5-(5-(3-(Carboxamido)-1,2,4-oxadiazol)ylmethyl)-1H-indol-3-yl]ethylamine A solution of the ester oxadiazole (0.19 g, 0.46 mmol) in ethanol (30 ml) was cooled to 0° C. (ice/water bath) and then ammonia gas was bubbled through for 15 minutes. The solvent was evaporated in vacuo to give 2-[5-(5-(3-(Carboxamido)-1,2,4-oxadiazol)ylmethyl)-1H-indol-3-yl]-N-(tert-butyloxycarbonyl)ethylamine as a yellow gum (0.17 g). The crude residue was dissolved in dry dichloromethane (20 ml) under nitrogen, cooled to 0° C. and trifluoroacetic acid (1 ml, 13.0 mmol) was added. The solution was allowed to warm to room temperature and stirred under nitrogen for 3 hours. The solvent was evaporated in vacuo and the residue was azeotroped with toluene (2×5 ml) to give a pale orange gum. This was chromatographed on silica (eluant 20:15:5:1, ether:ethanol:water:ammonia) to give the desired amide oxadiazole as a beige gum (95 mg, 72%).

The oxalate salt was prepared: m.p. 184°-186° C. Formula: C$_{14}$H$_{15}$N$_5$O$_2$.0.8 (CO$_2$H)$_2$.0.2 (CH$_3$OH). Analysis: Calc: C, 52.17; H, 4.82; N, 19.25. Found: C, 51.99; H, 5.09; N, 19.25. δ(360 MHz, D$_6$-DMSO) 2.90 (2H, t, J=6.8 Hz), 2.99 (2H, t, J=6.8 Hz), 4.44 (2H, s), 7.06 (1H, dd, J=1.4, 8.3 Hz), 7.23 (1H, s), 7.34 (1H, d, J=8.3 Hz), 7.51 (1H, s), 8.04 (1H, br s), 8.24 (1H, br s), 10.96 (1H, br s). m/z (FAB) 286 (M+1).

Examples 116-118 were prepared using the procedure described for Example 115, Step 2, using the appropriate amine.

EXAMPLE 116

2-[5-(5-(3-(N-Methylcarboxamido)-1,2,4-oxadiazol)ylmethyl)-1H-indol-3-yl]ethylamine Hydrogen Oxalate m.p. 113°-115° C.; Formula: C$_{15}$H$_{17}$N$_5$O$_2$ (CO$_2$H)$_2$.0.5 (H$_2$O).0.15 (Et$_2$O). Analysis: Calc: C, 51.62; H, 5.29; N, 17.10. Found: C, 51.58; H, 5.15; N, 17.07. δ(360 MHz, D$_6$-DMSO) 2.76 (3H, d, J=4.7 Hz), 2.96 (2H, t, J=7.1 Hz), 3.06 (2H, t, J=7.1 Hz), 4.45 (2H, s), 7.07 (1H, dd, J=1.4, 8.3 Hz), 7.25 (1H, s), 7.35 (1H, d, J=8.3 Hz), 7.51 (1H, s), 8.85 (1H, br d, J=4.5 Hz), 11.01 (1H, br s). m/z (FAB) 300 (M+1).

EXAMPLE 117

2-[5-(5-(3-(N-Pyrrolidinylcarboxamido)-1,2,4-oxadiazol)ylmethyl)-1H-indol-3-yl]ethylamine Hydrogen Oxalate m.p. 182°-185° C. δ(360 MHz, D$_6$-DMSO) 1.86 (4H, m), 2.95 (2H, t, J=7.4 Hz), 3.05 (2H, t, J=7.4 Hz), 3.47 (2H, t, J=6.9 Hz), 3.54 (2H, t, J=6.9 Hz), 4.45 (2H, s), 7.08 (1H, d, J=7.0 Hz), 7.25 (1H, s), 7.35 (1H, d, J=8.3 Hz), 7.53 (1H, s), 11.0 (1H, br s).

EXAMPLE 118

2-[5-(5-(3-(N-Azetidinylcarboxamido)-1,2,4-oxadiazol)ylmethyl)-1H-indol-3-yl]ethylamine Hydrogen Oxalate m.p. 114°-117° C.; δ(360 MHz, D₆-DMSO) 2.28 (2H, quin, J=7.8 Hz), 2.95 (2H, t, J=7.1 Hz), 3.05 (2H, t, J=7.1 Hz), 4.06 (2H, t, J=7.8 Hz), 4.40 (2H, t, J=7.8 Hz), 4.44 (2H, s), 7.07 (1H, dd, J=1.6, 8.3 Hz), 7.25 (1H, s), 7.35 (1H, d, J=8.3 Hz), 7.52 (1H, s), 11.00 (1H, br s).

EXAMPLE 119

N,N-Dimethyl-2-[5-(5-(3-(4-phenylsulphonyl)piperazin-1,4-yl-1,2,4-oxadiazol)ylmethyl)-1H-indol-3-yl]ethylamine Oxalate 0.3 Hydrate Prepared from Example 93 using the procedures described for Examples 55 and 56. The oxalate salt was prepared: mp 210°-211° C.; (Found: C, 54.15; H, 5.26; N, 13.81. $C_{25}H_{30}N_6SO_3$. 1.2 ($C_2H_2O_4$).$0.3H_2O$ requires C, 54.12; H, 5.47; N, 13.82%).

EXAMPLE 120

N,N-Dimethyl-2-[5-(5-(3-Pyrrolidinyloxy carbonylamino)ethyl-1,2,4-oxadiazol)ylmethyl)-1H-indol-3-yl]ethylamine Oxalate Hemihydrate Prepared from Example 82 using the procedures described for the preparation of Examples 55 and 57 using pyrrolidine. The oxalate hemihydrate salt was prepared: mp 132°-135° C.; (Found: C, 56.63; H, 6.23; N, 16.38. $C_{22}H_{30}N_6O.C_2H_2O_4$. $0.5H_2O$ requires C, 56.57; H, 6.53; N, 16.49%).

EXAMPLE 121

N,N-Dimethyl-2-[5-(5-(3-(4-Methylsulphonyl)ethylene-1,4-diamino-1,2,4-oxadiazol)ylmethyl)-1H-indol-3-yl]ethylamine Oxalate Hemihydrate The oxalate hemihydrate salt: mp178°-181° C.; (Found; C, 47.43; H, 5.49; N, 16.82. $C_{18}H_{26}N_6SO_3.C_2H_2O_4.0.5H_2O$ requires C, 47.52; H, 5.78; N, 16.62%).

EXAMPLE 122

N,N-Dimethyl-2-[5-(5-(3-amino-1,2,4-thiadiazol)ylmethyl)-1H-indol-3-yl]ethylamine 1. N,N-Dimethyl-2-[5-(4-methoxybenzyl)oxycarbonylmethyl-1H-indol-3-yl]ethylamine To a cooled (−70° C.) and stirred solution of 4-methoxybenzyl alcohol (6.3 g, 45.6 mmol) in dry THF (50 ml) was added dropwise n-butyllithium (1.6M in hexanes; 20 ml) over 0.2 h. After a further 5 min at −70° C., a solution of N,N-dimethyl-2-(5-carbomethoxymethyl-1H-indol-3-yl)ethylamine (2.5 g, 9.6 mmol) in THF (20 ml) was added dropwise over 5 min and the resulting solution allowed to warm to RT and stir for 1 h. Solvents were removed under vacuum and the residue dissolved in dry toluene (100 ml) and concentrated again. Water (50 ml) was added to the residue and extracted into Et₂O (2×150 ml). The combined organic solutions were washed once with brine (50 ml), dried (Na₂SO₄) and concentrated. Flash chromatography of the remaining oil (CH₂Cl₂/MeOH/NH₃; 90:10:1; silica) gave the title-compound (3.1 g, 89%); δ(360 MHz, CDCl₃) 2.33 (6H, s, NMe₂); 2.59-2.65 (2H, m, CH₂); 2.87-2.94 (2H, m, CH₂); 3.74 (2H, s, Ar—CH₂); 3.80 (3H, s, OMe); 5.07 (2H, s, Ar—CH₂—O); 6.83-6.88 (2H, m, Ar—H); 6.99 (1H, d, J=2.5 Hz, Ar—H); 7.10 (1H, dd, J=1.7 and 8.4 Hz, Ar—H); 7.23-7.29 (3H, m, Ar—H); 7.48 (1H, s, Ar—H); 8.04 (1H, brs, indole-NH).

2. N,N-Dimethyl-2-[5-(4-methoxybenzyl)oxycarbonylmethyl-1-tert-butoxycarbonyl-indol-3-yl]ethylamine To a solution of the preceding ester (3.4 g, 9.27 mmol) in dry CH₃CN (25 ml) was added di-tert-butyl dicarbonate (2.63 g, 12.06 mmol) followed by 4-DAMP (0.11 g). After stirring at RT for 1 h, solvents were removed under vacuum and the residue purified by flash chromatography (silica, CH₂Cl₂/MeOH; 95:5) to give the title-product (3.33 g, 77%); δ(360 MHz, CDCl₃) 1.66 (9H, s, 3 of CH₃); 2.32 (6H, s, N(Me)₂); 2.58-2.65 (2H, m, CH₂); 2.80-2.88 (2H, m, CH₂); 3.74 (2H, s, Ar—CH₂—CO); 3.80 (3H, s, OMe); 5.07 (2H, s, Ar—CH₂—O); 6.84-6.89 (2H, m, Ar—H); 7.18-7.28 (3H, m, Ar—H); 7.38 (1H, s, Ar—H); 7.41 (1H, d, J=1.2 Hz, Ar—H); 8.03 (1H, br d, J=8.1 Hz, Ar—H).

3. N,N-Dimethyl-2-[5-(5-(3-amino-1,2,4-thiadiazol)ylmethyl)-1H-indol-3-yl]ethylamine To a solution of the preceding ester (0.3 g, 0.64 mmol) in dry DMF (4 ml) was added NaH (64 mg of a 60% dispersion in oil) and the mixture stirred at RT for 15 min before adding a solution of 3-amino-5-chloro-1,2,4-thiadiazole (0.17 g, 1.27 mmol) in dry DMF (1 ml). After 1 h, water (50 ml) was added and products were extracted into CH₂Cl₂ (2×70 ml). The residue obtained on removal of solvents was chromatographed on silica-gel eluting with CH₂Cl₂/MeOH (10%) to give 64 mg (17%) of a white foam; δ(250 MHz, CDCl₃) 1.65 (9H, s, 3 of CH₃); 2.32 (6H, s, N(Me)₂); 2.57-2.64 (2H, m, CH₂); 2.78-2.84 (2H, m, CH₂); 3.78 (3H, s, OMe); 4.83 (2H, s, NH₂); 5.08 (1H, d, J=11.9 Hz, Ar—CH₂—O); 5.19 (1H, d, J=11.9 Hz, Ar—CH₂—O); 5.35 (1H, s, Ar—CH—CO); 6.79-6.84 (2H, m, Ar—H); 7.16-7.21 (2H, m, Ar—H); 7.28 (1H, dd, J=1.9 and 8.7 Hz, Ar—H); 7.41 (1H, s, Ar—H); 7.50 (1H, d, J=1.7 Hz, Ar—H); 8.06 (1H, d, J=8.3 Hz, Ar—H).

A solution of the preceding product (5 mg) in CH₂Cl₂ (0.8 ml), H₂O (30 μl) and TFA (130 μl) was stirred at RT for 1 h. Solvents were removed under vacuum and the remaining residue was dissolved in dry toluene (1.5 ml) and MeOH (0.3 ml) and concentrated again. The residue was dissolved in MeOH and refluxed for 0.5 min. The solvent was removed under vacuum and the residue purified by preparative thick layer chromatography (silica-gel, CH₂Cl₂/MeOH/NH₃; 80:20:1.5) to give N,N-dimethyl-2-[5-(5-(3-amino-1,2,4-thiadiazol)ylmethyl)-1H-indol-3-yl]ethylamine (1 mg); δ(250 MHz, CDCl₃) 2.50 (6H, s, N(Me)₂); 2.80-2.88 (2H, m, CH₂); 3.05-3.10 (2H, m, CH₂); 4.36 (2H, s, CH₂); 4.88 (2H, br s, NH₂); 7.09 (1H, d, J=2.5 Hz, Ar—H); 7.13 (1H, dd, J=1.7 and 8.4 Hz, Ar—H); 7.34 (1H, d, J=8.4 Hz, Ar—H); 7.55 (1H, s, Ar—H); 8.08 (1H, br s, indole-NH).

EXAMPLE 123

Tablet Preparation

Tablets containing 1.0, 2.0, 25.0, 26.0, 50.0 and 100.0 mg, respectively of:

N,N-Dimethyl-2-[5-[5-(3-Amino-1,2,4-oxadiazol)ylmethyl]-1H-indol-3-yl]ethyalmine. Hemisuccinate Hydrate.

2-[5-[3-(5-Benzyl-1,2,4-oxadiazol)yl]-1H-indol-3-yl]ethylamine. Hydrogen Maleate.

N,N-Dimethyl-2-[5-(2-(5-Methyl-1,3-oxazol)yl)-1H-indol-3-yl]ethylamine. Sesquioxalate.

4-[5-(3-(4-Methylsulphonylaminobenzyl)-1,2,4-oxadiazol-5-ylmethyl)-1H-indol-3-yl]N-methylpiperidine. Oxalate.

| TABLE FOR DOSES CONTAINING FROM 1-25 MG OF THE ACTIVE COMPOUND | | | |
|---|---|---|---|
| | Amount-mg | | |
| Active Compound | 1.0 | 2.0 | 25.0 |
| Microcrystalline cellulose | 49.25 | 48.75 | 37.25 |
| Modified food corn starch | 49.25 | 48.75 | 37.25 |
| Magnesium stearate | 0.50 | 0.50 | 0.50 |

| TABLE FOR DOSES CONTAINING FROM 26-100 MG OF THE ACTIVE COMPOUND | | | |
|---|---|---|---|
| | Amount-mg | | |
| Active Compound | 26.0 | 50.0 | 100.0 |
| Microcrystalline cellulose | 52.0 | 100.0 | 200.0 |
| Modified food corn starch | 2.21 | 4.25 | 8.5 |
| Magnesium stearate | 0.39 | 0.75 | 1.5 |

All of the active compound, cellulose, and a portion of the corn starch are mixed and granulated to 10% corn starch paste. The resulting granulation is sieved, dried and blended with the remainder of the corn starch and the magnesium stearate. The resulting granulation is then compressed into tablets containing 1.0 mg, 2.0 mg, 25.0 mg, 50.0 mg and 100 mg of the active ingredient per tablet.

What is claimed is:

1. A compound of formula I, or a salt or prodrug thereof:

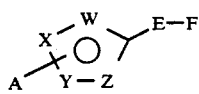
(I)

wherein the circle represents two non-adjacent double bonds in any position in the five-membered ring;

W, X, Y and Z independently represent oxygen, sulphur, nitrogen or carbon, provided that one of W, X, Y and Z represents oxygen or sulphur and at least one of W, X, Y and Z represents carbon;

A is selected from the group consisting of hydrogen, halogen, cyano, trifluoromethyl, nitro, $-OR^x$, $-OCOR^x$, $-ONR^xR^y$, $-SR^x$, $-NR^xR^y$, $-NR^xOR^y$, $-NR^zNR^xR^y$, $-NR^xCOR^y$, $-NR^xCO_2R^y$, $-NR^xSO_2R^y$, $-NR^zCVNR^xR^y$, $-COR^x$, $-CO_2R^x$, $-CONR^xR^y$, hydrocarbon selected from $C_{1-6}$ alkyl, $C_{2-6}$ alkenyl, $C_{2-6}$ alkynyl, $C_{3-7}$ cycloalkyl, $C_{3-7}$ cycloalkyl ($C_{1-6}$)alkyl, aryl, aryl ($C_{1-6}$)alkyl;

heterocycloalkyl selected from azetidinyl, pyrrolidyl, piperidyl, piperazinyl and morpholinyl;

heteroaryl selected from pyridyl, quinolyl, isoquinolyl, pyridazinyl, pyrimidinyl, pyrazinyl, pyranyl, furyl, benzofuryl, dibenzofuryl, thienyl, benzthienyl, imidazolyl, oxadiazolyl and thiadiazolyl;

heteroaryl ($C_{1-6}$)alkyl; and heterocyclo ($C_1$–$C_6$)alkyl;

wherein said hydrocarbon, heterocyclo or heteroaryl group is unsubstituted or substituted by one or more groups selected from $C_1$-$C_6$ alkyl, adamantyl, phenyl, halogen, $C_{1-6}$ haloalkyl, $C_{1-6}$ aminoalkyl, trifluoromethyl, hydroxy, $C_{1-6}$ alkoxy, aryloxy, keto, $C_{1-3}$ alkylenedioxy, nitro, cyano, carboxy, $C_{2-6}$ alkoxycarbonyl, $C_{2-6}$ alkoxycarbonyl ($C_{1-6}$)alkyl, $C_{2-6}$ alkylcarbonyloxy, arylcarbonyloxy, $C_{2-6}$ alkycarbonyl, arylcarbonyl, $C_{1-6}$ alkylthio, $C_{1-6}$ alkylsuphinyl, $C_{1-6}$ alkylsulphonyl, arylsulphonyl, $-NR^vR^w$, $-NR^vCOR^w$, $-NR^vCO_2R^w$, $-NR^vSO_2R^w$, $-CH_2NR^vSO_2R^w$, $-NHCONR^vR^w$, $-CONR^vR^w$, $-SO_2NR^vR^w$ and $-CH_2SO_2NR^vR^w$, in which $R^v$ and $R^w$ independently represent hydrogen, $C_{1-6}$ alkyl, aryl or aryl($C_{1-6}$)alkyl, and $R^v$ and $R^w$ when taken together represent a $C_{2-6}$ alkylene group;

E represents a bond or a straight or branched alkylene chain containing from 1 to 4 carbon atoms;

F represents a group of formula:

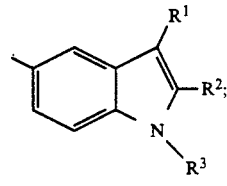

$R^1$ represents $-CH_2-CHR^4-NR^xR^y$ or a group of formula:

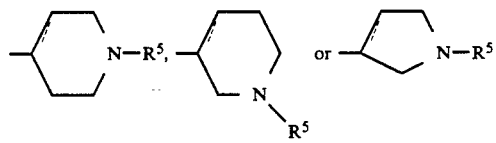

in which the broken line represents no bond or a single bond;

$R^2$, $R^3$, $R^4$ and $R^5$ are independently selected from the group consisting of hydrogen, $C_{1-6}$ alkyl, $C_{2-6}$ alkenyl and $C_{2-6}$ alkynyl;

$R^x$ and $R^y$ independently represent hydrogen or hydrocarbon, as defined above, or $R^x$ and $R^y$ together represent a $C_{2-6}$ alkylene group;

$R^z$ represents hydrogen or hydrocarbon, as defined above;

V represents oxygen, sulphur or a group of formula $=N-G$;

wherein G represents hydrocarbon as defined above, or an electron-withdrawing group selected from cyano, nitro, $-COR^x$, $-CO_2R^x$ or $-CO_2R^x$, in which $R^x$ is as defined above.

2. A compound according to claim 1 represented by formula IIA, or a salt or prodrug thereof:

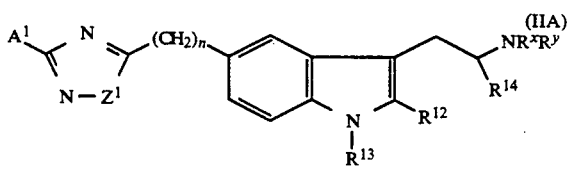

wherein
Z¹ represents oxygen or sulphur;
n is zero, 1, 2 or 3;
A¹ is selected from the group consisting of $C_{1-6}$ alkyl, $C_{2-6}$ alkenyl, $C_{2-6}$ alkynyl, $C_{3-7}$ cycloalkyl, aryl, aryl($C_{1-6}$)alkyl, $C_{3-7}$ heterocycloalkyl, heteroaryl and heteroaryl($C_{1-6}$)alkyl, any of which groups may be optionally substituted; and hydrogen, halogen, cyano, trifluoromethyl, nitro, $C_{1-6}$ alkoxy, $C_{1-6}$ alkylthio, —$NR^xR^y$ and —$CONR^xR^y$;
$R^{12}$, $R^{13}$ and $R^{14}$ are independently selected from the group consisting of hydrogen, $C_{1-6}$ alkyl, $C_{2-6}$ alkenyl and $C_{2-6}$ alkynyl; and
$R^x$ and $R^y$ independently represent hydrogen or hydrocarbon, or $R^x$ and $R^y$ together represent a $C_{2-6}$ alkylene group.

3. A compound according to claim 1 represented by formula IIB, or salt or prodrug thereof:

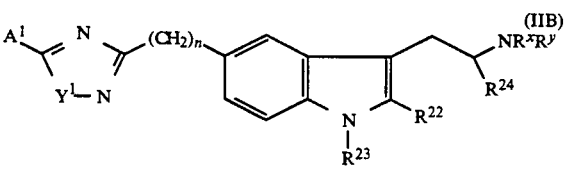

wherein
Y¹ represents oxygen or sulphur;
n is zero, 1, 2 or 3;
A¹ is as defined in claim 2;
$R^{22}$, $R^{23}$ and $R^{24}$ are independently selected from the group consisting of hydrogen, $C_{1-6}$ alkyl, $C_{2-6}$ alkenyl and $C_{2-6}$ alkynyl; and
$R^x$ and $R^y$ independently represent hydrogen or hydrocarbon, or $R^x$ and $R^y$ together represent a $C_{2-6}$ alkylene group.

4. A compound according to claim 1 represented by formula IIC, or salt or prodrug thereof:

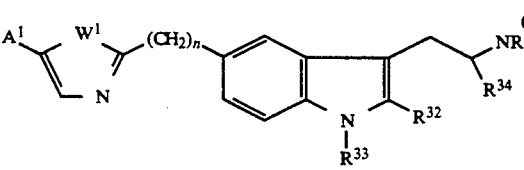

wherein
W¹ represents oxygen or sulphur;
n is zero, 1, 2 or 3;
A¹ is as defined in claim 2;
$R^{32}$, $R^{33}$ and $R^{34}$ are independently selected from the group consisting of hydrogen, $C_{1-6}$ alkyl, $C_{2-6}$ alkenyl and $C_{2-6}$ alkynyl; and
$R^x$ and $R^y$ independently represent hydrogen or hydrocarbon, or $R^x$ and $R^y$ together represent a $C_{2-6}$ alkylene group.

5. A compound according to claim 1 represented by formula IID, or salt or prodrug thereof:

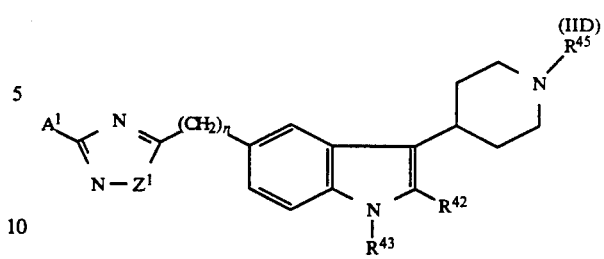

wherein
z¹ represents oxygen or sulphur;
n is zero, 1, 2 or 3;
A¹ is as defined in claim 2;
$R^{42}$, $R^{43}$ and $R^{45}$ are independently selected from the group consisting of hydrogen, $C_{1-6}$ alkyl, $C_{2-6}$ alkenyl and $C_{2-6}$ alkynyl; and
$R^x$ and $R^y$ independently represent hydrogen or hydrocarbon, or $R^x$ and $R^y$ together represent a $C_{2-6}$ alkylene group.

6. A compound according to claim 1 selected from:

2-[5-(3-benzyl-1,2,4-oxadiazol-5-yl)-1H-indol-3-yl]ethylamine;

2-[5-(3-methyl-1,2,4-oxadiazol-5-yl)-1H-indol-3-yl]ethylamine;

N,N-dimethyl-2-[5-(3-benzyl-1,2,4-oxadiazol-5-yl)-1H-indol-3-yl]ethylamine;

2-[5-(3-benzyl-1,2,4-oxadiazol-5-ylmethyl)-1H-indol-3-yl]ethylamine;

2-[5-(3-methyl-1,2,4-oxadiazol-5-ylmethyl)-1H-indol-3-yl]ethylamine;

2-[5-(3-amino-1,2,4-oxadiazol-5-ylmethyl)-1H-indol-3-yl]ethylamine;

2-[5-(3-phenyl-1,2,4-oxadiazol-5-ylmethyl)-1H-indol-3-yl]ethylamine;

2-[5-[3-(2-methoxybenzyl)-1,2,4-oxadiazol-5-ylmethyl]-1H-indol-3-yl]ethylamine;

N,N-dimethyl-2-[5-(3-benzyl-1,2,4-oxadiazol-5-ylmethyl)-1H-indol-3-yl]ethylamine;

2-[5-[2-(3-benzyl-1,2,4-oxadiazol-5-yl)ethyl]-1H-indol-3-yl]ethylamine;

N,N-dimethyl-2-[5-(3-methyl-1,2,4-oxadiazol-5-ylmethyl)-1H-indol-3-yl]ethylamine;

2-[5-(3-diphenylmethyl-1,2,4-oxadiazol-5-yl)-1H-indol-3-yl]ethylamine;

2-[5-(3-phenyl-1,2,4-oxadiazol-5-yl)-1H-indol-3-yl]ethylamine;

2-[5-[3-(2-methoxybenzyl)-1,2,4-oxadiazol-5-yl]-1H-indol-3-yl]ethylamine;

2-[5-[3-(3-benzyl-1,2,4-oxadiazol-5-yl)propyl]-1H-indol-3-yl]ethylamine;

2-[5-(3-phenethyl-1,2,4-oxadiazol-5-yl)-1H-indol-3-yl]ethylamine;

2-[5-(5-benzyl-1,2,4-oxadiazol-3-yl)-1H-indol-3-yl]ethylamine;

2-[5-(5-benzyl-1,2,4-oxadiazol-3-ylmethyl)-1H-indol-3-yl]ethylamine;

N,N-dimethyl-2-[5-[3-(2-methoxybenzyl)-1,2,4-oxadiazol-5-yl]-1H-indol-3-yl]ethylamine;

N,N-dimethyl-2-[5-[2-(3-benzyl-1,2,4-oxadiazol-5-yl)ethyl]-1H-indol-3-yl]ethylamine;

2-[5-[3-(1-naphthyl)-1,2,4-oxadiazol-5-ylmethyl]-1H-indol-3-yl]ethylamine;

2-[5-[3-(3-methyl-1,2,4-oxadiazol-5-yl)propyl]-1H-indol-3-yl]ethylamine;

2-[5-[3-(3-cyclopropyl-1,2,4-oxadiazol-5-yl)propyl]-1H-indol-3-yl]ethylamine;
2-[5-[3-(3-methoxybenzyl)-1,2,4-oxadiazol-5-yl]-1H-indol-3-yl]ethylamine;
2-[5-[3-(4-methoxybenzyl)-1,2,4-oxadiazol-5-yl]-1H-indol-3-yl]ethylamine;
2-[5-[3-(4-acetylaminobenzyl)-1,2,4-oxadiazol-5-yl]-1H-indol-3-yl]ethylamine;
2-[5-[3-(4-methylsulphonylaminobenzyl)-1,2,4-oxadiazol-5-yl]-1H-indol-3-yl]ethylamine;
2-[5-[3-(3-phenylpropyl)-1,2,4-oxadiazol-5-yl]-1H-indol-3-yl]ethylamine;
2-[5-(3-cyclopropyl-1,2,4-oxadiazol-5-yl)-1H-indol-3-yl]ethylamine;
2-[5-(3-ethyl-1,2,4-oxadiazol-5-yl)-1H-indol-3-yl]ethylamine;
2-[5-[3-(4-trifluoromethylbenzyl)-1,2,4-oxadiazol-5-yl]-1H-indol-3-yl]ethylamine;
N,N-dimethyl-2-[5-[3-(4-acetylaminobenzyl)-1,2,4-oxadiazol-5-yl]-1H-indol-3-yl]ethylamine;
N,N-dimethyl-2-[5-[3-(4-methylsulphonylaminobenzyl)-1,2,4-oxadiazol-5-yl]-1H-indol-3-yl]ethylamine;
N,N-dimethyl-2-[5-(3-amino-1,2,4-oxadiazol-5-ylmethyl)-1H-indol-3-yl]ethylamine;
2-[5-[2-(3-amino-1,2,4-oxadiazol-5-yl)ethyl]-1H-indol-3-yl]ethylamine;
2-[5-[2-(3-dimethylamino-1,2,4-oxadiazol-5-yl)ethyl]-1H-indol-3-yl]ethylamine;
2-[5-(5-methyl-1,2,4-oxadiazol-3-yl)-1H-indol-3-yl]ethylamine;
2-[5-(5-methyl-1,2,4-oxadiazol-3-ylmethyl)-1H-indol-3-yl]ethylamine;
N,N-dimethyl-2-[5-(5-benzyl-1,2,4-oxadiazol-3-ylmethyl)-1H-indol-3-yl]ethylamine;
2-[5-(3-methoxymethyl-1,2,4-oxadiazol-5-yl)-1H-indol-3-yl]ethylamine;
2-[5-[3-(4-methylaminocarbonylbenzyl)-1,2,4-oxadiazol-5-yl]-1H-indol-3-yl]ethylamine;
2-[5-[3-(4-methylaminocarbonylphenyl)-1,2,4-oxadiazol-5-yl]-1H-indol-3-yl]ethylamine;
2-[5-[3-(4-methylaminosulphonylbenzyl)-1,2,4-oxadiazol-5-yl]-1H-indol-3-yl]ethylamine;
2-[5-[3-(4-methylsulphonylbenzyl)-1,2,4-oxadiazol-5-yl]-1H-indol-3-yl]ethylamine;
2-[5-[3-(3-methylsulphonylaminobenzyl)-1,2,4-oxadiazol-5-yl]-1H-indol-3-yl]ethylamine;
2-[5-[3-(4-aminocarbonylaminobenzyl)-1,2,4-oxadiazol-5-yl]-1H-indol-3-yl]ethylamine;
2-[5-(3-amino-1,2,4-oxadiazol-5-yl)-1H-indol-3-yl]ethylamine;
2-[5-(3-acetylaminomethyl-1,2,4-oxadiazol-5-yl)-1H-indol-3-yl]ethylamine;
2-[5-[3-(2-acetylaminoethyl)-1,2,4-oxadiazol-5-yl]-1H-indol-3-yl]ethylamine;
2-[5-(3-aminomethyl-1,2,4-oxadiazol-5-yl)-1H-indol-3-yl]ethylamine;
N,N-dimethyl-2-[5-(3-amino-1,2,4-oxadiazol-5-yl)-1H-indol-3-yl]ethylamine;
N,N-dimethyl-2-[5-(3-acetylaminomethyl-1,2,4-oxadiazol-5-yl)-1H-indol-3-yl]ethylamine;
N,N-dimethyl-2-[5-[3-(2-acetylaminoethyl)-1,2,4-oxadiazol-5-yl]-1H-indol-3-yl]ethylamine;
N,N-dimethyl-2-[5-[3-(4-aminocarbonylaminobenzyl)-1,2,4-oxadiazol-5-yl]-1H-indol-3-yl]ethylamine;
N,N-dimethyl-2-[5-[3-(2-(t-butoxycarbonylamino)ethyl)-1,2,4-oxadiazol-5-yl]-1H-indol-3-yl]ethylamine;
N,N-dimethyl-2-[5-[3-(4-methylaminocarbonylbenzyl)-1,2,4-oxadiazol-5-yl]-1H-indol-3-yl]ethylamine;
N,N-dimethyl-2-[5-[3-(2-aminoethyl)-1,2,4-oxadiazol-5-yl]-1H-indol-3-yl]ethylamine;
N,N-dimethyl-2-[5-[3-(2-methylsulphonylaminoethyl)-1,2,4-oxadiazol-5-yl]-1H-indol-3-yl]ethylamine;
N,N-dimethyl-2-[5-[3-(2-aminocarbonylaminoethyl)-1,2,4-oxadiazol-5-yl]-1H-indol-3-yl]ethylamine;
N,N-dimethyl-2-[5-[3-(2-methylaminocarbonylaminoethyl)-1,2,4-oxadiazol-5-yl]-1H-indol-3-yl]ethylamine;
N,N-dimethyl-2-[5-[3-(2-methylaminocarbonylaminoethyl)-1,2,4-oxadiazol-5-yl]-1H-indol-3-yl]ethylamine;
N,N-dimethyl-2-[5-[3-(2-methoxycarbonylaminoethyl)-1,2,4-oxadiazol-5-yl]-1H-indol-3-yl]ethylamine;
N,N-dimethyl-2-[5-[3-(2-ethoxycarbonylaminoethyl)1,2,4-oxadiazol-5-yl]-1H-indol-3-yl]ethylamine;
N,N-dimethyl-2-[5-[2-(3-amino-1,2,4-oxadiazol-5-yl)ethyl]-1H-indol-3-yl]ethylamine;
N,N-dimethyl-2-[5-(3-methylamino-1,2,4-oxadiazol-5-ylmethyl)-1H-indol-3-yl]ethylamine;
N,N-dimethyl-2-[5-[3-(4-aminocarbonylbenzyl)-1,2,4-oxadiazol-5-ylmethyl]-1H-indol-3-yl]ethylamine;
N,N-dimethyl-2-[5-[3-(4-acetylaminobenzyl)-1,2,4-oxadiazol-5-ylmethyl]-1H-indol-3-yl]ethylamine;
N,N-dimethyl-2-[5-[3-(4-methylaminosulphonylbenzyl)-1,2,4-oxadiazol-5-ylmethyl]-1H-indol-3-yl]ethylamine;
N,N-dimethyl-2-[5-[3-(4-aminocarbonylaminobenzyl)-1,2,4-oxadiazol-5-ylmethyl]-1H-indol-3-yl]ethylamine;
N,N-dimethyl-2-[5-[3-(4-methylsulphonylaminobenzyl)-1,2,4-oxadiazol-5-ylmethyl]-1H-indol-3-yl]ethylamine;
N,N-dimethyl-2-[5-[3-(4-methylaminocarbonylphenyl)-1,2,4-oxadiazol-5-ylmethyl]-1H-indol-3-yl]ethylamine;
N,N-dimethyl-2-[5-(3-acetylaminomethyl-1,2,4-oxadiazol-5-ylmethyl)-1H-indol-3-yl]ethylamine;
N,N-dimethyl-2-[5-(3-methylsulphonylaminomethyl-1,2,4-oxadiazol-5-ylmethyl)-1H-indol-3-yl]ethylamine;
N,N-dimethyl-2-[5-(3-aminocarbonylmethyl-1,2,4-oxadiazol-5-ylmethyl)-1H-indol-3-yl]ethylamine;
N,N-dimethyl-2-[5-[3-(3-methylsulphonylaminobenzyl)-1,2,4-oxadiazol-5-ylmethyl]-1H-indol-3-yl]ethylamine;
N,N-dimethyl-2-[5-[3-(3-acetylaminobenzyl)-1,2,4-oxadiazol-5-ylmethyl]-1H-indol-3-yl]ethylamine;
N,N-dimethyl-2-[5-[3-(4-aminocarbonylphenyl)-1,2,4-oxadiazol-5-ylmethyl]-1H-indol-3-yl]ethylamine;
N,N-dimethyl-2-[5-[3-(3-aminocarbonylphenyl)-1,2,4-oxadiazol-5-ylmethyl]-1H-indol-3-yl]ethylamine;
N,N-dimethyl-2-[5-[3-(4-methylsulphonylaminophenyl)-1,2,4-oxadiazol-5-ylmethyl]-1H-indol-3-yl]ethylamine;
N,N-dimethyl-2-[5-[3-(4-methylaminosulphonylmethylphenyl)-1,2,4-oxadiazol-5-ylmethyl]-1H-indol-3-yl]ethylamine;
N,N-dimethyl-2-[5-[3-(3-methylaminosulphonylmethylphenyl)-1,2,4-oxadiazol-5-ylmethyl]-1H-indol-3-yl]ethylamine;
N,N-dimethyl-2-[5-[3-(4-aminosulphonylmethylphenyl)-1,2,4-oxadiazol-5-ylmethyl]-1H-indol-3-yl]ethylamine;
N,N-dimethyl-2-[5-[3-(4-dimethylaminosulphonylmethylphenyl)-1,2,4-oxadiazol-5-ylmethyl]-1H-indol-3-yl]ethylamine;
N,N-dimethyl-2-8 5-[3-(t-butoxycarbonylamino)methyl-1,2,4-oxadiazol-5-ylmethyl]-1H-indol-3-yl]ethylamine;

N,N-dimethyl-2-[5-[3-(2-(t-butoxycarbonylamino)ethyl)-1,2,4-oxadiazol-5-ylmethyl]-1H-indol-3-yl]ethylamine;
N,N-dimethyl-2-[5-(3-aminomethyl-1,2,4-oxadiazol-5-ylmethyl)-1H-indol-3-yl]ethylamine;
N,N-dimethyl-2-[5-(3-methoxycarbonylaminomethyl-1,2,4-oxadiazol-5-ylmethyl)-1H-indol-3-yl]ethylamine;
N,N-dimethyl-2-[5-(3-dimethylaminomethyl-1,2,4-oxadiazol-5-ylmethyl)-1H-indol-3-yl]ethylamine;
N,N-dimethyl-2-[5-[3-(2-methylsulphonylaminoethyl)-1,2,4-oxadiazol-5-ylmethyl]-1H-indol-3-yl]ethylamine;
N,N-dimethyl-2-[5-[3-(2-ethoxycarbonylaminoethyl)-1,2,4-oxadiazol-5-ylmethyl]-1H-indol-3-yl]ethylamine;
N,N-dimethyl-2-[5-(3-benzoylaminomethyl-1,2,4-oxadiazol-5-ylmethyl)-1H-indol-3-yl]ethylamine;
N,N-dimethyl-2-[5-[3-(2-benzoylaminoethyl)-1,2,4-oxadiazol-5-ylmethyl]-1H-indol-3-yl]ethylamine;
N,N-dimethyl-2-[5-[3-(2-phenylaminocarbonylaminoethyl)-1,2,4-oxadiazol-5-ylmethyl]-1H-indol-3-yl]ethylamine;
N,N-dimethyl-2-[5-[3-(2-(t-butylaminocarbonylamino)ethyl-1,2,4-oxadiazol-5-ylmethyl]-1H-indol-3-yl]ethylamine;
N-methyl-2-[5-(3-amino-1,2,4-oxadiazol-5-ylmethyl)-1H-indol-3-yl]ethylamine;
N,N-dimethyl-2-[5-[3-(4-(t-butoxycarbonyl)piperazin-1-yl)-1,2,4-oxadiazol-5-ylmethyl]-1H-indol-3-yl]ethylamine;
N,N-dimethyl-2-[5-[3-(4-methylsulphonylpiperazin-1-yl)-1,2,4-oxadiazol-5-ylmethyl]-1H-indol-3-yl]ethylamine;
N,N-dimethyl-2-[5-[3-(4-methoxycarbonylpiperazin-1-yl)-1,2,4-oxadiazol-5-ylmethyl]-1H-indol-3-yl]ethylamine;
N,N-dimethyl-2-[5-[3-(4-methylaminocarbonylpiperazin-1-yl)-1,2,4-oxadiazol-5-ylmethyl]-1H-indol-3-yl]ethylamine;
N,N-dimethyl-2-[5-[3-(4-acetylpiperazin-1-yl)-1,2,4-oxadiazol-5-ylmethyl]-1H-indol-3-yl]ethylamine;
N,N-dimethyl-2-[5-[3-(4-methylsulphonylaminomethylphenyl)-1,2,4-oxadiazol-5-yl-methyl]-1H-indol-3-yl]ethylamine;
N,N-dimethyl-2-[5-(3-phenylsulphonylaminomethyl-1,2,4-oxadiazol-5-ylmethyl)-1H-indol-3-yl]ethylamine;
N,N-dimethyl-2-[5-(3-benzylamino-1,2,4-oxadiazol-5-ylmethyl)-1H-indol-3-yl]ethylamine;
N,N-dimethyl-2-[5-[3-(3-pyridyl)methyl-1,2,4-oxadiazol-5-ylmethyl]-1H-indol-3-yl]ethylamine;
N,N-dimethyl-2-[5-[3-(2-methoxypyrid-5-yl)methyl-1,2,4-oxadiazol-5-ylmethyl]-1H-indol-3-yl]ethylamine;
2-[5-[3-(4-acetylaminobenzyl)-1,2,4-oxadiazol-5-ylmethyl]-1H-indol-3-yl]ethylamine;
2-[5-[3-(4-methylsulphonylaminobenzyl)-1,2,4-oxadiazol-5-ylmethyl]-1H-indol-3-yl]ethylamine;
2-[5-[2-[3-(4-acetylaminobenzyl)-1,2,4-oxadiazol-5-yl]ethyl]-1H-indol-3-yl]ethylamine;
2-[5-[2-[3-(4-methoxybenzyl)-1,2,4-oxadiazol-5-yl]ethyl]-1H-indol-3-yl]ethylamine;
N,N-dimethyl-2-[5-(5-methyl-1,3-oxazol-2-yl)-1H-indol-3-yl]ethylamine;
N,N-dimethyl-2-[5-[2-(5-methyl-1,3-oxazol-2-yl)ethyl]-1H-indol-3-yl]ethylamine;
1-methyl-4-[5-(3-amino-1,2,4-oxadiazol-5-yl)-1H-indol-3-yl]piperidine;
1-methyl-4-[5-(3-amino-1,2,4-oxadiazol-5-ylmethyl)-1H-indol-3-yl]piperidine;
1-methyl-4-[5-[3-(4-methylsulphonylaminobenzyl)-1,2,4-oxadiazol-5-ylmethyl]-1H-indol-3-yl]piperidine;
1-methyl-4-[5-[3-(3-pyridyl)methyl-1,2,4-oxadiazol-5-ylmethyl]-1H-indol-3-yl]piperidine;
N,N-dimethyl-2-[5-[3-(4-pyridyl)methyl-1,2,4-oxadiazol-5-ylmethyl]-1H-indol-3-yl]ethylamine;
N,N-dimethyl-2-[5-[3-(2-(t-butoxycarbonylamino)ethyl)amino-1,2,4-oxadiazol-5-ylmethyl]-1H-indol-3-yl]ethylamine;
2-[5-(3-aminocarbonyl-1,2,4-oxadiazol-5-ylmethyl)-1H-indol-3-yl]ethylamine;
2-[5-(3-methylaminocarbonyl-1,2,4-oxadiazol-5-ylmethyl)-1H-indol-3-yl]ethylamine;
2-[5-[3-(pyrrolid-1-yl)carbonyl-1,2,4-oxadiazol-5-ylmethyl]-1H-indol-3-yl]ethylamine;
2-[5-[3-(azetidin-1-yl)carbonyl-1,2,4-oxadiazol-5-ylmethyl]1H-indol-3-yl]ethylamine;
N,N-dimethyl-2-[5-[3-(4-phenylsulphonylpiperazin-1-yl)-1,2,4-oxadiazol-5-ylmethyl]-1H-indol-3-yl]ethylamine;
N,N-dimethyl-2-[5-[3-(2-(pyrrolid-1-ylcarbonylamino)ethyl)-1,2,4-oxadiazol-5-ylmethyl]-1H-indol-3-yl]ethylamine;
N,N-dimethyl-2-[5-[3-(2-methylsulphonylaminoethyl)amino-1,2,4-oxadiazol-5-ylmethyl]-1H-indol-3-yl]ethylamine;
N,N-dimethyl-2-[5-(3-amino-1,4-thiadiazol-5-ylmethyl)-1H-indol-3-yl]ethylamine;
and salts and prodrugs thereof.

7. A pharmaceutical composition comprising an effective amount of a compound according to claim 1 in association with a pharmaceutically acceptable carrier or excipient.

* * * * *

UNITED STATES PATENT AND TRADEMARK OFFICE
CERTIFICATE OF CORRECTION

PATENT NO. : 5,317,103
DATED : May 31, 1994
INVENTOR(S) : Raymond Baker, et al

It is certified that error appears in the above-indentified patent and that said Letters Patent is hereby corrected as shown below:

At Column 54, in claim 1, please replace line 16, which reads "arylcarbonyloxy, $C_{2-6}$alkycarbonyl, arylcarbonyl, $C_{1-6}$" with -- arylcarbonyloxy, $C_{2-6}$alkylcarbonyl, arylcarbonyl, $C_{1-6}$ --.

At Column 54, in claim 1, please replace line 17, which reads "alkylthio, $C_{1-6}$alkylsuphinyl, $C_{1-6}$alkylsulphonyl, aryl-" with -- alkylthio, $C_{1-6}$alkylsulphinyl, $C_{1-6}$alkylsulphonyl, aryl- --.

At Column 58, in claim 6, please replace line 66, which reads "N,N-dimethyl-2-8 5-[3-(t-butoxycarbonylamino)meth-" with -- N,N-dimethyl-2-[5-[3-(t-butoxycarbonylamino)meth- --.

Signed and Sealed this

Sixteenth Day of May, 1995

*Attest:*

BRUCE LEHMAN

*Attesting Officer*   Commissioner of Patents and Trademarks